United States Patent [19]

Alig et al.

[11] Patent Number: 5,973,188
[45] Date of Patent: Oct. 26, 1999

[54] ACETIC ACID DERIVATIVES

[75] Inventors: Leo Alig, Kaiseraugst; Paul Hadvary, Biel-Benken; Marianne Hürzeler Müller, Däniken; Marcel Müller, Frenkendorf; Beat Steiner, Bättwil; Thomas Weller, Basel, all of Switzerland

[73] Assignee: Hoffmann-La Roche Inc., Nutley, N.J.

[21] Appl. No.: 08/963,413

[22] Filed: Nov. 3, 1997

Related U.S. Application Data

[62] Division of application No. 08/347,736, Dec. 1, 1994, Pat. No. 5,726,185.

[30] Foreign Application Priority Data

Dec. 3, 1993 [CH] Switzerland .............................. 3609/93
Oct. 25, 1994 [CH] Switzerland .............................. 3198/94

[51] Int. Cl.⁶ .................... C07C 229/28; C07C 229/02
[52] U.S. Cl. .................... 560/35; 514/212; 514/307; 514/317; 514/327; 514/331; 514/352; 514/538; 514/564; 540/593; 540/594; 540/606; 546/192; 546/216; 546/221; 546/304; 546/323; 562/440

[58] Field of Search .................... 514/538, 352, 514/212, 354, 327, 331, 317, 307; 560/35; 562/440; 546/304, 323, 192, 216, 221, 150; 540/593, 594, 606

[56] References Cited

U.S. PATENT DOCUMENTS

| | | | |
|---|---|---|---|
| 5,039,805 | 8/1991 | Alig et al. | 546/224 |
| 5,084,466 | 1/1992 | Alig et al. | 514/353 |
| 5,256,812 | 10/1993 | Alig et al. | 560/35 |
| 5,273,982 | 12/1993 | Alig et al. | 514/315 |
| 5,378,712 | 1/1995 | Alig et al. | 514/315 |
| 5,399,585 | 3/1995 | Alig et al. | 514/438 |
| 5,576,444 | 11/1996 | Himmelsbach | 548/413 |

FOREIGN PATENT DOCUMENTS

| | | |
|---|---|---|
| 641 770 | 3/1994 | European Pat. Off. . |
| 632 020 | 6/1994 | European Pat. Off. . |
| 2680196 | 8/1997 | Japan . |
| 94/15913 | 12/1993 | WIPO . |
| 95/01336 | 6/1994 | WIPO . |

OTHER PUBLICATIONS

Alig, et al., J. Med. Chem. 35:4393–4407 (1992) "Low Molecular Weight, Non–Peptide Fibrinogen Receptor Antagonists".

Alexander J et al. J. Med. Chem. 31(2), 318–322, 1988.

*Primary Examiner*—Evelyn Mei Huang
*Attorney, Agent, or Firm*—George W. Johnston; William H. Epstein; John P. Parise

[57] ABSTRACT

Acetic acid derivatives of the formula

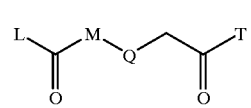

wherein L, M, T and Q have the significance given in the description, can be used for the treatment or prophylaxis of illnesses which are caused by the binding of adhesive proteins to blood platelets and by blood platelet aggregation and cell—cell adhesion, and are manufactured by cleaving protecting groups in the corresponding protected compounds or by converting the cyano group into the amidino group in corresponding nitrites.

8 Claims, No Drawings

ACETIC ACID DERIVATIVES

This is a division of application Ser. No. 08/347,736, filed Dec. 1, 1994, U.S. Pat. No. 5,726,185.

BACKGROUND OF THE INVENTION

The present invention is concerned with compounds which are novel acetic acid derivatives, a process for their manufacture, pharmaceutical preparations which contain such compounds as well as the use of these compounds for the production of pharmaceutical preparations.

SUMMARY OF THE INVENTION

In particular, the invention is concerned with acetic acid derivatives of the formula

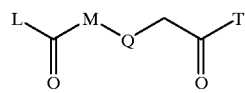

I wherein

L is a group of formula $L^1$ to $L^5$:

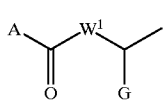

L¹

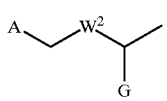

L²

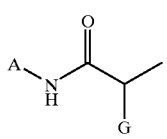

L³

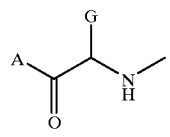

L⁴

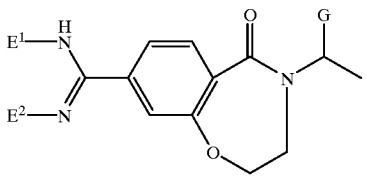

L⁵ in which a carbonyl group present in the L group and/or between the L and M groups which is not bonded in the form of an amide can also be present as an oxime, A is a group of formula $A^1$ to $A^4$:

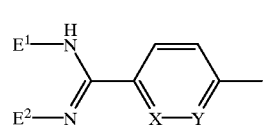

A¹

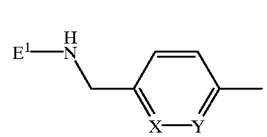

A²

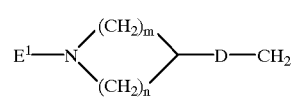

A³

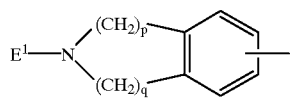

A⁴

$E^1$ and $E^2$ are H, lower-alkyl, OH, lower-alkoxy, lower-alkoxy-lower-alkyl, carboxy-lower-alkyl, $P(O)(O\text{-lower-alkyl})_2$, $C(O)OR^1$, $OC(O)R^1$, $OC(O)OR^1$ or $C(O)SR^1$, provided that at least one of $E^1$ and $E^2$ is H, or $E^1$ and $E^2$ together with the N atoms to which they are attached are a (5,5-dimethyl or 5-oxo)-4,5-dihydro-1, 2,4-oxadiazol-3-yl group, $R^1$ is lower-alkoxy-lower-alkyl, lower-alkyl, or R1 is lower-alkyl substituted by OH, COOH, lower-alkoxycarbonyl, lower-alkanoyloxy, lower-alkenoyloxy, optionally substituted benzoyloxy or lower-alkyl-CONH, or R1 is phenyl which is optionally substituted and optionally bonded via lower-alkylene, or R1 is cycloalkyl optionally interupted by O, one of X and Y is CH and the other is CH, C-lower-alkyl, C-lower-alkoxy or N, D is a group $(CH_2)_s$ or $(CH_2)_tO$, s is 1 to 4, m and n are 0 to 5 and t is 0 to 3, but m+n are 1 to 5 and each of m+t and n+t is at least 1, p and q are 0 to 5, but p+q is 2 to 5, $W^1$ is $CH_2$, alkyl-CH, lower-alkyl-OC(O)CH, NH, lower-alkyl-N or lower-alkoxy-lower-alkyl-N, $W^2$ is O, NH, acyl-N or lower-alkyl-OC(O)—N, G is H or the characterizing group of an α-aminocarboxylic acid, M is 1,4-piperidinylene bonded via the N atom to the keto group or 1,4-phenylene optionally substituted by lower-alkyl, lower-alkoxy, $OCH_2COOH$ or $OCH_2COO$-lower-alkyl, Q is O, $CH_2$, NH, acyl-N or lower-alkyl OC(O)N, T is $NH_2$, NH-lower-alkyl, NH-lower-alkyl (COOH or COO-lower-alkyl), lower-alkoxy or lower-alkenyloxy substituted by lower-alkoxy, COOH, COO-lower-alkyl, lower-alkyl-COO or lower-alkyl-OCOO, or a group OT', T' is H, lower-alkyl, T' is phenyl or pyridyl optionally bonded via lower-alkylene or T' is cycloalkyl optionally bonded via lower-alkylene and optionally interrupted by O, by NH or by NCOO-lower-alkyl, with the provisos a) and b) as follows, that:
a) T' is different from H, lower-alkyl and phenyl-lower-alkyl in those derivatives where
L is a group of the formula

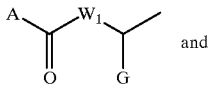
and
L¹

A is a group of the formula

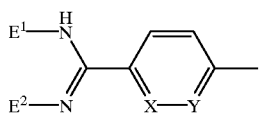
A¹ where
one of E¹ and E² is hydrogen and the other is hydrogen, tert-butoxycarbonyl or benzyloxycarbonyl, and
one of X and Y is CH and the other is CH or N and
W¹ is NH, lower-alkyl-N or lower-alkoxy-lower-alkyl-N,
G is as defined above,
M is 1,4-piperidinylene bonded via the N atom to the keto group and
Q is O,
b) T' is also different from H, lower-alkyl, phenyl and phenyl-lower-alkyl in those derivatives where
L is a group of formula L¹¹, L³¹ or L⁴¹:

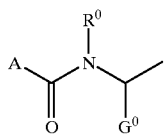
L¹¹

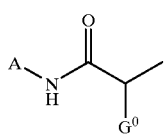
L³¹

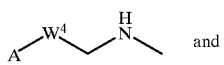
and
L⁴¹

A is a group of the formula

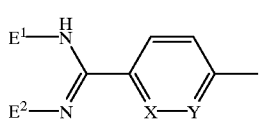
A¹ where
one of E¹ and E² is hydrogen and the other is hydrogen, tert-butoxycarbonyl or benzyloxycarbonyl,
one of X and Y is CH and the other is CH, C-lower-alkyl, C-lower-alkoxy or N, R° and G° are H or lower-alkyl,
W⁴ is C=O or C=NOH,
M is 1,4-phenylene optionally substituted by lower-alkyl, lower-alkoxy, $OCH_2COOH$ or $OCH_2COO$-lower-alkyl and Q is O, CH2 or NH.

Also included are hydrates or solvates and physiologically usable salts of any and all of the above derivatives.

DETAILED DESCRIPTION OF THE INVENTION

In the scope of the present invention "lower" denotes straight-chain or branched groups with 1 to 6, preferably 1 to 4, C atoms. This definition applies to all the groups herein which are characterized as "lower". Thus, methyl, ethyl, propyl, isopropyl, n-, s- and t-butyl and hexyl are examples of lower-alkyl; methoxy and ethoxy are examples of lower-alkoxy; loweralkoxy-lower alkyl, is, for example, any combination of the above lower alkyl groups with the above lower alkoxy groups. Lower alkoxy carbonyl and carbonyl loweralkoxy are, for example, methoxy or ethoxy attached to a carbonyl group. Acetyl and propionyl are examples of lower-alkanoyl. Methacryloyl is an example of lower-alkenoyl and pentenyloxy is an example of lower-alkenyloxy. An example of lower alkanoyloxy is acetoxy.

Halogen and lower-alkoxy are examples of possible substituents when $R^1$ is an optionally substituted phenyl group. $R^1$ as a phenyl group may be bonded via alkylene to O or S when E1 or E2 are C(O)OR1, OC(O)R1, OC(O)OR1 or C(O)SR1. $R^1$ may be benzyl, or $C_{3-6}$-cycloalkyl optionally interrupted by O, for example tetrahydropyranyl. Thus by "interrupted by O" is meant a cycloalkyl which contains at least one oxygen atom within the ring and adjacent to a ring carbon. When R1 is lower alkyl optionally substituted with benzoyloxy, the benzoyloxy may have as a substituent a lower-alkanoyloxy group such as acetoxy. The benzyloxy may have more than one such substituent When T is OT' and T' is a phenyl, pyridyl, or cycloalkyl group, T may be bonded to the O via lower-alkylene. T' as cycloalkyl may be optionally interrupted by O, NH or NCOO-lower-alkyl. By "interrupted by O, NH or NCOO-lower-alkyl" is meant cycloalkyl which contains at least one heteroatom such as N or O within the ring and located adjacent to a ring carbon, and which may have a substituent such as COO-loweralkyl. Examples of such groups are those with 3 to 6 C atoms in the cyclic part, such as cyclopropyl, cyclohexyl, tetrahydropyranyl, piperidinyl and N-(t-butoxycarbonyl)piperidinyl.

The term "characterizing group of an alpha (or α)-aminocarboxylic acid" denotes the group G in a natural or synthetic α-amino acid of the formula $H_2NCH(G)COOH$. Groups G present in natural α-amino acids are methyl (in alanine), isopropyl (in valine), benzyl (in phenylalanine), p-hydroxybenzyl (in tyrosine), $CH_2SH$ (in cysteine), $CH_2OH$ (in serine), 1-hydroxyethyl (in threonine) and the like. Further, G is, for example, a lower-alkyl group optionally substituted by OH, SH, lower-alkylthio, aryl, $NH_2$, NH—$R^a$, N($R^a$, $R^b$) or O$R^a$, wherein $R^a$ and $R^b$ are lower-alkyl, lower-alkoxy-lower-alkyl, acyl or lower-alkoxycarbonyl. Further, a lower-alkyl group G can be substituted by $CONH_2$ or CONH-lower-alkyl. The above aryl is e.g. phenyl or phenyl substituted by OH, $NH_2$, NH—$R^a$, N($R^a$, $R^b$) or O$R^a$. The above acyl is e.g. lower-alkanoyl, aroyl or heteroaroyl in which aroyl is an aryl group as defined above which is bonded via CO, such as benzoyl or lower-alkanoyloxybenzoyl, and heteroaroyl is e.g. a 5- to 6-membered, O- or NH-containing heteroaromatic group which is bonded via CO, such as furoyl.

The compounds of formula I can be solvated, especially hydrated. The hydration can be effected in the course of the manufacturing process or can occur gradually as a consequence of hygroscopic properties of an initially anhydrous compound of formula I.

Examples of physiologically usable salts of the compounds of formula I are salts with physiologically compatible mineral acids such as hydrochloric acid, sulphuric acid or phosphoric acid; or with organic acids such as methanesulphonic acid, acetic acid, trifluoroacetic acid, citric acid, fumaric acid, maleic acid, tartaric acid, succinic acid or salicylic acid. The compounds of formula I having a free carboxy group can also form salts with physiologically compatible bases. Examples of such salts are alkali metal, alkaline earth metal, ammonium and alkylammonium salts such as the Na, K, Ca or tetramethylammonium salt. The compounds of formula I can also be present in the form of zwitterions.

The compounds of formula I which contain one or more asymmetric C atoms can be present as enantiomers, as diastereomers or as mixtures thereof, e.g. as racemates.

The compounds in accordance with the invention can be divided into the following groups:

a) those wherein L is a group $L^1$ in which A is a group $A^1$ and of the formula

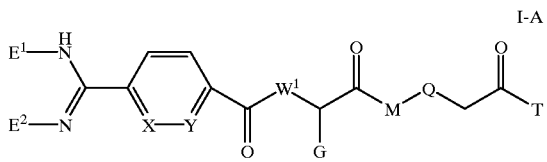

wherein $E^1$, $E^2$, X, Y, $W^1$, G, M, Q and T are as defined above for Formula I, b) those wherein L is a group $L^1$ in which A is a group $A^3$ and of the formula

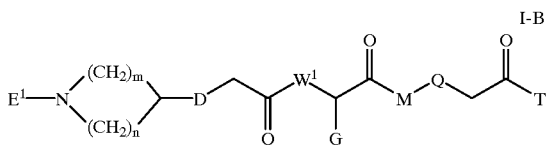

wherein $E^1$, m, n, D, $W^1$, G, M, Q and T are as defined above for Formula I. In particular E1 may be H, OH, or C(O))R1, m and n may be 2, W1 may be NH, D and Q may be O, G may be lower-alkyl, M may be 1.4-phenylene, and T may be lower-alkoxy. These definitions may be simultaneous or separate, however in a preferred composition all the definitions are simultaneously as above and G is specifically methyl and T is specifically ethoxy, or all the definitions are simultaneously as above and E1 is lower-alkanoyloxy-lower-alkoxycarbonyl, specifically acetomethoxycarbonyl.

c) those wherein L is a group $L^1$ in which A is a group $A^2$ and of the formula

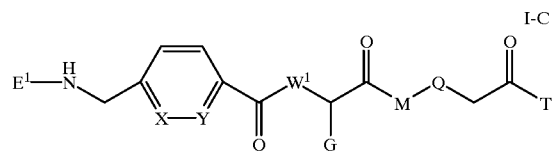

wherein $E^1$, X, Y, $W^1$, G, M, Q and T are as defined above for Formula and in a preferred compound, Q is O and T is OH or lower-alkoxy, d) those wherein L is a group $L^1$ in which A is a group $A^4$ and of the formula

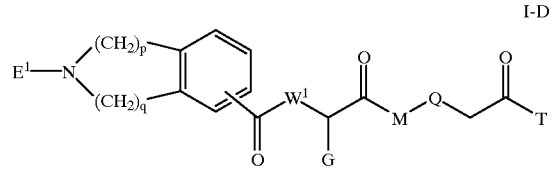

wherein $E^1$, p, q, $W^1$, G, M, Q and T are as defined above for Formula I, and in a preferred compound M is 1,4-phenylene, Q is O and T is lower-alkoxy, e) those wherein L is a group $L^2$ in which A is a group $A^1$ and of the formula

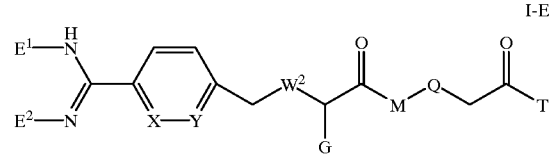

wherein $E^1$, $E^2$, X, Y, $W^2$, G, M, Q and T are as defined above for Formula I, and in a preferred compound M is 1,4-piperidinylene bonded via the N atom to the keto group, Q is O and T is lower-alkoxy, f) those wherein L is a group $L^3$ in which A is a group $A^1$ and of the formula

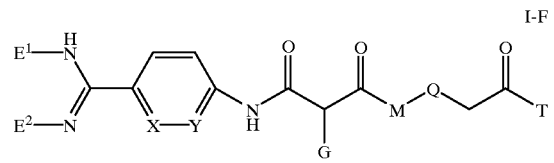

wherein $E^1$, $E^2$, X, Y, G, M, Q and T are as defined above for Formula I, and in a preferred compound M is 1,4-piperidinylene bonded via the N atom to the keto group, Q is O and T is lower-alkoxy, g) those wherein L is a group $L^4$ in which A is a group $A^1$ and of the formula

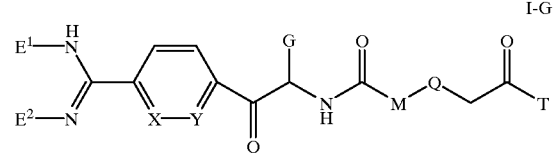

wherein $E^1$, $E^2$, X, Y, G, M, Q and T are as defined above, for Formula I and in a preferred compound M is 1,4-phenylene, Q is O and T is lower-alkoxy, h) those wherein L is a group $L^5$ and of the formula

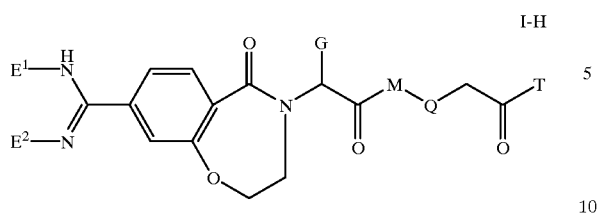

I-H wherein $E^1$, $E^2$, G, M, Q and T are as defined above for Formula I, and in a preferred compound M is 1,4-piperidinylene bonded via the N atom to the keto group, Q is O and T is lower-alkoxy.

Examples of acetic acid derivatives of the present invention are those in which L is a group of the formula

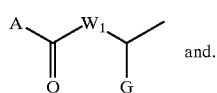

$L^1$ and.

A is a group $A^1$, $A^2$ or $A^{30}$:

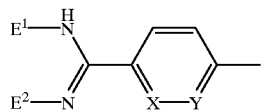

$A^1$

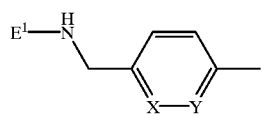

$A^2$

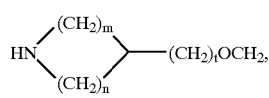

$A^{30}$ where
one of $E^1$ and $E^2$ is H and the other is H, lower-alkyl, OH, lower-alkoxy, lower-alkoxy-lower-alkyl, carboxy-lower-alkyl, PO(O-lower-alkyl)$_2$, C(O)OR$^1$ or OC(O)OR$^1$, R$^1$ is lower-alkoxy-lower-alkyl, lower-alkyl, or R1 is lower-alkyl substituted by OH, COOH or lower-alkenoyloxy, or R1 is phenyl which is optionally substituted and optionally bonded via lower-alkylene, (as defined above), or R1 is cycloalkyl optionally interrupted by O, (as defined above), and one of X and Y is CH and the other is CH or N, m and n are 0 to 5 and t is 0 to 3, but m+n is 1 to 5 and each of m+t and n+t is at least 1, W$^1$ is CH$_2$, lower-alkyl-OCOCH, NH, lower-alkyl-N or lower-alkoxy-lower-alkyl-N, G is H or the characterizing group of an α-amino-carboxylic acid, M is as defined above for Formula I, Q is oxygen, T is a group OT" and T is H, lower-alkyl, lower-alkoxy-lower-alkyl or cycloalkyl optionally bonded via lower-alkylene and optionally interrupted by O (as defined above), with the provisos a) and b) as follows, that:

a) T" is different from H, lower-alkyl and phenyl-lower-alkyl where

A is a group of the formula

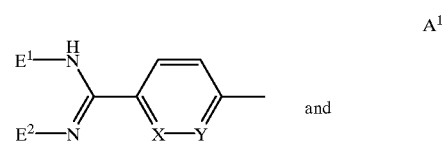

$A^1$ and $E^1$ and $E^2$ are hydrogen, tert-butoxycarbonyl or benzyloxy-carbonyl, X, Y, G and Q are as defined for Formula I above, W$^1$ is NH, lower-alkyl-N or lower-alkoxy-lower-alkyl-N and M is 1,4-piperidinylene bonded via the N atom to the keto group, or b) T" is different from H, lower-alkyl, phenyl and phenyl-lower-alkyl in those derivatives where L is a group of formula $L^{11}$:

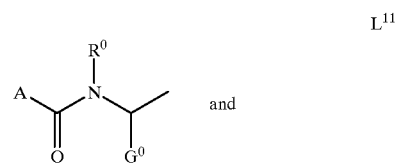

$L^{11}$ and

A is a group of the formula

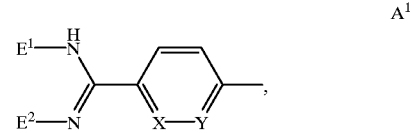

$A^1$ where
$E^1$ and $E^2$ are hydrogen, tert-butoxycarbonyl or benzyloxy-carbonyl, X, Y and Q are as defined for Formula I above, R° and G° are H or lower-alkyl and M is 1,4-phenylene optionally substituted by lower-alkyl, lower-alkoxy, OCH$_2$COOH or OCH$_2$COO-lower-alkyl.

Also included are physiologically usable salts of all such derivatives.

Preferred compounds of Formula I, in particular those of Formula I-A, are those in which one of $E^1$ and $E^2$ is H and the other is H, OH, C(O)OR$^1$ or OC(O)OR$^1$ and/or R$^1$ is lower-alkyl, such as ethyl, butyl or isobutyl, lower-alkoxy-lower-alkyl, such as methoxyethyl, lower-alkyl substituted by benzoyloxy or lower-alkanoyloxy, such as benzoyloxymethyl, acetoxymethyl, acetoxyethyl or pivaloyloxymethyl, or phenyl and/or one of X and Y is CH and the other is CH or N and/or W$^1$ is NH or CH$_2$ and/or Q is O or CH$_2$ and/or G is H, lower-alkyl, such as methyl or ethyl, or lower-alkoxycarbonylamino-lower-alkyl, such as ethoxycarbonylaminopropyl, and/or M is 1,4-piperidinylene bonded via the N atom to the keto group, 1,4-phenylene or 1,4-phenylene substituted by OCH$_2$COO-lower-alkyl, such as methoxycarbonylmethoxy, and/or T is lower-alkoxy, such as methoxy, ethoxy, isopropoxy, isobutoxy, tert-butoxy or hexyloxy, lower-alkoxy-lower-alkoxy, such as methoxyethoxy, lower-alkenyloxy substituted by COO-lower-alkyl, such as 2-isobutoxycarbonyl-2-pentenyloxy, lower-alkoxy substituted by lower-alkyl-COO, such as pivaloyloxymethoxy, lower-alkyl substituted by lower-alkyl-OCOO, such as 1-isopropoxycarbonyloxy-ethoxy, cycloalkoxy optionally interrupted by O, such as tetrahydropyranyloxy, pyridyl bonded via lower-alkyleneoxy, such as 3- or 4-pyridylmethoxy, or cycloalkyl bonded via lower-alkyleneoxy and optionally interrupted by NCOO-lower-alkyl, such as 1-tert-butoxycarbonyl-3 or 4-piperidylmethoxy. In particular, T may be phenoxyacetate or may be piperinidin-4-yloxyacetate, or may be piperidin-1-carboxylate.

Examples of such compounds of this invention are the following:

ethyl (S)-4-[2-[4-[imino-2-(methoxy-ethoxycarbonylamino)-methyl]-benzoylamino]-propionyl]-phenoxyacetate, ethyl (Z)-(R,S)-4-[2-[4-[amino-hydroxyimino-methyl]-benzoyl-amino]-propionyl]-phenoxyacetate, tetrahydropyran-4-yl (S)-4-[2-[4-(ethoxycarbonylamino-imino-methyl)-benzoylamino]-propionyl]-phenoxyacetate, ethyl (Z)-(R,S)-4-[2-[4-[amino-ethoxycarbonyloximino-methyl]-benzoylamino]-propionyl]-phenoxyacetate, ethyl (S)-4-[2-[4-(imino-phenoxycarbonylamino-methyl)-benzoyl-amino]-propionyl]-phenoxyacetate, 2-methoxy-ethyl (S)-4-[2-[4-[imino-(2-methoxy-ethoxy-carbonyl-amino)-methyl]-benzoylamino]-propionyl]-phenoxyacetate, ethyl (Z)-(S)-4-[2-[4-(amino-hydroxyimino-methyl)-benzoylamino]-propionyl]-phenoxyacetate, isopropyl (E/Z)-(S)-1-[2-[4-(amino-ethoxycarbonylimino-methyl)-benzoylamino]-propionyl]-piperidin-4-yloxyacetate, isopropyl (E/Z)-(S)-1-[2-[4-(amino-hydroxyimino-methyl)-benzoylamino]-propionyl]-piperidin-4-yloxyacetate, isopropyl [1-[4-[4-(ethoxycarbonylamino-imino-methyl)-phenyl]-4-oxo-butyryl]-piperidin-4-yloxy]-acetate, isopropyl (RS)-[1-[4-[4-(isobutoxycarbonylamino-imino-methyl)-phenyl]-2-methyl-4-oxo-butyryl]-piperidin-4-yloxy]-acetate and especially ethyl (E/Z)-(S)-1-[2-[4-(amino-hydroxyimino-methyl)-benzoylamino]-propionyl]-piperidin-4-yloxyacetate as well as the following:

(R/S)-1-isopropoxycarbonyloxy-ethyl (Z)-(S)-[1-[2-[4-(amino-hydroxyimino-methyl)-benzoylamino]-propionyl]-piperidin-4-yloxy]-acetate, pyridin-3-ylmethyl (R)-(E)/(Z)-[1-[4-[4-(amino-hydroxyimino-methyl)-phenyl]-2-methyl-4-oxo-butyryl]-piperidin-4-yloxy]-acetate, pyridin-4-ylmethyl (R)-(E)/(Z)-[1-[4-[4-(amino-hydroxyimino-methyl)-phenyl]-2-methyl-4-oxo-butyryl]-piperidin-4-yloxy]-acetate, tert-butyl (E)- or (Z)-(RS)-3-[1-[(R)-4-[4-(amino-hydroxyimino-methyl)-phenyl]-2-methyl-4-oxo-butyryl]-piperidin-4-yloxyacetoxymethyl]-piperidine-1-carboxylate, ethyl (R)-[1-[4-[4-(benzoyloxymethoxycarbonylamino-imino-methyl)-phenyl]-2-methyl-4-oxo-butyryl]-piperidin-4-yloxy]-acetate, ethyl (R)-[1-[4-[4-(imino-pivaloyloxymethoxycarbonylamino-methyl)-phenyl]-2-methyl-4-oxo-butyryl]-piperidin-4-yloxy]-acetate, tert-butyl (E)- or (Z)-(R)-4-[1-[4-[4-(amino-hydroxyimino-methyl)-phenyl]-2-methyl-4-oxo-butyryl]-piperidin-4-yloxyacetoxymethyl]-piperidine-1-carboxylate, ethyl (S)-[4-[2-[4-[(2-acetoxy-ethoxy-carbonylimino)-amino-methyl]-benzoylamino]-propionyl]-phenoxy]-acetate and acetoxymethyl (S)-4-[2-(4-ethoxycarbonylmethoxy-phenyl)-1-methyl-2-oxo-ethylcarbamoylmethoxy]-piperidine-1-carboxylate.

The following are further examples of compounds of formula I:

cyclopropylmethyl (S)-4-[2-[4-(amino-imino-methyl)-benzoylamino]-propionyl]-phenoxyacetate, cyclohexyl (S)-4-[2-[4-(amino-imino-methyl)-benzoylamino]-propionyl]-phenoxyacetate, ethyl (S)-4-[2-[4-(amino-imino-methyl)-benzoylamino]-3-hydroxy-propionyl]-phenoxyacetate, (S)-4-[2-[4-(amino-imino-methyl)-benzoylamino]-3-(4-methoxy-phenyl)-propionyl]-phenoxyacetic acid, ethyl (2S,3R)-4-[2-[4-(amino-imino-methyl)-benzoylamino]-3-hydroxy-butyryl]-phenoxyacetate, 2-methoxy-ethyl (S)-4-[2-[4-(amino-imino-methyl)-benzoylamino]-propionyl]-phenoxyacetate, ethyl (S)-4-[2-[4-(amino-imino-methyl)-benzoylamino]-3-acetoxy-propionyl]-phenoxyacetate, ethyl (R,S)-4-[2-[4-(ethoxycarbonylamino-imino-methyl)-benzoyl-amino]-3-methylsulphanyl-propionyl]-phenoxyacetate, ethyl (S)-4-[2-[4-(diethoxyphosphorylamino-imino-methyl)-benzoyl-amino]-propionyl]-phenoxyacetate, isopropyl (E/Z)-(S)-1-[2-[4-(amino-ethoxycarbonylimino-methyl)-benzoylamino]-3-(4-ethoxycarbonyloxy-phenyl)-propionyl]-piperidin-4-yloxyacetate, (E/Z)-(S)-4-[2-[4-(amino-ethoxycarbonylimino-methyl)-benzoylamino]-3-(4-isopropoxycarbonylmethoxy-piperidin-1-yl)-3-oxo-propyl]-phenyl 2-amino-benzoate, (E/Z)-(S)-4-[2-[4-(amino-ethoxycarbonylimino-methyl)-benzoylamino]-3-(4-isopropoxycarbonylmethoxy-piperidin-1-yl)-3-oxo-propyl]-phenyl furan-2-carboxylate, (E/Z)-(S)-4-[2-[4-(amino-ethoxycarbonylimino-methyl)-benzoylamino]-3-(4-isopropoxycarbonylmethoxy-piperidin-1-yl)-3-oxo-propyl]-phenyl 2-acetoxy-benzoate, tetrahydropyran-4-yl (S)-1-[2-(5-amino-imino-methyl-pyridin-2-ylcarbonylamino)-propionyl]-piperidin-4-yloxy-acetate and isopropyl (S)-1-[2-(5-aminomethyl-pyridin-2-ylcarbonylamino)-3-(4-methoxy-phenyl)-propionyl]-piperidin-4-yloxyacetate.

The acetic acid derivatives in accordance with the invention can be manufactured by a) cleaving the protected amino or amidino group in a compound of the formula

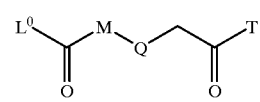

II wherein $L^o$ is a group of one of formulae $L^{10}$ to $L^{50}$

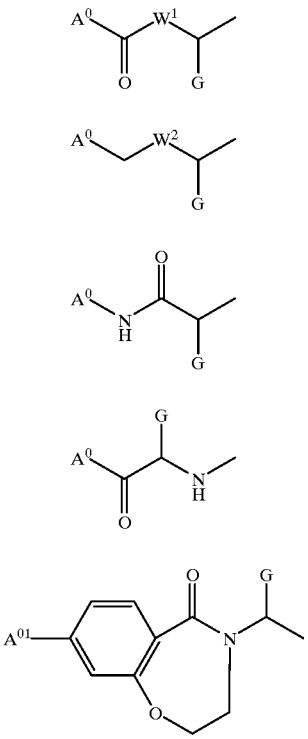

$L^{10}$ $L^{20}$ $L^{30}$ $L^{40}$ $L^{50}$ in which $A^o$ is a group A containing a protected amino or amidino group, A, $W^1$, $W^2$, G, M, Q and T have the above significance and $A^{01}$ is a protected amidino group, or b) converting the free amidino group in a compound of formula III

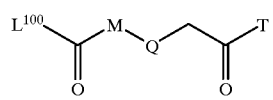

III wherein $L^{100}$ is a group of one of the formulae $L^{101}$ to $L^{501}$

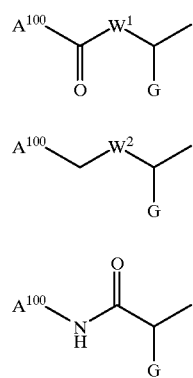

$L^{101}$ $L^{201}$ $L^{301}$

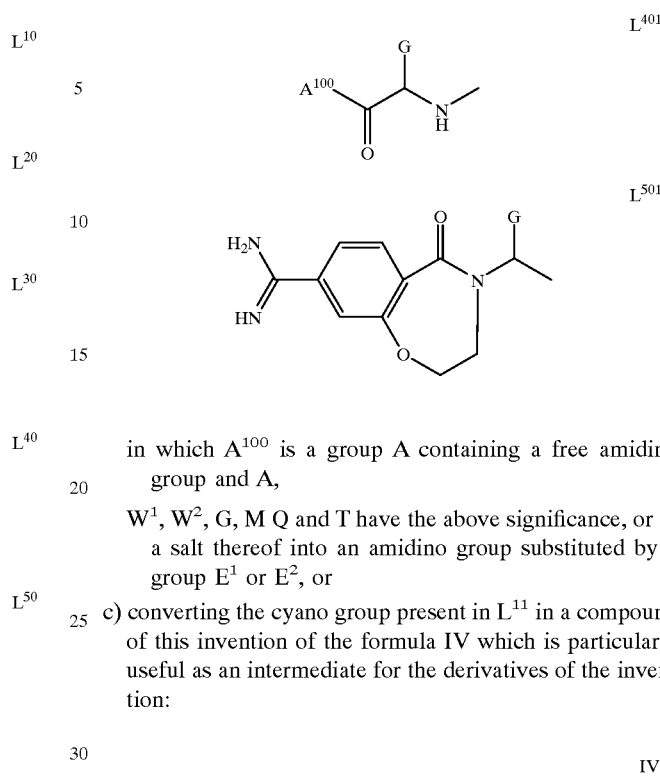

$L^{401}$ $L^{501}$ in which $A^{100}$ is a group A containing a free amidino group and A, $W^1$, $W^2$, G, M Q and T have the above significance, or in a salt thereof into an amidino group substituted by a group $E^1$ or $E^2$, or c) converting the cyano group present in $L^{11}$ in a compound of this invention of the formula IV which is particularly useful as an intermediate for the derivatives of the invention:

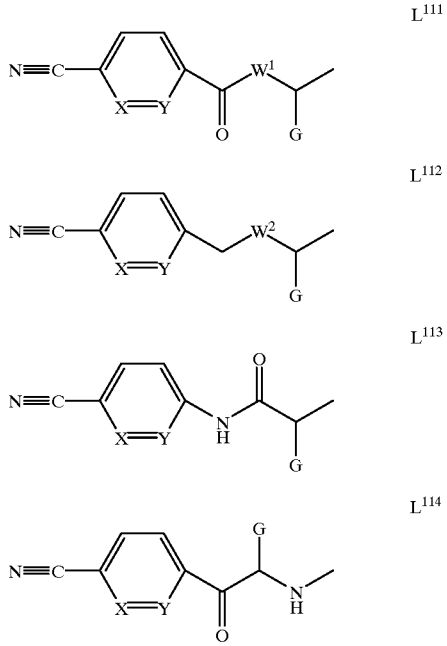

IV wherein $L^{11}$ is a group of one of formulae $L^{111}$ to $L^{115}$ $L^{111}$ $L^{112}$ $L^{113}$ $L^{114}$

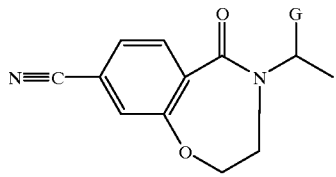

in which X, Y, $W^1$, $W^2$, G, M, Q and T are as defined above for Formula I into an amidino group optionally substituted by $E^1$ or $E^2$, or d) reacting an amine, another intermediate of this invention, of the formula

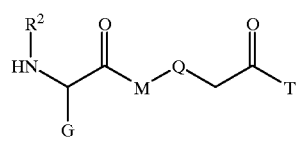

wherein R2 is H, lower-alkyl or lower-alkoxy-lower-alkyl and G, M, Q and T are as defined above for Formula I, with an acid A-COOH or a functional derivative thereof, or e) if desired, functionally modifying a reactive group present in a compound of formula I, and f) if desired, converting a compound of formula I into a physiologically compatible salt or converting a salt of a compound of formula I into the free acid or base.

Examples of cleavable protected amino or amidino groups AO present in compounds II are NH-Boc and NH—Z or C(NH)NH-Boc, C(N-Boc)N(Boc)$_2$, C(N-Boc)NH-Boc und C(NH)NH-Z. Amino and amidino groups protected by Boc can be cleaved e.g. with an acid such as formic acid or trifluoroacetic acid, if desired in a solvent such as dichloromethane, at a temperature up to 40° C., preferably at room temperature. A hydroxy group present in a group $A^o$ can also be protected by a tri-lower-alkyl-silanyl group such as tert-butyl-dimethyl-silanyl. Such groups can be cleaved by means of tetrabutylammonium fluoride in an ether such as diethyl ether and/or THF at a temperature up to 40° C., preferably at room temperature.

The conversion b) of an amidino group present in compound III or a salt thereof, e.g. the trifluoroacetate, into an amidino group substituted by a group $E^1$ or $E^2$ can be carried out in a solvent such as dichloromethane, if desired in the presence of a base such as NaHCO$_3$ or Na$_2$CO$_3$, with a compound of the formula $R^1$OC(O)Cl or ClP(O)(O)-lower-alkyl)$_2$.

In order to convert the cyano group into an amidino group optionally substituted by $E^1$ or $E^2$ according to process variant c), a nitrile of formula IV can be reacted in pyridine and triethylamine with H$_2$S and the resulting compound which is substituted by thiocarbamoyl H$_2$NC(S) can be methylated, e.g. in acetone with methyl iodide at boiling temperature, to the corresponding compound substituted by methylthioformimidoyl HN═C(SCH3). Reaction of the latter compound with a compound E-NH2, wherein E is H, lower-alkyl or lower-alkoxy-lower-alkyl, or with an acid addition salt thereof such as the hydrochloride or the acetate in a solvent such as THF or methanol while heating, conveniently to the boiling point of the reaction mixture, yields the corresponding amidine of formula I. Reaction of a nitrile IV with hydroxylamine hydrochloride in a solvent such as methanol or DMSO in the presence of a base such as sodium methanolate or triethylamine results in the corresponding compound I in which the group A (in L) contains a hydroxylated amidino group.

Reaction d) can be conveniently carried out using a salt, e.g. the hydrochloride, of the amine V in the presence of a base such as pyridine in a solvent such as an ether at a temperature up to 40° C., preferably at room temperature.

A tert-butoxycarbonyl group COOT$^1$ present in an ester of formula I obtained according to variants a) to d) can be cleaved to a corboxy group by means of an acid such as formic acid.

Functional modifications of reactive groups according to process variant e) are (1) the cleavage of lower-alkoxycarbonyl groups such as COOT$^1$; (2) the cleavage of ether groups present e.g. in group G (in L); (3) the conversion of an unsubstituted amidino group ($E^1$=$E^2$=H) present in a group $A^1$ (in L) or $L^5$ into a substituted amidino group; (4) the conversion of a hydroxy group (one of $E^1$ and $E^2$ is OH and the other is H) present in a group $A^1$ (in L) or $L^5$ into a $R^1$OC(O)O group.

These conversions can be carried out in a manner known per se, for example cleavage (1) in a solvent such as an aqueous lower-alkanol, e.g. aqueous methanol or ethanol, with a base such as sodium hydroxide; cleavage (2) of ether groups such as the tert-butoxy group in dichloromethane by means of trifluoroacetic acid; conversions (3) and (4) in a solvent such as dichloromethane in the presence of Na$_2$CO$_3$ by means of a compound of the formula $R^1$OC(O)Cl or in DMF in the presence of triethylamine by means of $R^1$OC(O)O-p-NO$_2$C$_6$H$_5$.

Further modifications such as the esterification of a carboxy group in an acid of formula I (T=OH), the esterification of a hydroxy group present in group G (in L) to an aminobenzoyloxy, furoyloxy, acetoxy or acetoxybenzoyloxy group, the cleavage of the hydroxy group from a hydroxylated amidino group present in group A (in L) and the conversion of a group O═C═ which is not bonded in the form of an amide and which is present in group L and/or between L and M into the HON═C═ group can be carried out in a manner known per se as described in detail in the Examples.

A hydroxylated amidino group present in group A (in L) can be converted into the (5,5-dimethyl or 5-oxo)-4,5-dihydro-1,2,4-oxadiazol-3-yl group in acetone by means of formic acid while heating or in the presence of methylmorpholine in dichloromethane by means of triphosgene while cooling. the conversion of an amidino group present in group A (in L) into an amidino group substituted by —C(O)SR$^1$ can be carried out in dichloromethane in the presence of NaHCO$_3$ by means of the corresponding chlorothioformate ClC(O)SR$^1$.

A N-unsubstituted group $A^3$ or $A^4$, wherein El is H, present in a group of formula L, can be converted firstly by means of acrylonitrile in ethanol into the corresponding N-(2-cyanoethyl) group $A^3$ or $A^4$, wherein $E^1$ stands for 2-cyanoethyl, and the latter group $A^3$ or $A^4$ can be converted in dichloromethane by means of m-chlorobenzoic acid into the corresponding N-hydroxy-substituted group $A^3$ or $A^4$, wherein $E^1$ is OH.

The compounds of formula II can be prepared in a manner known per se. Thus, those wherein L is a N-containing group $L^{10}$ and Q stands for O and of the formula

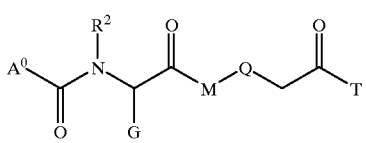

II-A wherein $A^o$, G, M and T have the above significance and $R^2$ is H, lower-alkyl or lower-alkoxy-lower-alkyl, can be prepared starting from compounds of formula VI

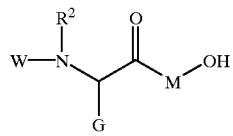

VI wherein W is a protecting group such as Boc and $R^2$, G and M have the above significances, via compounds of the formula

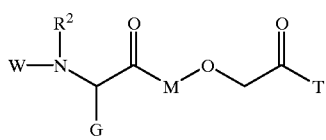

V-A

The reaction VIEV-A can be carried out by means of a bromide $BrCH_2C(O)T$ in the presence of a base such as $K_2CO_3$ in a solvent such as DMF. By cleavage of the protecting group W in the compound of formula V-A there is obtained a compound of formula V. This or an acid addition salt thereof, e.g. the hydrochloride, is then converted into the compound II-A with a functional derivative of an acid $A^oCOOH$, e.g. the acid chloride, in the presence of a base such as N-methylmorpholine in a solvent such as THF.

The compounds VI in which M is optionally substituted 1,4-phenylene are known or can be prepared in a manner known per se, e.g. starting from the compounds VII

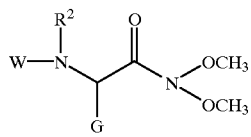

VII via those of formula VI-A

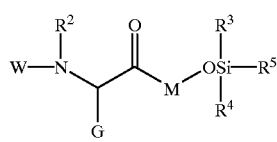

VI-A wherein $R^3$, $R^4$ and $R^5$ are lower-alkyl.

The reaction VII/VI-A can be carried out by means of a bromide $Br-M-OSi(R^3,R^4,R^5)$ in a solvent such as TBF at a low temperature, e.g. −78° C., in the presence of n-butyllithium in hexane. The compound VI is obtained after cleavage of the silanyl group, e.g. in a solvent such as diethyl ether by means of tetrabutylammonium fluoride in THF.

The compounds of formula V-A in which M is 1,4-piperidinylene can be prepared by reacting an acid of formula VIII with an amine of formula IX:

VIII

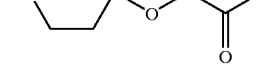

IX

Such compounds V-A can be converted via the compounds V into the corresponding compounds II in which M is 1,4-piperidinylene.

Nitriles of formula IV are obtainable e.g. by reacting compounds of formula V-A (after cleavage of the protecting group W) with an acid chloride

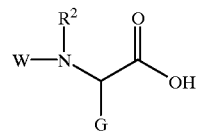

X

Nitriles of formula IV in which M is 1,4-piperidinylene can also be prepared by reacting an acid of the formula $L^{11}$-COOH, which is activated e.g. with 2-chloro-4,6-dimethoxy-1,3,5-triazine and N-methylmorpholine, with an amine of formula IX-A:

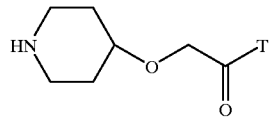

IX-A

A further method for the preparation of the nitrites IV comprises reacting a ketone of formula XI with a bromide of formula XII

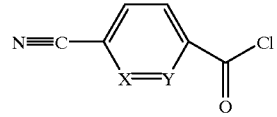

XI

XII wherein $T^2$ is lower-alkyl and X, Y, G, M and $T^1$ have the above significance.

In a variant, an acid chloride of formula X is converted via an ester of formula XI, wherein $T^2$ is tert-butyl, with the bromide XII into a compound of formula XIII:

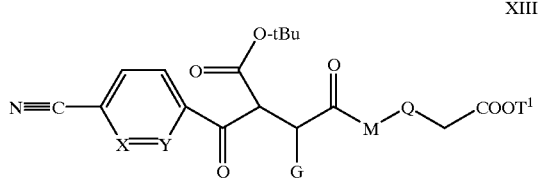

XIII and the t-butoxycarbonyl group is cleaved off from the compound XIII.

Hydrogenation of a nitrile IV in which $W^1$ (in $L^{11}$) is NH, N-lower-alkyl or lower-alkoxy-lower-alkyl-N, e.g. over a Pd/C catalyst in methanol/water/ethyl acetate gives a compound of formula I in which group A (in L) has the formula $A^{01}$

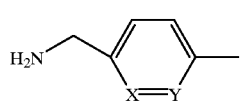

$A^{01}$

The acid starting materials $L^{11}$-COOH which are substituted by cyano in $R^{11}$ are obtainable by a Sandmeyer reaction with the corresponding amino-substituted acid. Acid starting materials of formula $L^{115}$-COOH can be prepared starting from 4-cyanosalicylic acid via compounds of the formula

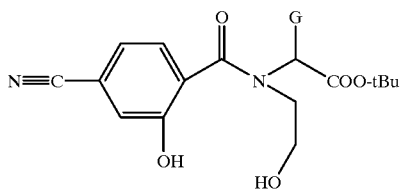

XIV

Moreover, many of the Examples hereinafter contain detailed information concerning the preparation of certain starting materials and intermediates.

The compounds of formula I, their solvates and their salts inhibit not only the binding of fibrinogen, fibronectin and the Willebrand factor to the fibrinogen receptor of blood platelets (glycoprotein IIb/IIIa), but also the binding of these and further adhesive proteins such as vitronectin, collagen and laminin to the corresponding receptors on the surface of the different types of cell. The said compounds therefore influence cell—cell and cell-matrix interactions. In particular, they prevent the formation of blood platelet thrombi and can be used in the control or prevention of illnesses such as thrombosis, stroke, cardiac infarct, inflammation and arteriosclerosis. Further, these compounds have an effect on tumour cells in that they inhibit their metastasis. Accordingly, they can also be used as antitumour agents. Further, they can accelerate wound healing. Since they also prevent bone degradation, they can be used in the treatment of osteoporosis.

The activity of the compounds can be demonstrated as follows:

After oral administration of a compound in accordance with the invention to mice the plasma or a dilution thereof (1 part) is mixed with platelet-rich human plasma (human PRP, 3 parts). The volume of mouse plasma which is required to inhibit by 50% the ADP-induced platelet aggregation in this mixture is determined in an aggregometer. This volume ($IC_{50}$) is divided by the total volume of the mixture and multiplied by the administered dose. The thus-extrapolated $ID_{50}$ values in the following Table correspond to that dose of test substance which must be administered orally in order to inhibit by 50% the ADP-induced ex vivo aggregation of platelets in human PRP.

| Product of Example | 3 | 4 | 9 | 11 | 20 | 22 | 24 | 27 | 28 | 29 |
|---|---|---|---|---|---|---|---|---|---|---|
| $ID_{50}$(mg/kg) | 2.7 | 2.1 | 1.4 | 3.1 | 2.4 | 1.8 | 2.3 | 4.3 | 0.3 | 1.0 |
| Product of Example | 30 | 32 | 33 | 35 | 36 | 38 | 40 | 41 | 49 | 50 |
| $ID_{50}$(mg/kg) | 3.9 | 0.2 | 0.6 | 0.5 | 0.5 | 2.9 | 0.6 | 0.2 | 1.2 | 1.3 |
| Product of Example | 51 | 53 | 60 | 63 | 72 | 76 | 80 | 85 | | |
| $ID_{50}$(mg/kg) | 3.9 | 1.5 | 0.3 | 1.1 | 2.7 | 0.2 | 0.7 | 0.4 | | |

As mentioned earlier, medicaments containing a compound of formula I, a solvate thereof or a salt thereof are also objects of the present invention, as is a process for the production of such medicaments which comprises bringing one or more of the said compounds and, if desired, one or more other therapeutically valuable substances into a galenical administration form. The medicaments can be administered enterally, e.g. orally in the form of tablets, coated tablets, dragées, hard and soft gelatine capsules, solutions, emulsions or suspensions, or rectally, e.g. in the form of suppositories; or as a spray. The administration can, however, also be effected parenterally, e.g. in the form of injection solutions or as an infusion.

The active substance can be mixed with pharmaceutically inert, inorganic or organic excipients for the production of tablets, coated tablets, dragees and hard gelatine capsules. Lactose, corn starch or derivatives thereof, talc, stearic acid or its salts can be used e.g. as such excipients for tablets, dragées and hard gelatine capsules. Suitable excipients for soft gelatine capsules are e.g. vegetable oils, waxes, fats, semi-solid and liquid polyols; depending on the nature of the active substance no excipients are, however, usually required in the case of soft gelatine capsules. Suitable excipients for the manufacture of solutions and syrups are e.g. water, polyols, saccharose, invert sugar and glucose; suitable excipients for injection solutions are e.g. water, alcohols, polyols, glycerol and vegetable oils, and suitable excipients for suppositories are e.g. natural or hardened oils, waxes, fats and semi-liquid or liquid polyols. Moreover, the pharmaceutical preparations can contain preservatives, solubilizers, stabilizers, wetting agents, emulsifiers, sweeteners, colorants, flavorants, salts for varying the osmotic pressure, buffers, coating agents or antioxidants.

For the control or prevention of the illnesses referred to above, the dose of active substance can vary within wide limits and will, of course, be fitted to the individual requirements in each particular case. In general, in the case of oral administration a dose of about 0.1 to 20 mg/kg, preferably of about 0.5 to 4 mg/kg, per day should be appropriate for adults, although the upper limit just given can also be exceeded should this be found to be indicated.

The examples below further describe the invention but are not intended to limit it in any way.

EXAMPLES

Example 1

0.2 ml of iodotrimethylsilane in 2 ml of dichloromethane is added to a solution of 0.5 g of ethyl (S)-4-(2-tert-butoxycarbonylamino-3-phenyl-propionyl)-phenoxyacetate in 2.5 ml of dichloromethane and the mixture is stirred at room temperature for 15 min. The reaction solution is treated with 30 ml of HCl in methanol (4N) and concentrated. The residue is dissolved in 5 ml of pyridine and stirred with 275 mg of p-amidinobenzoyl chloride hydrochloride at room temperature for 24 h. The suspension is suction filtered, the mother liquor is concentrated and the evaporation residue is chromatographed on silylated silica gel RP18 (THF/water gradient). There are obtained 222 mg of methyl (S)-4-[2-[4-(amino-imino-methyl)-benzoylamino]-3-phenyl-propionyl]-phenoxy-acetate hydrochloride, $[\alpha]_D^{20}$=+31.1° (c=1, methanol).

The starting material can be prepared as follows:

a) 29 ml of t-butyllithium (1.4M in pentane) are added to a solution of 11.5 g of p-bromo-tert-butyldimethylsilylphenol in 160 ml of THF at −78° C. with the exclusion of water and the mixture is stirred at −78° C. for 15 min. Subsequently, the solution is treated at −78° C. with 4 g of (S)-2-tert butoxycarbonylamino-N-methoxy-N-methyl-3-phenylpropionamide in 40 ml of THF, stirred at −78° C. for 1 h. and poured into 300 ml of 1M phosphoric acid. The aqueous phase is extracted with ether, the ether phases are washed with sat. NaCl solution, dried and concentrated. After chromatography of the evaporation residue on silica gel (hexane ethyl acetate 9:1) there are obtained 2.95 g of tert-butyl (S)-[1-benzyl-2-(4-tert-butyl-dimethyl-silanyloxy-phenyl)-2-oxo-ethyl]-carbamate as a colourless oil, $[\alpha]_D^{20}$=+40.30 (c=0.8, chloroform).

b) A solution of 2.24 g of the product from a) in 30 ml of THF is stirred at room temperature for 16 h. with 0.75 g of caesium fluoride in 2.5 ml of water and the mixture is concentrated. Chromatography of the residue on silica gel (hexane/ethyl acetate 2:1) gives 2.47 g of tert butyl (S)-[1-benzyl-2-(4-hydroxy-phenyl)-2-oxo-ethyl]-carbamate, $[\alpha]_D^{20}$=+67.0° (c=0.7, chloroform).

c) A suspension of 2.44 g of the product from b), 2.39 g of ethyl bromoacetate and 2.97 g of potassium carbonate in 20 ml of DMF is stirred at room temperature for 4 h., the precipitate is filtered off under suction and the mother liquor is concentrated. Chromatography of the residue on silica gel (hexane/ethyl acetate 5:1) gives 7.44 g of ethyl (S)-4-(2-tert-butoxycarbonylamino-3-phenyl-propionyl)-phenoxy acetate, $[\alpha]_D^{20}$=+40.6° (c=1, chloroform).

Example 2

A solution of 263 mg of 2-methoxy-ethyl 4-tert-butoxy-carbonylaminoacetyl-phenoxyacetate in 10 ml of dichloromethane and 5 ml of trifluoroacetic acid is stirred at room temperature for 2 h. and concentrated. The residue is suspended in ether, the crystals are filtered off under suction, dissolved in 5 ml of pyridine and stirred at room temperature with 219 mg of amidinobenzoyl chloride hydrochloride for 18 h. Concentration of the reaction solution and chromatography of the residue on silylated silica gel RP18 (THF/water gradient) gives 35 mg of 2-methoxy-ethyl 4-[4-(amino-imino-methyl)-benzoylaminoacetyl]-phenoxyacetate, MS (EI): 414 (M+H)⁺.

The starting material can be prepared as follows:
a) A suspension of 476 mg of tert-butyl (R,S)-2-hydroxy-2-(4-hydroxyphenyl)-ethylcarbamate, 287 mg of (2-methoxy-ethyl)chloroacetate and 260 mg of potassium carbonate in 13 ml of DMF is stirred at 50° C. for 2 h., cooled to room temperature and diluted with 100 ml of water. The aqueous phase is extracted with ether, the ether phases are washed with sat. NaCl solution, dried and concentrated. Chromatography of the residue on silica gel (hexane/ethyl acetate 1:2) gives 349 mg of 2-methoxy-ethyl (R,S)-4-(2-tert-butoxycarbonylamino-1-hydroxy-ethyl)-phenoxyacetate, MS (EI): 312 (M-57).

b) Oxidation of 316 mg of the product from a) in 10 ml of dichloromethane with 224 mg of pyridine chlorochromate for 3 h. at room temperature gives, after concentration of the reaction solution and chromatography of the residue on silica gel (hexane/ethyl acetate 1:1, 1:2) 284 mg of 2-methoxy-ethyl 4-tert-butoxycarbonylaminoacetyl-phenoxyacetate, MS (EI): 294 (M-73).

Example 3

A solution of 550 mg of cyclopropylmethyl (S)-4-(2-tert-butoxycarbonylamino-propionyl)-phenoxyacetate in 10 ml of dichloromethane is stirred at 0° C. with 0.2 ml of trimethylsilyl iodide for 15 min., treated with 0.5 ml of HCl in dioxan (4M) and concentrated. The residue is reacted with 330 mg of p-amidinobenzoyl chloride hydrochloride analogously to Example 1. After chromatography of the crude product on silylated silica gel RP18 (THF/water gradient) there are obtained 313 mg of cyclopropylmethyl (S)-4-[2-[4-(amino-imino-methyl)-benzoylamino]-propionyl]-phenoxyacetate hydrochloride (1:0.4) hydroiodide (1:0.6), m.p. 125° C., $[\alpha]_D^{20}$=+56.6° (c=0.5, DMSO).

The starting material can be prepared as follows:
a) 94 ml of n-butyllithium (1.6M in hexane) are added dropwise to a solution of 43.05 g of p-bromo-tert-butyldimethylsilyl phenol in 150 ml of THF at −78° C. with the exclusion of moisture and the mixture is stirred at −78° C. for 15 min. Subsequently, 11.61 g of (S)-2-tert-butoxycarbonylamino-N-methoxy-N-methyl-propionamide in 150 ml of THF are added at −78° C. in 30 min., stirred at −78° C. for 0.5 h. and the reaction solution is poured into 400 ml of 1M phosphoric acid. The aqueous phase is extracted with ether, the ether phases are washed with sat. NaCl solution, dried and concentrated. After chromatography of the evaporation residue on silica gel (hexane/ethyl acetate 9:1) there are obtained 17.85 g of tert-butyl (S)-1-(4-tert-butyl-dimethyl-silanyloxy-benzoyl)-ethylcarbamate as a colourless oil, Rf=0.43 (hexane/ethyl 5:1).

b) 47 ml of tetrabutylammonium fluoride (1M in THF) are added to a solution of 17.85 g of the product from a) in 180 ml of ether and stirred at room temperature for 1 h. The reaction solution is extracted with 1M phosphoric acid, washed with sat. NaCl solution, dried and concentrated. There are obtained 12.03 g of (S)-1-(4-hydroxy-benzoyl)-ethylcarbamate, m.p. 166–168° C., $[\alpha]_D^{20}$=+24.9° (c=1, chloroform).

c) Reaction of 400 mg of the product from b) with cyclopropylmethyl bromoacetate analogously to Example 1c gives, after chromatography on silica gel (hexane ethyl acetate 3:1), 580 mg of cyclopropylmethyl (S)-4-(2-tert-butoxycarbonylamino-propionyl)-phenoxyacetate $[\alpha]_D^{20}$=+12.4° (c=0.9, chloroform).

Example 4

Analogously to Example 3, 500 mg of cyclohexyl (S)-4-(2-tert-butoxycarbonylamino-propionyl)-phenoxyacetate are reacted with 0.17 ml of trimethylsilyl iodide and subsequently with 320 mg of p-amidinobenzoyl chloride hydrochloride and give, after chromatography on silylated silica gel RP18 (THF/water gradient), 330 mg of cyclohexyl (S)-4-[2-[4-(amino-imino-methyl)-benzoylamino]-propionyl]-phenoxyacetate hydrochloride (1:0,6) hydroiodide (1:0.4), m.p. 110° C., $[\alpha]_D^{20}$=+56.7° (c=0.55, DMSO).

The starting material can be prepared as follows:

Reaction of 530 mg of tert-butyl (S)-1-(4-hydroxy-benzoyl)-ethylcarbamate with 660 mg of cyclohexyl bromoacetate analogously to Example 1c gives, after chromatography on silica gel (hexane ethyl acetate 5:1), 735 mg of cyclohexyl (S)-4-(2-tert-butoxycarbonylamino-propionyl)-phenoxyacetate, $[\alpha]_D^{20}$=+12.0° (c=0.5, chloroform).

Example 5

As in Example 3, 680 mg of tetrahydropyran-4-yl (S)-4-(2-tert-butoxycarbonylamino-propionyl)-phenoxyacetate are reacted with 1.7 ml of trimethylsilyl iodide (1M in dichloromethane) and subsequently with 438 mg of p-amidinobenzoyl chloride hydrochloride and give, after chromatography on silylated silica gel RP18 (THF/water gradient), 430 mg of tetrahydropyran-4-yl (S)-4-[2-[4-(amino-imino-methyl)-benzoylamino]-propionyl]-phenoxyacetate hydrochloride (1:0.8) hydroiodide (1:0.4), $[\alpha]_D^{20}$=+50.3° (c=1, dimethyl sulphoxide).

The starting material can be prepared as follows:
a) Reaction of 530 mg of tert-butyl (S)-1-(4-hydroxy-benzoyl)-ethylcarbamate with 670 mg of 4-tetrahydropyranyl bromoacetate analogously to Example 1c gives, after chromatography on silica gel (hexane/ethyl acetate 2:1), 736 mg of tetrahydropyran-4-yl (S)-4-(2-tert-butoxycarbonylamino-propionyl)-phenoxyacetate, $[\alpha]_D^{20}$=+11.1° (c=0.7, chloroform).

Example 6

A solution of 120 mg of methyl (S)-4-[2-[4-(amino-imino-methyl)-benzoyl-amino]-3-phenyl-propionyl]-phenoxyacetate hydrochloride and 80 mg of sodium hydroxide in 20 ml of methanol and 5 ml of water is stirred at room temperature for 1 h. 15 min., acidified with 1N HCl and concentrated. Chromatography of the residue on silylated silica gel RP18 (THF/water gradient) gives 60 mg of (S)-4-[2-[4-(amino-imino-methyl)-benzoylamino]-3-phenyl-propionyl]-phenoxyacetic acid, m.p. >200° C., MS (ISP): 446 (M+H)$^+$.

Example 7

Reaction of 800 mg of ethyl 4-[(S)-3-tert-butoxy-2-tert-butoxycarbonylamino-propionyl]-phenoxyacetate with 450 mg of trimethylsilyl iodide and 497 mg of p-amidinobenzoyl chloride hydrochloride analogously to Example 3 gives, after chromatography on silylated silica gel RP18 (THF/water gradient), 540 mg of ethyl 4-(S)-2-[4-(amino-imino-methyl)-benzoylamino]-3-tert-butoxy-propionyl]-phenoxyacetate hydrochloride (1:0.5) hydroiodide (1:0.4), m.p. 144° C., $[\alpha]_D^{20}$=+34.2° (c=0.5, DMSO).

The starting material can be prepared as follows:
a) A suspension of 10 g of N-tert-butoxycarbonyl-O-tert-butyl-L-serine dicyclohexylammonium salt in 100 ml of THF is stirred at room temperature with 5.5 ml N-methylmorpholine, 10.3 g of HBTU and 2.2 g of N,O-dimethylhydroxylamine hydrochloride for 21 h. and concentrated. Chromatography of the residue on silica gel (hexane/ethyl acetate 1:1) gives 6.02 g of tert-butyl (S)-2-tert-butoxy-1-(N-methoxy-N-methyl-carbamoyl)-ethylcarbamate $[\alpha]_D^{20}$=+18.6° (c=0.65, chloroform).

b) A solution of 3.7 g of the product from a) is reacted analogously to Example 3a with 7.82 g of p-bromo-tert-butyldimethylsilylphenol and 26 ml of tert-butyllithium (1.4M in pentane). Chromatography of the residue on silica gel (hexane/ethyl acetate 5:1) gives 3.58 g of tert-butyl (S)-2-tert-butoxy-1-(4-tert-butyl-dimethyl-silanyloxy-benzoyl)-ethylcarbamate, $[\alpha]_D^{20}$=+28.3° (c=0.6, chloroform).
c) Cleavage of the silyl protecting group from 2.5 g of the product from b) with 840 mg of caesium fluoride is effected according to Example 1b. After chromatography on silica gel (hexane/ethyl acetate 3:1 there are obtained 1.08 g of tert-butyl (S)-2-tert-butoxy-1-(4-hydroxy-benzoyl)-ethylcarbamate, $[\alpha]_D^{20}$=+41.5° (c=1, chloroform).
d) Reaction of 1 g of the product from c) with 0.5 ml of ethyl bromoacetate and 1.23 g of potassium carbonate analogously to Example 1c gives, after chromatography on silica gel (hexane/ethyl acetate 3:1), 1.19 g of ethyl 4-[(S)-3-tert-butoxy-2-tert-butoxycarbonylamino-propionyl]-phenoxyacetate, $[\alpha]_D^{20}$=+27.3° (c=0.8, chloroform).

Example 8

Analogously to Example 3, 778 mg of ethyl (S)-4-[2-tert-butoxycarbonylamino-3-(4-methoxy-phenyl)-propionyl]-phenoxyacetate are reacted with 0.28 ml of trimethylsilyl iodide and 450 mg of p-amidinobenzoyl chloride and the crude product is chromatographed on silylated silica gel RP18 (THIF/water gradient). There are obtained 272 mg of ethyl (S)-4-[2-[4-(amino-imino-methyl)-benzoylamino]-3-(4-methoxy-phenyl)-propionyl]-phenoxyacetate hydrochloride (1:0.3) hydroiodide (1:0.3), m.p. 129° C., $[\alpha]_D^{20}$=+20.0° (c=0.6, DMSO).

The starting material can be prepared as follows:
a) Reaction of 3.5 g of tert-butyl (S)-1-(N-methoxy-N-methyl-carbamoyl)-2-(4-methoxy-phenyl)-ethylcarbamate with 8.9 g of p-bromo-tert-butyldimethylsilylphenol and 22.2 ml of tert-butyllithium (1.4M in pentane) according to Example 3a and chromatography of the evaporation residue on silica gel (hexane/ethyl acetate 5:1) gives 3.66 g of (S)-1-[4-(tert-butyl-dimethyl-silanyloxy)-benzoyl]-2-(4-methoxy-phenyl)-ethylcarbamate, $[\alpha]_D^{20}$=+23.8° (c=0.5, chloroform).
b) A solution of 2.5g of the product from a) is deprotected as described in Example 3b). After chromatography on silica gel (hexane/ethyl acetate 3:1, 2:1) there are obtained 1.42 g of tert-butyl (S)-1-(4-hydroxy-benzoyl)-2-(4-methoxy-phenyl)-ethylcarbamate, m.p. 133–135° C., $[\alpha]_D^{20}$=+47.3° (c=0.9, chloroform).
c) Reaction of 1.0 g of the preceding step product with ethyl bromoacetate according to Example 1c) and chromatography of the residue on silica gel (hexane/ethyl acetate 2:1) gives 1.21 g of ethyl (S)-4-[2-tert-butoxycarbonylamino-3-(4-methoxy-phenyl)-propionyl]-phenoxyacetate, m.p. 95–97° C., $[\alpha]_D^{20}$=+22.6° (c=0.5, chloroform).

Example 9

A solution of 300 mg of ethyl (S)-$^4$-[2-[4-(amino-imino-methyl)-benzoylamino]-3-tert-butoxy-propionyl]-phenoxyacetate hydrochloride (1:0.5) hydroiodide (1:0.4) in 3 ml of dichloromethane is treated with 1 ml of trifluoro-acetic acid, stirred at room temperature for 4 h. and concentrated. Chromatography of the residue on silica gel (chloroform/ethanol/water 60:30:5) gives 100 mg of ethyl (S)-4-[2-[4-(amino-imino-methyl)-benzoylamino]-3-hydroxy-propionyl]-phenoxyacetate trifluoroacetate, $[\alpha]_D^{20}$=+52.0° (c=0.3, dimethyl sulphoxide).

Example 10

A solution of 260 mg of ethyl (S)-4-[2-(4-tert-butoxy-carbonylaminomethyl-benzoylamino)-propionyl]-phenoxyacetate in 3 ml of dichloromethane and. 1.5 ml of trifluoroacetic acid is stirred at room temperature for 1 h. and concentrated. The residue corresponds to 260 mg of ethyl (S)-4-[2-(4-aminomethyl-benzoylamino)-propionyl]-phenoxyacetate, $[\alpha]_D^{20}$=+43.0° (c=0.3, DMSO).

The starting material can be prepared as follows:
a) Reaction of 530 mg of tert-butyl (S)-1-(4-hydroxy-benzoyl)-ethylcarbamate with ethyl bromoacetate analogously to Example 1c) gives, after chromatography on silica gel (hexane/ethyl acetate 5:1), 582 mg of ethyl (S)-4-(2-tert-butoxycarbonylamino-propionyl)-phenoxyacetate, $[\alpha]_D^{20}$=–1.8° (c=0.5, ethanol).
b) Deprotection of 620 mg of the product from a) analogously to Example 3 gives ethyl (S)-4-(2-amino-propionyl)-phenoxyacetate hydrochloride which is reacted further as the crude product. A solution of 443 mg of 4-tert-butoxycarbonylaminomethyl-benzoic acid and 0.43 ml of N-methylmorpholine in 5 ml of THF is treated with 800 mg of HBTU at 0° C., stirred at 0° C. for 1 h. and subsequently added to 0.3 ml of N-methylmorpholine and the aforementioned ethyl (S)-4-(2-amino-propionyl)-phenoxyacetate dissolved in 6 ml of THF. After stirring at room temperature for 3.5 h. the solution is concentrated and the residue is chromatographed on silica gel (hexane/ethyl acetate 1:1). There are obtained 463 mg of ethyl (S)-4-[2-(4-tert-butoxycarbonylaminomethyl-benzoylamino)-propionyl]-phenoxyacetate, $[\alpha]_D^{20}$=+50.0° (c=0.5, chloroform).

Example 11

A solution of 630 mg of ethyl (S)-4-[2-[4-(amino-imino-methyl)-benzoylamino]-3-(4-methoxy-phenyl)-propionyl]-phenoxyacetate hydrochloride (1:0.3) hydroiodide (1:0.3) (Example 8) and 330 mg of sodium hydroxide in 15 ml of water and 30 ml of ethanol is stirred at room temperature for 3 h. and subsequently concentrated. After chromatography on silylated silica gel RP18 (THF/water gradient) there are obtained 32 mg of (S)-4-[2-[4-(amino-imino-methyl)-benzoylamino]-3-(4-methoxy-phenyl)-propionyl]-phenoxyacetic acid, microanalysis: calc. C 65.68, H 5.30, N 8.84; found C 65.77, H 5.12, N 8.73.

Reference Example 12

A solution of 1 g of ethyl (S)-4-[2-[4-(tert-butoxycarbonylamino-imino-methyl)-benzoylamino]-3-methyl-butyryl]-phenoxyacetate in 10 ml of dichloromethane and 5 ml of trifluoroacetic acid is stirred at room temperature for 3 h. and concentrated. Chromatography on silylated silica gel RP18 (THF/water gradient) gives 789 mg of ethyl (S)-4-[2-[4-(amino-imino-methyl)-benzoylamino]-3-methyl-butyryl]-phenoxyacetate trifluoroacetate m.p. 202° C., $[\alpha]_D^{20}$=+95.5° (c=1, DMSO).

The starting material can be prepared as follows:
a) 2.6 g of (S)-2-tert-butoxycarbonylamino-N-methoxy-N,3-dimethyl-butyramide are reacted with 8.6 g of p-bromo-tert-butyldimethylsilylphenol analogously to Example 3a). After chromatography on 200 g of silica gel (hexane/ethyl acetate 95:5) there are obtained 3.0 g of tert-butyl (S)-1-(4-tert-butyl-dimethyl-silanyloxy-benzoyl)-2-methyl-propylcarbamate, $[\alpha]_D^{20}$=+83.0° (c=0.5, chloroform).
b) Cleavage of the protecting group from 3.0 g of the product from a) analogously to Example 3b) gives 1.88 g of tert-butyl (S)-1-(4-hydroxy-benzoyl)-2-methyl-propylcarbamate, $[\alpha]_D^{20}$=+107.9° (c=0.7, chloroform).
c) Reaction of 1.88 g of the product from b) with ethyl bromoacetate as in Example 1 c and subsequent chromatography on silica gel (hexane/ethyl acetate 5:1) gives 2.02 g of ethyl (S)-4-(2-tert-butoxycarbonylamino-3-methyl-butyryl)-phenoxyacetate, $[\alpha]_D^{20}$=+86.1° (c=1, chloroform).
d) 13.96 g of di-tert-butyl dicarbonate in 70 ml of dioxan are added at 0° C. to a suspension of 7 g of 4-amidinobenzoic acid in 120 ml of dioxan and 88 ml of 1N NaOH and the mixture is subsequently stirred at room temperature for 1.5 h. The precipitate is filtered off under suction, the mother liquor is extracted twice with 100 ml of ether, adjusted to pH 6 with 1N HCl and concentrated. Chromatography of the residue on silylated silica gel RP18 (THF/water gradient) gives 4.2 g of N-tert-butoxycarbonyl-4-amidinobenzoic acid, m.p. >200° C.
e) 410 ml of trimethylsilyl iodide are added to a solution of 1.14 g of ethyl (S)-4-(2-tert-butoxycarbonylamino-3-methyl-butyryl)-phenoxyacetate in 10 ml of anhydrous dichloromethane at 0° C., stirred at 0° C. for 15 min., the yellow solution is treated with 1.5 ml of HCl in dioxan (4N) and the solvent is subsequently evaporated. The residue is dissolved in 10 ml of THF, treated with 793 mg of N-tert-butoxycarbonyl-4-amidinobenzoic acid, 1.0 ml of triethylamine and 1.33 g of HBTU and stirred at room temperature for 16 h. The resulting suspension is concentrated and the residue is chromatographed on silica gel. There are obtained 1.07 g of ethyl (S)-4-[2-[4-(tert-butoxycarbonylamino-imino-methyl)-benzoylamino]-3-methyl-butyryl]-phenoxyacetate, MS (ISP): 526 (M+H)⁺.

Example 13

In analogy to Example 12, from 250 mg of ethyl (S)-4-[2-[4-(tert-butoxycarbonylamino-imino-methyl)-benzoylamino]-3-[4-(2-methoxy-ethoxy)-phenyl]-propionyl]-phenoxyacetate and chromatography on silylated silica gel RP18 (THF/water gradient) there are obtained 66 mg of ethyl (S)-4-[2-[4-(amino-imino-methyl)-benzoylamino]-3-[4-(2-methoxy-ethoxy)-phenyl]-propionyl]-phenoxyacetate trifluoroacetate, MS (ISP): 548 (M+H)⁺

The starting material can be prepared as follows:
a) The phase transfer reaction of 2.2 g of tert-butyl (S)-2-(4-hydroxy-phenyl)-1-(methoxy-methyl-carbamoyl)-ethylcarbamate with 2.5 g of 2-chloroethyl methyl ether in 10 ml of toluene and 10 ml of 50% NaOH in the presence of 50 mg of tetrabutylammonium hydrogen sulphate has finished after 1 h. The aqueous phase is extracted with ether, the combined organic phases are washed with saturated NaCl solution, dried and concentrated. Chromatography of the residue on silica gel gives 1.11 g of tert-butyl (S)-2-[4-(2-methoxy-ethoxy)-phenyl]-1-(methoxy-methyl-carbamoyl)-ethylcarbamate, $[\alpha]_D^{20}$=+17.6° (c=1, chloroform).
b) By reacting 1 g of the preceding step product according to Example 3a there are obtained, after chromatography on silica gel (hexane/ethyl acetate 9:1), 326 mg of tert-butyl (S)-1-[4-(tert-butyl-dimethyl-silanyloxy)-benzoyl]-2-[4-(2-methoxy-ethoxy)-phenyl]-ethylcarbamate, MS (ISP): 530 (M+H)⁺.
c) By reacting 310 mg of the product from b) as in Example 3b and alkylating the product analogously to Example 1c there are obtained, after chromatography on silica gel (hexane/ethyl acetate 2:1), 273 mg of ethyl (S)-4-[2-tert-butoxycarbonylamino-3-[4-(2-methoxy-ethoxy)-phenyl]-propionyl]-phenoxyacetate, MS (ISP): 502 (M+H)+.
d) Reaction of 250mg of the preceding step product according to Example 12e leads, after chromatography on silica gel (hexane/ethyl acetate 1:2), to 267 mg of ethyl (S)-4-[2-[4-(tert-butoxycarbonylamino-imino-methyl)-benzoylamino]-3-[4-(2-methoxy-ethoxy)-phenyl]-propionyl]-phenoxyacetate, MS (ISP): 648 (M+H)+.

Reference Example 14

A solution of 400 mg of ethyl (S)-4-[2-[4-(amino-imino-methyl)-benzoylamino]-3-methyl-butyryl]-phenoxyacetate trifluoroacetate (Example 12) in 65 ml of ethanol and 17 ml of water is treated with 200 mg of NaOH, stirred at room temperature for 1 h., acidified with 7 ml of 1N HCl and concentrated. After chromatography on silylated silica gel RP18 (THF/water gradient) the residue gives 287 mg of (S)-4-[2-[4-(amino-imino-methyl)-benzoylamino]-3-methyl-butyryl]-phenoxyacetic acid hydrochloride (1:0.4), MS (ISP): 398 (M+H)+.

Example 15

66 mg of 2-methoxy-ethyl chloroformate are added to a suspension of 250 mg of ethyl (S)-4-[2-[4-(amino-imino-methyl)-benzoylamino]-3-hydroxy-propionyl]-phenoxyacetate trifluoroacetate in 4 ml of dichloromethane and 4 ml of saturated $Na_2CO_3$ solution and the mixture is subsequently stirred at room temperature for 5 min. The aqueous phase is extracted with dichloromethane, the dichloromethane phases are washed with water, dried and concentrated. After chromatography of the residue on silica gel (ethyl acetate) there are obtained 55 mg of ethyl (S)-4-[3-hydroxy-2-[4-[imino-(2-methoxy-ethoxycarbonylamino)-methyl]-benzoyl-amino]-propionyl]-phenoxyacetate, MS (ISP): 516 (M+H)+.

Example 16

A solution of 200 mg of tert-butyl (S)-4-[3-tert-butoxy-2-[4-tert-butoxycarbonylamino-imino-methyl)-benzoylamino]-propionyl]-phenoxyacetate in 2 ml of dichloromethane and 1 ml of trifluoroacetic acid is stirred at room temperature for 2 h. and concentrated. The residue is suspended in methanol, centrifuged off and washed with ether. There are obtained 41 mg of (S)-4-[2-[4-(amino-imino-methyl)-benzoylamino]-3-hydroxy-propionyl]-phenoxyacetic acid trifluoroacetate, MS (ISN): 384 (M–H)−.

The starting material can be prepared as follows:
a) Reaction of 1.35 g of tert-butyl (S)-2-tert-butoxy-1-(4-hydroxy-benzoyl)-ethylcarbamate with tert-butyl bromoacetate analogously to Example 1c gives 417 mg 1.19 g of tert-butyl (S)-4-(2-tert-butoxycarbonylamino-3-tert-butoxy-propionyl)-phenoxyacetate, (ISN): 450 (M–H)−.
b) Reaction of 400 mg of the preceding step product with N-tert-butoxycarbonyl-4-amidinobenzoic acid as in Example 12a gives, after chromatography on silica gel (hexane/ethyl acetate 1:1), 230 mg of ttertbutyl (S)-4-[3-tert-butoxy-2-[4-(tert-butoxycarbonylamino-imino-methyl)-benzoylamino]-propionyl]-phenoxyacetate, MS (ISN): 596 (M–H)−.

Example 17

Reaction of 100 mg of ethyl (S)-4-[2-[4-(amino-imino-methyl)-benzoylamino]-3-hydroxy-propionyl]-phenoxyacetate trifluoroacetate (Example 9) with 54 ml of isobutyl chloroformate as in Example 15 gives, after chromatography (ethyl acetate), 65 mg of ethyl (S)-4-[3-hydroxy-2-[4-(imino-isobutoxycarbonylamino-methyl)-benzoylamino]-propionyl]-phenoxyacetate, $[\alpha]_D^{20}$=+47.0° (c=0.7, DMSO).

Example 18

By reaction of 170 mg of ethyl (S)-4-[2-[4-(tert-butoxycarbonylamino-imino-methyl)-benzoylamino]-3-methoxy-propionyl]-phenoxyacetate with trifluoroacetic acid as in Example 12 and crystallization of the residue with ether there are obtained 124 mg of ethyl (S)-4-[2-[4-(amino-imino-methyl)-benzoylamino]-3-methoxy-propionyl]-phenoxyacetate trifluoroacetate, MS (ISP): 428 (M+H)+.

The starting material can be prepared as follows:
a) Reaction of 1.18 g of (S)-2-tert-butoxycarbonylamino-N,3-dimethoxy-N-methyl-propionamide with p-bromo-tert-butyl-dimethylsilylphenol analogously to Example 3a gives, after chromatography on silica gel (hexane/ethyl acetate 8:1), 872 mg of tert-butyl (S)-1-[4-(tert-butyl-dimethyl-silanyloxy)-benzoyl]-2-methoxy-ethylcarbamate, MS (ISP): 410 (M+H)+.
b) Cleavage of the silyl protecting group from 850 mg of the preceding step product according to Example 3b and alkylation of the product according to Example lc leads to 546 mg of ethyl (S)4-(2-tert-butoxycarbonylamino-3-methoxy-propionyl)-phenoxyacetate, MS (EI): 308 (M-73).
c) Reaction of 530 mg of the preceding step product with N-tert-butoxycarbonyl-4-amidinobenzoic acid according to the procedure of Example 12e and chromatography on silica gel (hexane/ethyl acetate 1:2) gives 170 mg of ethyl (S)-4-[2-[4-(tert-butoxycarbonylamino-imino-methyl)-benzoylamino]-3-methoxy-propionyl]-phenoxyacetate, MS (ISP): 528 (M+H)+.

Example 19

From 510 mg of (S)-sec-butyl (S)-4-[3-tert-butoxy-2-[4-(tert-butoxycarbonylamino-imino-methyl)-benzoylamino]-propionyl]-phenoxy-acetate there are obtained according to Example 12 and after chromatography of the crude product on silylated silica gel RP18 (THF/water gradient) 280 mg of (S)-sec-butyl (S)-4-[2-[4-(amino-imino-methyl)-benzoylamino]-3-hydroxy-propionyl]-phenoxyacetate trifluoroacetate, m.p. 85–87° C., $[\alpha]_D^{20}$=+55.7° (c=0.3, dimethyl sulphoxide).

The starting material can be prepared as follows:
a) From 790 mg of tert-butyl (S)-2-tert-butoxy-1-(4-hydroxy-benzoyl)-ethylcarbamate there are obtained with (S)-sec-butyl bromoacetate according to Example 1c and after chromatography on silica gel (hexane/ethyl acetate 9:1) 780 mg of (S)-sec-butyl (S)-4-(3-tert-butoxy-2-tert-butoxycarbonylamino-propionyl)-phenoxyacetate, $[\alpha]_D^{20}$=+35.3° (c=0.45, chloroform).
b) Reaction of 720 mg of the preceding step product with 510 mg of N-tert-butoxycarbonyl-4-amidinobenzoic acid analogously to Example 12e gives, after chromatography on silica gel (hexane/ethyl acetate (3:1, 2:1), 570 mg of (S)-sec-butyl (S)-4-[3-tert-butoxy-2-[4-(tert-butoxycarbonylamino-imino-methyl)-benzoylamino]-propionyl]-phenoxy-acetate, $[\alpha]_D^{20}$=+51.3° (c=1, chloroform).

Example 20

From 650 mg of ethyl (2S,3R)-4-[3-tert-butoxy-2-[4-(tert-butoxycarbonylamino-imino-methyl)-benzoylamino]- butyryl]-phenoxy-acetate there are obtained according to Example 12 and after chromatography on silylated silica gel RP18 (THF/water gradient) 350 mg of ethyl (2S,3R)-4-[2-[4-(amino-imino-methyl)-benzoylamino]-3-hydroxy-butyryl]-phenoxyacetate trifluoroacetate, m.p. 95–97° C., $[\alpha]_D^{20}$=+98.8° (c=0.4, DMSO).

The starting material can be prepared as follows:
a) From 15 g of tert-butyl (1S,2R)-2-tert-butoxy-1-carboxy-propylcarbamate there are obtained in analogy to Example 7a, after chromatography on silica gel (hexane/ ethyl acetate 5:1, 3:1), 11.19 g of tert-butyl (1S ,2R)-2-tert-butoxy-1-(methoxy-methyl-carbamoyl)-propylcarbamate, $[\alpha]_D^{20}$=+30.0° (c=0.7, chloroform).
b) Reaction of 17 g of the preceding step product with p-bromo-tert-butyldimethylsilylphenol analogously to Example 3a gives, after chromatography on silica gel (hexane/ethyl acetate 9:1), 4.76 g of tert-butyl (1S,2R)-2-tert-butoxy-1-[4-(tert-butyl-dimethyl-silanyloxy)-benzoyl]-propylcarbamate, $[\alpha]_D^{20}$=+61.0° (c=0.3, chloroform).
c) Cleavage of the silyl protecting group from 4.74 g of the preceding step product according to Example 3b and alkylation of the product according to Example 1c leads, after chromatography on silica gel (hexane/ethyl acetate 5:1), to 3.34 g of ethyl (2S,3R)4-(3-tert-butoxy-2-tert-butoxycarbonylamino-butyryl)-phenoxyacetate, $[\alpha]_D^{20}$=+71.0° (c=0.3, chloroform).
d) Reaction of 1.09 g of the preceding step product with N-tert-butoxycarbonyl-4-amidinobenzoic acid according to Example 12e and chromatography on silica gel (hexane/ethyl acetate 2:1, 1:1) gives 660 mg of ethyl (2S,3R)-4-[3-tert-butoxy-2-[4-(tert-butoxycarbonylamino-imino-methyl)-benzoylamino]-butyryl]-phenoxyacetate, $[\alpha]_D^{20}$=+126.0° (c=0.3, chloroform).

Example 21

From 2 g of 2-methoxy-ethyl (S)-4-[2-[4-(tert-butoxy-carbonylamino-imino-methyl)-benzoylamino]-3-tert-butoxy-propionyl]-phenoxyacetate there are obtained, after deprotection analogously to Example 12 and chromatography on silylated silica gel RP18 (ThF/water gradient), 600 mg of 2-methoxy-ethyl (S)-4-[2-[4-(amino-imino-methyl)-benzoylamino]-3-hydroxy-propionyl]-phenoxyacetate trifluoroacetate, m.p. 174° C., $[\alpha]_D^{20}$=+51.6° (c=0.5, DMSO).

The starting material can be prepared as follows:
a) Alkylation of 1.64 g of tert-butyl (S)-2-tert-butoxy-1-(4-hydroxy-benzoyl)-ethylcarbamate with 2-methoxy-ethyl bromoacetate according to Example 1c leads, after chromatography on silica gel, to 1.58 g of 2-methoxy-ethyl (S)-4-[3-tert-butoxy-2-tert-butoxycarbonylamino-propionyl]-phenoxyacetate, MS (ISP): 454 (M+H)⁺.
b) Reaction of 1.55 g of the preceding step product with N-tert-butoxycarbonyl-4-amidinobenzoic acid according to Example 12e and chromatography on silica gel (hexane/ethyl acetate 2:1, 1:1) gives 2.0 g of 2-methoxy-ethyl (S)-4-[2-[4-(tert-butoxycarbonylamino-imino-methyl)-benzoylamino]-3-tert-butoxy-propionyl]-phenoxyacetate, MS (ISP): 600 (M+H)⁺.

Example 22

From 4.7 g of 2-methoxy-ethyl (S)-4-[2-[4-(tert-butoxy-carbonylamino-imino-methyl)-benzoylamino]-propionyl]-phenoxyacetate there are obtained according to Example 12 and after chromatography on silylated silica gel RP18 (THF/ water gradient) 1.67 g of 2-methoxy-ethyl (S)-4-[2-[4-(amino-imino-methyl)-benzoylamino]-propionyl]-phenoxyacetate, $[\alpha]_D^{20}$=+60.0° (c=0.4, DMSO).

The starting of material can be prepared as follows:
a) Reaction of 3.98 g of tert-butyl (S)-1-(4-hydroxy-benzoyl)-ethylcarbamate with 3.25 g of 2-methoxy-ethyl bromoacetate analogously to Example 1c gives, after chromatography on silica gel (hexane ethyl acetate 2:1), 3.31 g of 2-methoxy-ethyl (S)-4-(2-tert-butoxycarbonylamino-propionyl)-phenoxyacetate, Rf=0.29 (hexane ethyl acetate 1:1).
b) Reaction of 3.3 g of the preceding step product according to Example 12e leads, after chromatography on silica gel (hexane/ethyl acetate 1:2), to 4.76 g of 2-methoxy-ethyl (S)-4-[2-[4-(tert-butoxycarbonylamino-imino-methyl)-benzoylamino]-propionyl]-phenoxyacetate, MS (ISP): 528 (M+H)⁺.

Example 23

Reaction of 199 mg of ethyl (S)-4-[2-[4-(amino-imino-methyl)-benzoylamino]-propionyl]-phenoxyacetate trifluoroacetate with ethyl chloroformate according to Example 15 leads, after chromatography on silica gel (hexane/ethyl acetate 1:2), to 137 mg of ethyl (S)-4-[2-[4-(ethoxycarbonylamino-imino-methyl)-benzoylamino]-propionyl]-phenoxy-acetate, MS (ISP): 470 (M+H)⁺.

The starting material can be prepared as follows:
a) Reaction of 530 mg of tert-butyl (S)-1-(4-hydroxy-benzoyl)-ethylcarbamate with ethyl bromoacetate analogously to Example 1c gives, after chromatography on silica gel (hexane ethyl acetate 5:1), 582 mg of ethyl (S)-4-(2-tert-butoxycarbonylamino-propionyl)-phenoxyacetate, $[\alpha]_D^{20}$=−1.8° (c=0.5, ethanol).
b) Reaction of 702 mg of the product from a) with N-tert-butoxycarbonyl-4-amidinobenzoic acid and cleavage of the protecting group according to Example 12 gives, after chromatography on silylated silica gel RP18 (THF/water gradient), 487 mg of ethyl (S)-4-[2-[4-(amino-imino-methyl)-benzoylamino]-propionyl]-phenoxyacetate trifluoroacetate, m.p. 180° C., $[\alpha]_D^{20}$=+54.2° (c=0.6, DMSO).

Example 24

Cleavage of the protecting groups in 1 g of ethyl (E,Z)-(S)-4-[3-acetoxy-2-[4-[(di-tert-butoxycarbonylamino)-tert-butoxycarbonylimino-methyl]-benzoylamino]-propionyl].-phenoxyacetate analogously to Example 12 gives, after crystallization with ether, 760 mg of ethyl (S)-4-[2-[4-(amino-imino-methyl)-benzoylamino]-3-acetoxy-propionyl]-phenoxy-acetate trifluoroacetate, MS (ISP): 456 (M+H)⁺.

The starting material can be prepared as follows:
a) A solution of 440 mg of ethyl 4-[(S)-3-tert-butoxy-2-tert-butoxycarbonylamino-propionyl]-phenoxyacetate in 10 ml of dichloromethane is stirred with 0.28 ml of trimethylsilyl iodide at room temperature for 3 h., treated with 1 ml of HCl in dioxan (about 4M) and concentrated. The residue is dissolved in 10 ml of THF, treated with 464 mg of (E,Z)-4-(tri-tert-butoxycarbonyl-amidino) benzoic acid, 253 mg of N-methylmorpholine [and], 379 mg of HBTU and stirred at room temperature for 16 h. The resulting suspension is concentrated and the residue is chromatographed on silica gel (hexane/ethyl acetate 1:1). There are obtained 320 mg of ethyl (E,Z)-(S)-4-[2-[4-[(di-tert-butoxy-carbonylamino)-tert-butoxycarbonylimino-methyl]-benzoylamino]-3-hydroxy-propionyl]-phenoxyacetate, MS (ISP): 714 (M+H)⁺.

b) Acetylation of 1.42 g of the preceding step product with 0.156 ml of acetyl chloride in the presence of 223 mg of triethylamine in 30 ml of ether for 1 h. at room temperature gives a suspension. The precipitate is filtered off under suction, the mother liquor is concentrated and the residue is chromatographed on silica gel. There are obtained 1.13 g of ethyl (E,Z)-(S)-4-[3-acetoxy-2-[4-[(di-tert-butoxycarbonylamino)-tert-butoxycarbonylimino-methyl]-benzoylamino]-propionyl]-phenoxyacetate, MS (ISP): 756 (M+H)$^+$.

Example 25

Reaction of 1 g of methyl 4-[4-(amino-imino-methyl)-benzoylamino-acetyl]-phenoxyacetate (Example 25 in EP 0 381 033) with ethyl chloroformate analogously to Example 15 gives, after crystallization in methanol/THF, 810 mg of methyl 4-[4-(ethoxycarbonylamino-imino-methyl)-benzoylaminoacetyl]-phenoxyacetate, MS (ISP): 442 (M+H)$^+$.

Example 26

From 400 mg of ethyl (E,Z)-(R,S)-4-[2-[4-[(di-tert-butoxy-carbonylamino)-tert-butoxycarbonylimino-methyl]-benzoylamino]-3-methylsulphanyl-propionyl]-phenoxyacetate there are obtained, after cleavage of the protecting groups according to Example 12 and crystallization with ether, 190 mg of ethyl (R,S)-4-[2-[4-(amino-imino-methyl)-benzoylamino]-3-methylsulphanyl-propionyl]-phenoxyacetate trifluoroacetate, MS (ISP): 444 (M+H)$^+$.

The starting material can be prepared as follows:

A suspension of 713 mg of ethyl (EZ)-(S)-4-[3-acetoxy-2-[4-[(di-tert-butoxycarbonylamino)-tert-butoxycarbonylimino-methyl]-benzoylamino]-propionyl]-phenoxyacetate (Example 24b) and 140 mg of sodium methanethiolate in 10 ml of acetonitrile is stirred at room temperature for 45 min. Insoluble material is filtered off under suction, the mother liquor is evaporated and the residue is chromatographed on silica gel (hexane/ethyl acetate 2:1). There are obtained 407 mg of ethyl (E,Z)-(R,S)-4-[2-[4-[(di-tert-butoxycarbonylamino)-tert-butoxycarbonylimino-methyl]-benzoylamino]-3-methylsulphanyl-propionyl]-phenoxyacetate, MS (EI): 744 (M+H)$^+$.

Example 27

From 119 mg of ethyl (R,S)-4-[2-[4-(amino-imino-methyl)-benzoyl-amino]-3-methylsulphanyl-propionyl]-phenoxyacetate trifluoroacetate there are obtained in analogy to Example 15 with 28 mg of ethyl chloroformate and chromatography on silica gel (hexane/ethyl acetate 2:3) 78 mg of ethyl (R,S)-4-[2-[4-(ethoxycarbonylamino-imino-methyl)-benzoylamino]-3-methylsulphanyl-propionyl]-phenoxyacetate, MS (EI): 516 (M+H)$^+$.

Example 28

Reaction of 511 mg of ethyl (S)-4-[2-[4-(amino-imino-methyl)-benzoylamino]-propionyl]-phenoxyacetate trifluoroacetate with 2-methoxy-ethyl chloroformate analogously to Example 15 and chromatography of the residue on silica gel (hexane/ethyl acetate 1:2) gives 280 mg of ethyl (S)-4-[2-[4-[imino-2-(methoxy-ethoxycarbonylamino)-methyl]-benzoylamino]-propionyl]-phenoxyacetate, MS (ISP): 500 (M+H)$^+$.

Example 29

Cleavage of the protecting groups in 850 mg of tert-butyl (S)-4-[2-(4-ethoxycarbonylmethoxy-phenyl)-1-methyl-2-oxo-ethylcarbamoylmethoxy]-piperidine-1-carboxylate analogously to Example 12 gives, after chromatography on silylated silica gel RP18 (THF/water gradient), 437 mg of ethyl (S)-4-(2-piperidin-4-yloxyacetylamino-propionyl)-phenoxyacetate trifluoroacetate (sic), MS (ISP): 393 (M+H)$^+$.

The starting material can be prepared as follows:

A solution of 702 mg of ethyl (S)-4-(2-tert-butoxycarbonylamino-propionyl)-phenoxyacetate in 10 ml of dichloromethane is stirred at 0° C. with 0.27 ml of trimethylsilyl iodide for 15 min., treated with 1 ml of HCl in dioxan (4M) and concentrated. The residue is dissolved in 10 ml of dichloromethane. A solution of 518 mg of 1-tert-butoxycarbonyl-piperidin- 4-yl-oxyacetic acid, 594 mg of TPTU and 0.55 ml of N-methylmorpholine in 10 ml of dichloromethane is stirred at 0° C. for 30 min. and subsequently treated with the residue described above. After stirring at room temperature for 2 hours the reaction solution is concentrated and the residue is chromatographed on silica gel (hexane/ethyl acetate 1:1, 1:2). There are obtained 873 mg of tert-butyl (S)-4-[2-(4-ethoxycarbonylmethoxy-phenyl)-1-methyl-2-oxo-ethylcarbamoylmethoxy]-piperidine-1-carboxylate, MS (ISP): 493 (M+H)$^+$.

Example 30

Reaction of 511 mg of ethyl (S)-4-[2-[4-(amino-imino-methyl)-benzoylamino]-propionyl]-phenoxyacetate trifluoroacetate with diethyl chlorophosphate analogously to Example 15 and chromatography of the residue on silica gel (dichloromethane/ethanol 9:1) gives 340 mg of ethyl (S)-4-[2-[4-(diethoxyphosphorylamino-imino-methyl)-benzoylamino]-propionyl]-phenoxyacetate, MS (ISP): 534 (M+H)$^+$.

Example 31

A solution of 1 g of ethyl (S)-4-[2-(4-cyano-benzoylamino)-propionyl]-phenoxyacetate in 10 ml of pyridine and 1 ml of triethylamine is gassed with hydrogen sulphide and stirred at room temperature for 16 h. The reaction solution is concentrated, the residue is dissolved in ethyl acetate, washed with sodium hydrogen carbonate solution, potassium hydrogen sulphate solution and sat. sodium chloride solution, dried and concentrated. With ether the residue gives 580 mg of ethyl (S)-4-[2-[4-(thiocarbamoyl)-benzoylamino]-propionyl]-phenoxyacetate. This is filtered off under suction, dissolved in 65 ml of acetone and 3.3 ml of methyl iodide and stirred at boiling temperature for 3 h. Concentration of the solution and crystallization of the residue in ether gives 609 mg of ethyl (S)-4-[2-[4-(1-methyl-thioformimidoyl)-benzoylamino]-propionyl]-phenoxyacetate hydroiodide. 314 mg of this ester are dissolved in 10 ml of THF, treated with 110 mg of 2-methoxy-ethylamine and stirred at room temperature for 64 h. Concentration of the solution and chromatography of the residue on silylated silica gel RP18 (THF/water gradient) gives 80 mg of ethyl (R,S)-4-[2-[4-[imino-(2-methoxy-ethyl)-amino-methyl]-benzoylamino]-propionyl]-phenoxyacetate hydroiodide. MS (ISP): 456 (M+H)$^+$.

The starting material can be prepared as follows:

Coupling of 5.62 g of ethyl (S)-4-(2-tert-butoxycarbonylamino-propionyl)-phenoxyacetate with 2.82 g of 4-cyanobenzoic acid in analogy to Example 12e gives, after chromatography on silica gel (hexane/ethyl acetate 3:2), 3.67 g of ethyl (S)-4-[2-(4-cyano-benzoylamino)-propionyl]-phenoxyacetate, MS (EI): 381 (M+H)$^+$.

Example 32

Cleavage of the protecting group in 160 mg of ethyl (R,S)-4-[2-[4-[(tert-butyl-dimethyl-silanyloxyamino)-imino-methyl]-benzoyl amino]-propionyl]-phenoxyacetate with tetrabutylammonium fluoride analogously to Example 3b gives, after crystallization of the residue in ethyl acetate/hexane, 70 mg of ethyl (Z)-(R,S)-4-[2-[4-[amino-hydroxyimino-methyl]-benzoylamino]-propionyl]-phenoxyacetate, MS (ISP): 414 (M+H)$^+$.

The starting material can be prepared as follows:

A solution of 300 mg of ethyl (S)-4-[2-[4-(1-methyl-thioformimidoyl)-benzoylamino]-propionyl]-phenoxyacetate (Example 31) and 175 mg of O-tert-butyl-dimethylsilyl-hydroxylamine in 10 ml of THF is stirred at room temperature for 16 h., concentrated and the residue is chromatographed on silica gel (hexanelethyl acetate 3:2). There are obtained 95 mg of ethyl (R,S)-4-[2-[4-[(tert-butyl-dimethyl-silanyloxyamino)-imino-methyl]-benzoylamino]-propionyl]-phenoxyacetate, MS (EI): 528 (M+H)$^+$.

Example 33

From 350 mg of tetrahydropyran-4-yl (S)-4-[2-[4-(amino-imino-methyl)-benzoylamino]-propionyl)-phenoxyacetate hydrochloride (1:0.8) hydroiodide (1:0.4) and 80 mg of ethyl chloroformate there are obtained according to Example 15 and after chromatography of the residue on silica gel (hexane/ethyl acetate 1:2) 204 mg of tetrahydropyran-4-yl (S)-4-[2-[4-(ethoxycarbonylamino-imino-methyl)-benzoylamino]-propionyl]-phenoxyacetate, MS (ISP): 526 (M+H)$^+$.

Example 34

From 2.2 g of ethyl (S)-4-[2-(6-tert-butoxycarbonylaminomethyl-pyridin-3-ylcarbonylamino)-propionyl]-phenoxyacetate there are obtained according to Example 12 and after chromatography of the residue on silylated silica gel RP18 (THF/water gradient) 863 mg of ethyl (S)-4-[2-(6-aminomethyl-pyridin-3-ylcarbonylamino)-propionyl]-phenoxyacetate, MS (ISP): 386 (M+H)$^+$.

The starting material can be prepared as follows:

Coupling of 1.97 g of deprotected ethyl (S)-4-(2-tert-butoxycarbonylamino-propionyl)-phenoxyacetate with 1.7 g of 6-tert-butoxycarbonylaminomethyl-pyridine-3-carboxylic acid in the presence of 2 g of TPTU and 1.25 g of N-methylmorpholine gives, according to Example 12e and after chromatography on silica gel (hexane/ethyl acetate 1:2) 2.28 g of ethyl (S)-4-[2-(6-tert-butoxycarbonylaminomethyl-pyridin-3-ylcarbonylamino)-propionyl]-phenoxyacetate, MS (ISP): 486 (M+H)$^+$.

Example 35

From 90 mg of ethyl (Z)-(R,S)-4-[2-[4-(amino-hydroxyimino-methyl)-benzoylamino]-propionyl]-phenoxyacetate and 25 mg of ethyl chloroformate there are obtained according to Example 15 and after crystallization of the residue in ethyl acetate/hexane 57 mg of ethyl (Z)-(R,S)-4-[2-[4-[amino-ethoxycarbonyloximino-methyl]-benzoylamino]-propionyl]-phenoxyacetate, MS (ISP): 486 (M+H)$^+$.

Example 36

Reaction of 500 mg of ethyl (S)-4-[2-[4-(amino-imino-methyl)-benzoylamino]-propionyl]-phenoxyacetate trifluoroacetate with phenyl chloroformate according to Example 15 leads, after chromatography on silica gel (hexane/ethyl acetate 1:2), to 211 mg of ethyl (S)-4-[2-[4-(imino-phenoxycarbonylamino-methyl)-benzoylamino]-propionyl]-phenoxyacetate, MS (ISP): 518 (M+H)$^+$.

Example 37

Reaction of 511 mg of ethyl (S)-4-[2-[4-(amino-imino-methyl)-benzoylamino]-propionyl]-phenoxyacetate trifluoroacetate with 4-methoxyphenyl chloroformate according to Example 15 leads, after chromatography on silica gel (hexane/ethyl acetate 1:2), to 145 mg of ethyl (S)-4-[2-[4-[imino-(4-methoxy-phenoxycarbonylamino)-methyl]-benzoylamino]-propionyl]-phenoxyacetate, MS (ISP): 548 (M+H)$^+$.

Example 38

98 mg of triphosgene in 5 ml of dichloromethane are added at 0° C. to a solution of 102 mg of tetrahydro-2H-pyran-4-ol and 101 mg of 4-methoxymorpholine in 10 ml of dichloromethane and the mixture is subsequently stirred at room temperature for 2 h. This solution is added to a suspension of 511 mg of ethyl (S)-4-[2-[4-(amino-imino-methyl)-benzoyl-amino]-propionyl]-phenoxyacetate trifluoroacetate in 10 ml of dichloromethane and 10 ml of saturated sodium carbonate solution, stirred at room temperature for 5 min. and the reaction mixture is worked up as in Example 15. Chromatography of the residue on silica gel (ethyl acetate) gives 350 mg of ethyl (S)-4-[2-[4-[imino-(tetrahydro-pyran-4-yloxy-carbonylamino)-methyl]-benzoylamino]-propionyl]-phenoxyacetate, MS (ISP): 526 (M+H)$^+$.

Example 39

540 mg of tetrahydropyran-4-yl (S)-4-[2-[4-(amino-imino-methyl)-benzoylamino]-propionyl)-phenoxyacetate trifluoroacetate (Example 5) are also reacted in analogy to Example 38. After chromatography of the residue an silica gel (ethyl acetate) there are obtained 378 mg of tetrahydropyran-4-yl (S)-4-[2-[4-[imino-(tetrahydropyran-4 -yloxy-carbonylamino)-methyl]-benzoylamino]-propionyl]-phenoxyacetate, MS (ISP): 582 (M+H)$^+$.

Example 40

Reaction of 920 mg of 2-methoxy-ethyl (S)-4-[2-[4-(amino-imino-methyl)-benzoylamino]-propionyl]-phenoxyacetate trifluoroacetate with 2-methoxy-ethyl chloroformate according to Example 15 leads after chromatography on silica gel (hexane/ethyl acetate 1:3) to 430 mg of 2-methoxy-ethyl (S)-$^4$-[2-[4-[imino-(2-methoxy-ethoxy-carbonylamino)-methyl]-benzoylamino]-propionyl]-phenoxyacetate, MS (ISP): 530 (M+H)$^+$.

Example 41

Cleavage of the protecting group from 160 mg of ethyl (S)-4-[2-[4-[(tert-butyl-dimethyl-silanyloxyamino)-imino-methyl]-benzoylamino]-propionyl]-phenoxyacetate with tetrabutylammonium fluoride analogously to Example 3b gives, after crystallization of the residue in ethyl acetate/hexane, 187 mg of ethyl (Z)-(S)-4-[2-[4-(amino-hydroxyimino-methyl)-benzoylamino]-propionyl]-phenoxyacetate, MS (ISP): 414 (M+H)$^+$, $[\alpha]_D^{20}$=+68.8° (c=0.5, DMSO).

The starting material can be prepared as follows:

From 2 g of 4-cyanobenzoic acid there is obtained by analogous reactions as in Example 32a N-tert-butyldimethylsilyloxy-amidinobenzoic acid. This is used directly as the raw material for the coupling of ethyl (S)-4-(2-tert-butoxycarbonylamino-propionyl)-phenoxyacetate in the presence of TPTU according to Example 12e. After chromatography of the residue on silica gel (hexane/ethyl acetate 1:1) there are obtained 561 mg of ethyl (S)-4-[2-[4-[(tert-butyl-dimethyl-silanyloxyamino)-imino-methyl]-benzoylamino]-propionyl]-phenoxyacetate, $[\alpha]_D^{20}$=+62.0° (c=0.5, chloroform).

Example 42

Reaction of 500 mg of ethyl (S)-4-[2-[4-(amino-imino-methyl)-benzoylamino]-propionyl]-phenoxyacetate trifluoroacetate with 4-fluoro-phenyl chloroformate analogously to Example 15 and chromatography of the residue on silica gel (hexane/ethyl acetate 1:2) gives 100 mg of ethyl (S)-4-[2-[4-[(4-fluoro-phenoxycarbonylamino)-imino-methyl]-benzoyl-amino]-propionyl]-phenoxyacetate, MS (ISP): 536 (M+H)$^+$.

Example 43

Starting from 1 g of ethyl (S)-4-[2-[4-(amino-imino-methyl)-benzoylamino]-propionyl]-phenoxyacetate trifluoroacetate there are prepared in analogy to Example 38 with 2-tert-butyl-dimethyl-silanyloxyethanol 200 mg of -ethyl (S)-4-[2-[4-[amino-2-tert-butyl-dimethyl-silanyloxy-ethoxycarbonylimino-methyl]-benzoylamino]-propionyl]-phenoxyacetate and this is deprotected as in Example 3a and chromatographed on silica gel (ethyl acetate/ethanol 95:5). There are obtained 56 mg of ethyl (S)-4-[2-[4-[amino-(2-hydroxy-ethoxycarbonylimino)-methyl]-benzoylamino]-propionyl]-phenoxyacetate, MS (ISP): 486 (M+H)$^+$.

Example 44

Starting from 527 mg of ethyl (S)-4-(2-tert-butoxycarbonylamino-propionyl)-phenoxyacetate and 462 mg of 4-(amino-methoxyimino-methyl)-benzoic acid trifluoroacetate there are obtained as in Example 12e and after chromatography on silica gel (hexane/ethyl acetate 2:3) 500 mg of ethyl (E/Z)-(S)-4-[2-[4-(amino-methoxyimino-methyl)-benzoylamino]-propionyl]-phenoxyacetate trifluoroacetate, MS (ISP): 428 (M+H)$^+$.

The starting material can be prepared as follows:

A solution of 1.47 g of tert-butyl $^4$-cyanobenzoate is reacted analogously to Example 31 with hydrogen sulphide, methyl iodide and O-methyl-hydroxylamine hydrochloride and the crude product is chromatographed on silica gel (hexane/ethyl acetate 9:1). There is obtained 1.0 g of tert-butyl 4-(amino-methoxyimino-methyl)-benzoate. Cleavage of the ester group according to Example 12 with trifluoroacetic acid gives, after crystallization (sic) in ether, 1.13 g of 4-(amino-methoxyimino-methyl)-benzoic acid trifluoroacetate.

Example 45

The silyl protecting group is cleaved from 290 mg of ethyl (S)-4-[2-[4-[(tert-butyl-dimethyl-silanyloxyamino)-imino-methyl]-benzoylamino]-3-hydroxy-propionyl]-phenoxyacetate with tetrabutylammonium fluoride as in Example 3b. After chromatography on silica gel (ethyl acetate there are obtained 145 mg of ethyl (Z)-(S)-4-[2-[4-[amino-hydroxyimino-methyl]-benzoylamino]-3-hydroxy-propionyl]-phenoxyacetate.

The starting material can be prepared as follows:

The free amine is obtained from a solution of 1.27 g of ethyl 4-[(S)-3-tert-butoxy-2-tert-butoxycarbonylamino-propionyl]-phenoxyacetate in 25 ml of dichloromethane according to Example 24a and is subsequently reacted analogously to Example 41a with N-tert-butyl-dimethylsilyloxy-amidinobenzoic acid. After chromatography of the residue on silica gel (hexane/ethyl acetate 1:2) there are obtained 290 mg of ethyl (S)-4-[2-[4-[(tert-butyl-dimethyl-silanyloxyamino)-imino-methyl]-benzoylamino]-3-hydroxy-propionyl]-phenoxyacetate, $R_f$ value: 0.68 (chloroform (sic), methanol, acetic acid, 88:10:2).

Example 46

A solution of 0.8 g of [[4-(p-amidino-N-methylbenzamido)acetyl-o-phenylene]dioxy]diacetic acid (J. Med. Chem. 1992, 35, 4393–4407) in 2-propanol/conc. sulphuric acid (20:1) is left to stand overnight. After removing the solvent the residue is taken up in 50 ml of water, made neutral by adding sodium hydrogen carbonate and covered with 80 ml of dichloromethane. After adding 0.3 g of ethyl chloroformate followed by 20 ml of 0.5N sodium hydroxide solution the organic phase is separated, washed with water, dried over sodium sulphate and concentrated. After chromatography on silica gel (ethyl acetate) and crystallization (diethyl ether) there is obtained 0.51 g of diisopropyl (E and/or Z)-[[4-((p-amino-ethoxycarbonylimino-methyl)-N-methylbenzamido)acetyl-o-phenylene]-dioxy]diacetate. M.p. 56–58° C. MS (EI): 512 (M+H)$^+$.

Example 47

From [[1-[N-(p-amidinobenzoyl)-L-tyrosyl]-4-piperidinyl]oxy]acetic acid (J. Med. Chem. 1992, 35, 4393–4407) there was obtained in an analogous manner to that described in Example 46 ethyl (E/Z)-(S)-1-[2-[4-(amino-ethoxycarbonylimino-methyl)-benzoylamino]-3-(4-hydroxy-phenyl)-propionyl]-piperidin-4-yloxyacetate. $[\alpha]_D^{20}$=+18.1° (c=0.8, EtOH). M.p. 84° C. MS (ISP): 569 (M+H)$^+$.

Example 48

From [[1-[N-(p-amidinobenzoyl)-L-tyrosyl]-4-piperidinyl]oxy]acetic acid (J. Med. Chem. 1992, 35, 4393–4407) there was obtained in an analogous manner to that described in Example 46 isopropyl (E/Z)-(S)-1-[2-[4-(amino-ethoxycarbonylimino-methyl)-benzoylamino]-3-(4-hydroxy-phenyl)-propionyl]-piperidin-4-yloxyacetate. M.p. 88–90° C. MS (ISP): 583 (M+H)$^+$.

Example 49

Isopropyl (E/Z)-(S)-1-[2-[4-(amino-ethoxycarbonylimino-methyl)-benzoylamino]-3-(4-ethoxycarbonyloxy-phenyl)-propionyl]-piperidin-4-yloxyacetate can be isolated as a byproduct of the reaction described in Example 48. M.p. 71–73° C. MS (ISP): 655 (M+H)$^+$.

Example 50

From the reaction of [[1-[N-(p-amidinobenzoyl)-L-tyrosyl]-4-piperidinyl]oxy]acetic acid with isatoic anhydride in the presence of potassium carbonate there is obtained, after usual working up and chromatographic purification of the crude product, (E/Z)-(S)-4-[2-[4-(amino-ethoxycarbonylimino-methyl)-benzoylamino]-3-(4-isopropoxy-carbonylmethoxy-piperidin-1-yl)-3-oxo-propyl]-phenyl 2-amino-benzoate in the form of a colourless foam. MS (ISP): 702 (M+H)$^+$.

Example 51

From the reaction of [[1-[N-(p-amidinobenzoyl)-L-tyrosyl]-4-piperidinyl]oxy]acetic acid with furan-2-carboxylic acid chloride in the presence of potassium carbonate there is obtained, after usual working up and chromatographic purification of the crude product, (E/Z)-(S)-4-[2-[4-(amino-ethoxycarbonylimino-methyl)-benzoylamino]-3-(4-isopropoxy-carbonylmethoxy-piperidin-1-yl)-3-oxo-propyl]-phenyl furan-2-carboxylate in the form of a light yellow foam. MS (ISP): 677 (M+H)$^+$.

Example 52

From the reaction of [[1-[N-(p-amidinobenzoyl)-L-tyrosyl]-4-piperidinyl]oxy]acetic acid with acetic anhydride in the presence of potassium carbonate there is obtained, after usual working up and chromatographic purification of the crude product, isopropyl (E/Z)-(S)-1-[3-[4-acetoxy-phenyl)-2-[4-(amino-ethoxycarbonylimino-methyl)-benzoylamino]-propionyl]-piperidin-4-yloxy-acetate in the form of a colourless foam. MS (ISP): 625 (M+H)$^+$.

Example 53

From the reaction of [[1-[N-(p-amidinobenzoyl)-L-tyrosyl]-4-piperidinyl]oxy]acetic acid with acetylsalicyloyl chloride in the presence of triethylamine there is obtained, after usual working up and chromatographic purification of the crude product, (E/Z)-(S)-4-[2-[4-(amino-ethoxycarbonylimino-methyl)-benzoylamino]-3-(4-isopropoxy-carbonylmethoxy-piperidin-1-yl)-3-oxo-propyl]-phenyl 2-acetoxy-benzoate. M.p. 77–80° C. MS (EI): 745 (M+H)$^+$.

Example 54

From the reaction of tert-butyl [[1-[N-(p-amidinobenzoyl)-L-tyrosyl]-4-piperidinyl]oxy]acetate (EP 505868) with ethyl chloroformate as described in Example 46 followed by treatment with conc. formic acid there is isolated, after usual working up and chromatography, (E/Z)-(S)-1-[2-[4-(amino-ethoxycarbonylimino-methyl)-benzoylamino]-3-(4-hydroxy-phenyl)-propionyl]-piperidin-4-yloxyacetic acid. M.p. 134° C. MS (ISN): 539 (M–H)$^+$.

Example 55

From the reaction of (S)-1-[2-(5-amidinopyridin-2-ylcarbonyl-amino)-3-(4-methoxy-phenyl)-propionyl]-piperidin-4-yloxyacetic acid (EP 505868) in an analogous manner to that described in Example 46 there is obtained ethyl (E/Z)-(S)-1-[2-(5-amino-ethoxycarbonylimino-methylpyridin-2-ylcarbonyl-amino)-3-(4-methoxy-phenyl)-propionyl]-piperidin-4-yloxyacetate. [α]$_D^{20}$=+22.6° (c=1.0, EtOH). M.p. 52–54° C. MS (ISP): 584 (M+H)$^+$.

Example 56

Reaction of tert-butyl (S)-1-[3-(4-hydroxy-phenyl)-2-[4-(imino-propylamino-methyl)-benzoylamino]-propionyl]-piperidin-4-yloxyacetate with conc. formic acid gives, after chromatographic purification of the crude product on silica gel RP18 with a water/methanol gradient, (S)-1-[3-(4-hydroxy-phenyl)-2-[4-(imino-propylamino-methyl)-benzoylamino]-propionyl]-piperidin-4-yloxyacetic acid. M.p. 160° C. MS (ISP): 511 (M+H)$^+$.

The starting material can be prepared as follows:
a) Coupling of Z-Tyr-OH with tert-butyl 4-piperidinyloxyacetate (J. Med. Chem. 1992, 35, 4393–4407) followed by hydrogenolytic removal of the Z protecting group gives tert-butyl 1-[[L-tyrosyl]-4-piperidinyloxy]acetate.
b) By reacting the product of the preceding step with 4-cyano-benzoyl chloride in the presence of sodium hydrogen carbonate there is obtained tert-butyl (S)-1-[3-(4-hydroxy-phenyl)-2-[4-cyano-benzoylamino]-propionyl]-piperidin-4-yloxyacetate.
c) By successive subsequent treatment of the product of the preceding step with hydrogen sulphide in pyridine, methyl iodide in acetone and n-propylamine in a mixture of methanol and acetic acid there is obtained tert-butyl (S)-1-[3-(4-hydroxy-phenyl)-2-[4-(imino-propylamino-methyl)-benzoylamino]-propionyl]-piperidin-4-yloxyacetate. MS (ISP): 567 (M+H)$^+$.

Example 57

Reaction of (S)-4-[[[4-[1-(4-tert-butoxycarbonylmethoxy-piperidin-1-carbonyl)-2-(4-hydroxy-phenyl)-ethylcarbamoyl]-phenyl]-imino-methyl]-amino]-butyric acid with conc. formic acid gives, after chromatographic purification of the crude product, (S)-4-[[[4-[1-(4-carboxy-methoxy-piperidine-1-carbonyl)-2-(4-hydroxy-phenyl)-ethylcarbamoyl]-phenyl]-imino-methyl]-amino]-butyric acid. M.p. 156–160° C. MS (ISP): 555 (M+H)$^+$.

The starting material can be prepared as follows:
By successive subsequent treatment of tert-butyl (S)-1-[3-(4-hydroxy-phenyl)-2-[4-cyano-benzoylamino]-propionyl]-piperidin-4-yloxyacetate (Example 56b)) with hydrogen sulphide in pyridine, methyl iodide in acetone and 4-aminobutyric acid in a mixture of methanol and acetic acid there is obtained (S)-4-[[[4-[1-(4-tert-butoxycarbonylmethoxy-piperidin-1-carbonyl)-2-(4-hydroxy-phenyl)-ethylcarbamoyl]-phenyl]-imino-methyl]-amino]-butyric acid in the form of a colourless foam. MS (ISP): 611 (M+H)$^+$.

Example 58

From the reaction of tert-butyl [[1-[N-(p-amidinobenzoyl)-L-alanyl]-4-piperidinyl]oxy]acetate (J. Med. Chem. 1992, 35, 4393–4407) with ethyl chloroformate as described in Example 46 followed by treatment with conc. formic acid there is isolated, after usual working up and chromatography, (E/Z)-(S)-[1-[2-[4-(amino-ethoxycarbonylimino-methyl)-benzoylamino]-propionyl]-piperidin-4-yloxy]-acetic acid in the form of a colourless foam. MS (ISP): 449 (M+H)$^+$.

Example 59

From [[1-[N-(p-amidinobenzoyl)-L-alanyl]-4-piperidinyl]oxy]acetic acid (J. Med. Chem. 1992, 35, 4393–4407) there was obtained in an analogous manner to that described in Example 46 ethyl (E/Z)-(S)-1-[2-[4-(amino-ethoxycarbonylimino-methyl)-benzoylamino]-propionyl]-piperidin-4-yloxyacetate in the form of a colourless foam. [α]$_D^{20}$=+41.7° (c=1.0, EtOH). MS (ISP): 477 (M+H)$^+$.

Example 60

From [[1-[N-(p-amidinobenzoyl)-L-alanyl]-4-piperidinyl]oxy]acetic acid there was obtained in an analogous manner to that described in Example 46 isopropyl (E/Z)-(S)-1-[2-[4-(amino-ethoxycarbonylimino-methyl)-benzoylamino]-propionyl]-piperidin-4-yloxyacetate in the form of a colourless foam. MS (ISP): 491 (M+H)$^+$.

Example 61

From [[1-[N-(p-amidinobenzoyl)-L-alanyl]-4-piperidinyl]oxy]acetic acid there was obtained in an analogous manner to that described in Example 46 ethyl (E/Z)-(S)-1-[2-[4-(amino-n-butoxycarbonylimino-methyl)-benzoylamino]-propionyl]-piperidin-4-yloxyacetate in the form of a colourless foam. $[\alpha]_D^{20}$=+37.4° (c=0.8, EtOH). MS (ISP): 505 (M+H)$^+$.

Example 62

From [[1-[N-(p-amidinobenzoyl)-L-alanyl]-4-piperidinyl]oxy]acetic acid there was obtained in an analogous manner to that described in Example 46 ethyl (E/Z)-(S)-1-[2-[4-(amino-methoxyethoxycarbonylimino-methyl)-benzoylamino]-propionyl]-piperidin-4-yloxyacetate in the form of a colourless foam. $[\alpha]_D^{20}$=+40.0° (c=0.9, EtOH). MS (ISP): 507 (M+H)$^+$.

Example 63

By esterifying (S)-1-[2-(5-amino-imino-methyl-pyridin-2-ylcarbonylamino)-propionyl]-piperidin-4-yloxy-acetic acid (J. Med. Chem. 1992, 35, 4393–4407) with tetrahydro-2H-pyran-4-ol in the presence of p-toluenesulphonic acid there is obtained, after chromatographic purification of the crude product on silica gel RP 18 with a water/acetonitrile gradient, the p-toluenesulphonate salt of tetrahydropyran-4-yl (S)-1-[2-(5-amino-imino-methyl-pyridin-2-ylcarbonylamino)-propionyl]-piperidin-4-yloxy-acetate. $[\alpha]_D^{20}$=+28.8° (c=0.5, MeOH). MS (ISP): 462 (M+H)$^+$

Example 64

From (S)-1-[2-(5-amino-imino-methyl-pyridin-2-ylcarbonylamino)-propionyl]-piperidin-4-yloxy-acetic acid there was obtained in an analogous manner to that described in Example 46, isopropyl (E/Z)-(S)-1-[2-(5-amino-ethoxycarbonylimino-methyl-pyridin-2-ylcarbonylamino)-propionyl]-piperidin-4-yloxy-acetate. $[\alpha]_D^{20}$=+42.6° (c=1.0, EtOH). M.p. 62–64° C.

MS (EI): 492 (M+H)$^+$.

Example 65

From [[1-[(p-amidino-N-methylbenzamido)acetyl]4-piperidinyl]oxy]acetic acid (EP 505868) there was obtained in an analogous manner to that described in Example 46 ethyl (E/Z)-[1-[2-[[4-(amino-ethoxycarbonylimino-methyl)-benzoyl]-methyl-amino]-acetyl]-piperidin-4-yloxy-acetate. MS (ISP): 477 (M+H)$^+$.

Example 66

From tert-butyl (E/Z)-(S)-1-[2-[4-(amino-methoxyimino-methyl)-benzoylamino]-propionyl]-piperidin-4-yloxyacetate there is obtained by treatment with trifluoro-acetic acid in dichloromethane (E/Z)-(S)-1-[2-[4-(amino-methoxyimino-methyl)-benzoylamino]-propionyl]-piperidin-4-yloxyacetic acid. M.p. 193–195° C. MS (ISP): 407 (M+H)$^+$.

The starting material can be prepared as follows:
a) Coupling of Z-Ala-OH with tert-butyl 4-piperidinyloxyacetate (J. Med. Chem. 1992, 35, 4393–4407) followed by hydrogenolytic removal of the Z. protecting group gives tert-butyl 1-[[L-alanyl]-4-piperidinyloxy]acetate.
b) By reacting the product of the preceding step with 4-cyano-benzoyl chloride in the presence of sodium hydrogen carbonate there is obtained tert-butyl (S)-1-[2-[4-cyano-benzoylamino]-propionyl]-piperidin-4-yloxyacetate.
c) By successive subsequent treatment of the product of the preceding step with hydrogen sulphide in pyridine, methyl iodide in acetone and O-methyl hydroxylamine hydrochloride in DMF in the presence of triethylamine there is obtained tert-butyl (E/Z)-(S)-1-[2-[4-(amino-methoxyimino-methyl)-benzoylamino]-propionyl]-piperidin-4-yloxyacetate in the form of a viscous, colourless oil. MS (ISP): 463 (M+H)$^+$.

Example 67

By esterifying (E/Z)-(S)-1-[2-[4-(amino-methoxyimino-methyl)-benzoylamino]-propionyl]-piperidin-4-yloxyacetic acid in ethanol in the presence of conc. sulphuric acid there is obtained ethyl (E/Z)-(S)-1-[2-[4-(amino-methoxyimino-methyl)-benzoylamino]-propionyl]-piperidin-4-yloxyacetate as a colourless resin. MS (ISP): 435 (M+H)$^+$.

Example 68

From tert-butyl (S)-1-[2-[4-tert-butoxycarbonylaminomethyl-benzoylamino)-3-(4-hydroxy-phenyl)-propionyl]-piperidin-4-yloxyacetate there is obtained by treatment with formic acid (S)-1-[2-(4-aminomethyl-benzoylamino)-3-(4-hydroxy-phenyl)-propionyl]-piperidin-4-yloxyacetic acid. $[\alpha]_D^{20}$=+19.4° (c=0.5, H20). M.p. 166–168° C. MS (ISN): 454 (M–H)$^+$.

The starting material can be prepared by coupling tert-butyl 1-[[L-tyrosyl]-4-piperidinyloxy]acetate (Example 56a)) with 4-tert-butoxycarbonylaminomethyl-benzoic acid in the presence of 1-ethoxy-carbonyl-2-ethoxy-1,2-dihydroquinoline (EEDQ).

Example 69

From tert-butyl (S)-1-[2-[4-tert-butoxycarbonylaminomethyl-benzoylamino)-3-(4-hydroxy-phenyl)-propionyl]-piperidin-4-yloxyacetate (Example 68) by treatment with methyl iodide/potassium carbonate followed by formic acid there is obtained (S)-1-[2-(4-aminomethyl-benzoylamino)-3-(4-methoxy-phenyl)-propionyl]-piperidin-4-yloxyacetic acid. $[\alpha]_D^{20}$=+11.7° (c=0.5, H$_2$O). M.p. 130° C. MS (CI): 470 (M+H)$^+$.

Example 70

By esterifying (S)-1-[2-(4-aminomethyl-benzoylamino)-3-(4-methoxy-phenyl)-propionyl]-piperidin-4-yloxyacetic acid with isopropanol in the presence of sulphuric acid there is obtained isopropyl (S)-1-[2-(4-aminomethyl-benzoylamino)-3-(4-methoxy-phenyl)-propionyl]-piperidin-4-yloxyacetate as the hemisulphate salt. $[\alpha]_D^{20}$=+5.1° (c=0.8, H$_2$O). M.p. 138–140° C. MS (EI): 512 (M+H)$^+$.

Example 71

From tert-butyl (S)-1-[2-(5-aminomethyl-pyridin-2-ylcarbonyl-amino)-3-(4-methoxy-phenyl)-propionyl]-piperidin-4-yloxyacetate by treatment with formic acid there is obtained (S)-1-[2-(5-aminomethyl-pyridin-2-ylcarbonylamino)-3-(4-methoxy-phenyl)-propionyl]-piperidin-4-yloxyacetic acid. $[\alpha]_D^{20}$=+20.0° (c=0.6, H$_2$O). M.p. 174° C. (dec.). MS (ISP): 471 (M+H)$^+$.

The starting material can be prepared by catalytically hydrogenating tert-butyl (S)-1-[2-(5-cyano-pyridin-2-ylcarbonylamino)-3-(4-methoxy-phenyl)-propionyl]-piperidin-4-yloxyacetate (EP 505 868) over palladium-charcoal in a mixture of methanol/water/acetic acid.

Example 72

From (S)-1-[2-(5-aminomethyl-pyridin-2-ylcarbonylamino)-3-(4-methoxy-phenyl)-propionyl]-piperidin-4-yloxyacetic acid there is obtained by esterification with isopropanol as described in Example 70 and after acidification of the crude product with hydrochloric acid the hydrochloride of isopropyl (S)-1-[2-(5-aminomethyl-pyridin-2-ylcarbonylamino)-3-(4-methoxy-phenyl)-propionyl]-piperidin-4-yloxyacetate. M.p. 82–84° C. (from diethyl ether). MS (ISP): 513 (M+H)$^+$.

Example 73

From tert-butyl (S)-4-[1-(4-tert-butoxycarbonylmethoxy-piperidin-1ylcarbonyl)-2-(4-hydroxy-phenyl)-ethylcarbamoylmethoxy]-piperidine-1-carboxylate by treatment with formic acid there is obtained (S)-1-[3-(4-hydroxy-phenyl)-2-piperidin-4-yloxyacetylamino-propionyl]-piperidin-4-yloxyacetic acid, $[\alpha]_D^{20}$=+6.7° (c=0.7, H$_2$O). M.p. 156° C. (dec.). MS (ISP): 464 (M+H)$^+$.

The starting material can be prepared as follows:
a) By treating tert-butyl 4-piperidinyloxyacetate (J. Med. Chem. 1992, 35, 4393–4407) with formic acid there is obtained 4-piperidinyloxyacetic acid, which can be converted with di-tert-butyl dicarbonate in dioxan in the presence of sodium hydroxide into 1-tert-butoxycarbonyl-piperidin-4-yloxyacetic acid.
b) The product of the preceding step can be coupled with tert-butyl 1-[[L-tyrosyl]-4-piperidinyloxy]acetate (Example 56a)) in the presence of 1-ethyloxycarbonyl-2-isobutyloxy-1,2-dihydroquinoline in dichloromethane to give tert-butyl (S)-4-[1-(4-tert-butoxycarbonylmethoxy-piperidin-1-ylcarbonyl)-2-(4-hydroxy-phenyl)-ethylcarbamoylmethoxy]-piperidine-1-carboxylate. MS (ISP): 620 (M+H)$^+$.

Example 74

By reacting (S)-4-[2-[1-tert-butoxycarbonyl-piperidin-4-yloxyacetylamino]-3-(4-ethoxycarbonylmethoxy-piperidin-1-yl)-3-oxo-propyl]-phenyl 2-acetoxy-benzoate with formic acid there is obtained, after the addition of hydrochloric acid to the crude product, the hydrochloride salt of (S)-4-[2-[piperidin-4-yloxyacetylamino]-3-(4-ethoxycarbonylmethoxy-piperidin-1-yl)-3-oxo-propyl]-phenyl 2-acetoxy-benzoate. M.p. 74–76° C (dec.). MS (ISP): 654 (M+H)$^+$.

The starting material can be obtained as follows:
a) Coupling of Z-Tyr-OH with ethyl 4-piperidinyloxyacetate (obtained by trans-esterification of tert-butyl 4-piperidinyloxyacetate with acid in the presence of 1-ethyloxycarbonyl-2-isobutyloxy-1,2-dihydroquinoline) followed by reaction with acetylsalicyloyl chloride in the presence of potassium carbonate and subsequent hydrogenolytic removal of the Z protecting group gives (S)-4-[2-amino-3-(4-ethoxycarbonylmethoxy-piperidin-1-yl)-3-oxo-propyl]-phenyl 2-acetoxy-benzoate.
b) By coupling the product of the preceding step with 1-tert-butoxycarbonyl-piperidin-4-yloxyacetic acid (Example 73b)) in the presence of 1-ethyloxycarbonyl-2-isobutyloxy-1,2-dihydroquinoline in dichloromethane there is obtained (S)-4-[2-[1-tert-butoxycarbonyl-piperidin-4-yloxyacetylamino]-3-(4-ethoxycarbonylmethoxy-piperidin-1-yl)-3-oxo-propyl]-phenyl 2-acetoxy-benzoate. MS (ISP): 754 (M+H)$^+$.

Example 75

By esterifying (E/Z)-(S)-1-[2-[4-(amino-hydroxyimino-methyl)-benzoylamino]-propionyl]-piperidin-4-yloxyacetic acid in ethanol in the presence of conc. sulphuric acid there is obtained ethyl (E/Z)-(S)-1-[2-[4-(amino-hydroxyimino-methyl)-benzoylamino]-propionyl]-piperidin-4-yloxyacetate in the form of cotton wool-like crystals. M.p. 205–207° C. MS (ISP): 421 (M+H)$^+$.

The starting material can be prepared as follows:
a) By reacting tert-butyl (S)-1-[2-[4-cyano-benzoylamino]-propionyl]-piperidin-4-yloxyacetate (Example 66) with hydroxylamine hydrochloride in methanol in the presence of sodium methanolate there is obtained, after stirring overnight and usual working up, tert-butyl (E/Z)-(S)-1-[2-[4-(amino-hydroxyimino-methyl)-benzoylamino]-propionyl]-piperidin-4-yloxyacetate. M.p. 193–194° C. MS (ISP): 449 (M+H)$^+$.
b) By treating the product of the preceding step with formic acid at 50° C. there is obtained, after crystallization from ethyl acetate, (E/Z)-(S)-1-[2-[4-(amino-hydroxyimino-methyl)-benzoylamino]-propionyl]-piperidin-4-yloxyacetic acid. M.p. 176–178° C. MS (ISN): 391 (M+H)$^+$.

Example 76

By esterifying (E/Z)-(S)-1-[2-[4-(amino-hydroxyimino-methyl)-benzoylamino]-propionyl]-piperidin-4-yloxyacetic acid (Example 75b) in 2-propanol in the presence of conc. sulphuric acid there is obtained isopropyl (E/Z)-(S)-1-[2-[4-(amino-hydroxyimino-methyl)-benzoylamino]-propionyl]-piperidin-4-yloxyacetate the form of cotton wool-like crystals. M.p. 205–207° C. MS (ISP): 435 (M+H)$^+$.

Example 77

220 mg of tert-butyl [1-[4-[4-(tert-butoxycarbonylamino-imino-methyl)-phenyl]-4-oxo-butyryl]-piperidin-4-yloxy]-acetate and 3.4 ml of formic acid are stirred at 20° C. for 24 h. The reaction mixture is evaporated in a vacuum, the residue is dissolved in water and again evaporated. 120 mg of [1-[4-[4-(amino-imino-methyl)-phenyl]-4-oxo-butyryl]-piperidin-4-yloxy]-acetic acid, m.p. >250° C., MS: 362 (100, M+H), crystallize from methanol.

The starting material can be obtained as follows.
a) 4-(4-Cyano-phenyl)-4-oxo-butyric acid is activated in THF with 2-chloro-4,6-dimethoxy-1,3,5-triazine and N-methylmorpholine and then reacted with tert-butyl piperidin-4-yloxy-acetate to give tert-butyl [1-[4-(4-cyanophenyl)-4-oxo-butyryl]-piperidin-4-yloxy]-acetate.
b) This is converted in pyridine and triethylamine with hydrogen sulphide into tert-butyl [1-[4-oxo-4-(4-thiocarbamoyl-phenyl)-butyryl]-piperidin-4-yloxy]-acetate, m.p. 140° C.
c) The latter is reacted firstly with methyl iodide in acetone, then with ammonium acetate and acetic acid in methanol and finally with di-tert-butyl dicarbonate in DMF-triethylamine to give tert-butyl [1-[4-[4-(tert-butoxycarbonylamino-imino-methyl)-phenyl]-4-oxo-butyryl]-piperidin-4-yloxy]-acetate. MS: 518 (100, M+H).

Example 78

76 mg of ethyl [1-[4-[4-(tert-butoxycarbonylamino-imino-methyl)-phenyl]-4-oxo-butyryl]-piperidin-4-yloxy]-acetate are stirred in 0.5 ml of methylene chloride and 0.5 ml of trifluoroacetic acid at 20° C. for 2 h. The reaction mixture is evaporated in a vacuum, the residue is dissolved in alcohol and again evaporated. The crystalline product is triturated with ether, filtered off under suction and dried. There are obtained 74 mg of ethyl [1-[4-[4-(amino-imino-methyl)- phenyl]-4-oxo-butyryl]-piperidin-4-yloxy]-acetate trifluoroacetate (1:1), m.p. 188–190° C.

The starting material can be obtained as follows:
a) [1-[4-[4-(Amino-imino-methyl)-phenyl]-4-oxo-butyryl]-piperidin-4-yloxy]-acetic acid is converted in 1N HCl in ethanol into its ethyl ester.
b) This is converted with di-tert-butyl dicarbonate in DMF-triethylamine into the starting material, m.p. 100° C.

Example 79

A mixture of 160 mg of isopropyl [1-[[[4-(amino-imino-methyl)-benzoyl]-(2-methoxyethyl)-amino]-acetyl]-piperidin-4-yloxy]-acetate hydrochloride (1:1), 3.2 ml of methylene chloride, 2.6 ml of water and 0.6 ml of saturated sodium carbonate solution is treated with 0.036 ml of ethyl chloroformate and stirred well at 20° C. for 2 h. The reaction mixture is diluted with methylene chloride, washed with water and sodium chloride solution, dried and evaporated in a vacuum. Chromatography of the residue on silica gel with methylene chloride-isopropanol gives 109 mg of isopropyl [1-[[[4-(ethoxycarbonylamino-imino-methyl)-benzoyl]-(2-methoxy-ethyl)-amino]-acetyl]-piperidin-4-yloxy]-acetate as a colourless foam. MS: 535 (100, M+H).

The starting material is obtained from [1-[[[4-(amino-imino-methyl)-benzoyl]-(2-methoxy-ethyl)-amino]-acetyl]-piperidin-4-yloxy]-acetic acid (EP 505 868) in 1N HCl in isopropanol at 20° C.

Example 80

In analogy to Example 79, from isopropyl [1-[4-[4-(amino-imino-methyl)-phenyl]-4-oxo-butyryl]-piperidin-4-yloxy]-acetate iodide acetate there is obtained isopropyl [1-[4-[4-(ethoxycarbonylamino-imino-methyl)-phenyl]-4-oxo-butyryl]-piperidin-4-yloxy]-acetate, m.p. 86–89° C.

The starting material can be prepared as follows:
a) tert-Butyl [1-[4-oxo-4-(4-thiocarbamoyl-phenyl)-butyryl]-piperidin-4-yloxy]-acetate is cleaved in methylene chloride and trifluoroacetic acid to [1-[4-oxo-4-(4-thiocarbamoyl-phenyl)-butyryl]-piperidin-4-yloxy]-acetic acid, m.p. 203–207° C.
b) Therefrom with sulphuric acid in isopropanol there is obtained isopropyl [1-[4-oxo-4-(4-thiocarbamoyl-phenyl)-butyryl]-piperidin-4-yloxy]-acetate, m.p. 123–128° C.
c) This is reacted with methyl iodide in acetone and subsequently with ammonium acetate and acetic acid in methanol to give the starting material.

Example 81

In analogy to Example 79, from isopropyl [1-[4-[4-(amino-imino-methyl)-phenyl]-4-oxo-butyryl]-piperidin-4-yloxy]-acetate iodide acetate and isobutyl chloroformate there is obtained isopropyl [1-[4-[4-(isobutoxy-carbonylamino-imino-methyl)-phenyl]-4-oxo-butyryl]-piperidin-4-yloxy]-acetate, m.p. 94° C.

Example 82

1.7 g of tert-butyl (RS)-[1-[4-[4-(tert-butoxycarbonylamino-imino-methyl)-phenyl]-2-methyl-4-oxo-butyryl]-piperidin-4-yloxy]-acetate are stirred in 8.5 ml of methylene chloride and 8.5 ml of trifluoroacetic acid at 20° C. for 3 h. After evaporation of the solvent in a vacuum the residue is dissolved in water and the solution is again evaporated. After drying the residue is triturated in alcohol, filtered off under suction and dried. There are obtained 1.13 g of (RS)-[1-[4-[4-(amino-imino-methyl)-phenyl]-2-methyl-4-oxo-butyryl]-piperidin-4-yloxy-acetic acid trifluoroacetate (1:1), m.p. 217° C.

The starting material can be obtained as follows:
a) 4-(4-Amino-phenyl)-2-methyl-4-oxo-butyric acid is converted via the corresponding diazonium compound (Sandmeyer reaction) into 4-(4-cyano-phenyl)-2-methyl-4-oxo-butyric acid, m.p. 137° C.
b) As described in Example 77a), this is coupled with tert-butyl piperidin-4-yloxy-acetate to give tert-butyl (RS)-[1-[4-(4-cyano-phenyl)-2-methyl-4-oxo-butyryl]-piperidin]-4-yloxy-acetate, m.p. 114–116° C.
c) tert-Butyl (RS)-[1-[2-methyl-4-oxo-4-(4-thiocarbamoyl-phenyl)-butyryl]-piperidin-4-yloxy]-acetate, m.p. 152–155° C., is obtained therefrom with hydrogen sulphide in pyridine/triethylamine.
d) This is reacted firstly with methyl iodide in acetone, then with ammonium acetate and acetic acid in methanol and subsequently with di-tert-butyl dicarbonate in methylene chloride and aqueous sodium carbonate solution to give the starting material, MS: 532 (100, M+H).

Example 83

734 mg of (RS)-[1-[4-[4-(amino-imino-methyl)-phenyl]-2-methyl-4-oxo-butyryl]-piperidin-4-yloxy]-acetic acid trifluoroacetate are stirred in 15 ml of 1N HCl in isopropanol at about 20° C. for 19 h. After evaporation of the solvent and drying in a high vacuum there are obtained 650 mg of isopropyl (RS)-[1-[4-[4-(amino-imino-methyl)-phenyl]-2-methyl-4-oxo-butyryl]-piperidin-4-yloxy]-acetate hydrochloride (1:1) as a hygroscopic amorphous powder, MS: 376 (100, M+H).

Example 84

In analogy to Example 79, from isopropyl (RS)-[1-[4-[4-(amino-imino-methyl)-phenyl]-2-methyl-4-oxo-butyryl]-piperidin-4-yloxy]-acetate hydrochloride there is obtained isopropyl (RS)-[1-[4-[4-(ethoxycarbonylamino-imino-methyl)-phenyl-2-methyl-4-oxo-butyryl]-piperidin-4-yloxy]-acetate as a resinous foam, MS: 490 (100, M+H).

Example 85

Likewise, from the same starting material with isobutyl chloroformate there is obtained isopropyl (RS)-[1-[4-[4-(Isobutoxycarbonylamino-imino-methyl)-phenyl]-2-methyl-4-oxo-butyryl]-piperidin-4-yloxy]-acetate as a foam, MS: 518 (100, M+H).

Example 86

209 mg of ethyl (RS)-2-[4-(tert-butoxycarbonylamino-imino-methyl)-benzoyl]-4-(4-ethoxycarbonylmethoxy-phenyl)-4-oxo-butyrate and 4.2 ml of formic acid are left to stand at 20° C. for 6.5 h. The reaction mixture is evaporated, the residue is dissolved in water and again evaporated. The dried residue is triturated in ether and filtered off under suction. There are obtained 158 mg of ethyl (RS)-2-[4-(amino-imino-methyl)-benzoyl]-4-(4-ethoxycarbonylmethoxyphenyl)-4-oxo-butyrate formate (1:1), m.p. 162° C.

The starting material can be obtained as follows:
a) From ethyl 4-cyanobenzoyl acetate and ethyl [4-(bromoacetyl)-phenoxy]-acetate in acetone in the presence of potassium carbonate there is obtained ethyl (RS)-2-(4-cyano-benzoyl)-4-[(4-ethoxycarbonylmethoxy)-phenyl]-4-oxo-butrate; MS: 437 (2, M).

b) This is converted in pyridine and triethylamine with hydrogen sulphide into ethyl (RS)-4-(4-ethoxycarbonylmethoxy-phenyl)-4-oxo-2-(4-thiocarbamoyl-benzoyl)-butyrate; MS: 472 (100, M+H).

c) The latter is reacted firstly with methyl iodide in acetone, then with ammonium acetate and acetic acid in methanol and finally with di-tert-butyl dicarbonate in methylene chloride and aqueous sodium carbonate solution to give ethyl (RS)-2-[4-(tert-butoxycarbonylamino-imino-methyl)-benzoyl]-4-(4-ethoxycarbonylmethoxy-phenyl)-4-oxo-butyrate; MS: 555 (100, M+H).

Example 87

In analogy to Example 79, from ethyl (RS)-2-[4-(amino-imino-methyl)-benzoyl]-4-(4-ethoxycarbonylmethoxy-phenyl)-4-oxo-butyrate formate and ethyl chloroformate there is obtained ethyl (RS)-2-[4-(ethoxy-carbonylamino-imino-methyl)-benzoyl]-4-(4-ethoxycarbonylmethoxy-phenyl)-4-oxo-butyrate; MS: 527 (100, M+H).

Example 88

3.8 g of ethyl 4-[3-(4-thiocarbamoyl-benzoyl)-propionyl]-phenoxyacetate, 76 ml of acetone and 5.9 ml of methyl iodide are stirred at 45° C. for 3 h. The reaction mixture is evaporated, the residue is dissolved in 117 ml of methanol, treated with 2.2 g of ammonium acetate and 0.54 ml of acetic acid and stirred at 60° C. for 3.5 h. The reaction mixture is concentrated in a vacuum until crystallization begins and is then cooled. The precipitate is filtered off under suction and is purified by trituration in acetonitrile. There are obtained 2 g of ethyl [4-[4-[4-(amino-imino-methyl)-phenyl]-4-oxo-butyryl]-phenoxy]-acetate acetate (1:1), m.p. 212° C.

The starting material can be obtained as follows:

a) 24.4 ml of pyridine are added to a suspension of 14.4 g of anhydrous magnesium chloride in 151 ml of dry methylene chloride and 25.2 ml of tert-butyl acetoacetate at 5° C. After 15 minutes 25 g of 4-cyanobenzoyl chloride are added and the mixture is subsequently stirred at 20° C. for 2 h. For the working up, the mixture is diluted with ethyl acetate, washed with ice-cold dilute hydrochloric acid and water, dried and evaporated in a vacuum. The residue is dissolved in 600 ml of tert-butyl methyl ether and treated while stirring vigorously with 160 ml of 10 percent ammonia solution. After 2 h the phases are separated, washed with water, dried and evaporated in a vacuum. Filtration on silica gel and crystallization from pentane gives 13.1 g of pure tert-butyl 3-(4-cyanophenyl)-3-oxo-propionate, m.p. 82–83° C.

b) This is converted in acetone in the presence of potassium carbonate with ethyl [4-(bromoacetyl)-phenoxy]-acetate into ethyl (RS)-[4-[3-tert-butoxycarbonyl-3-(4-cyano-benzoyl)-propionyll-phenoxy]-acetate; MS: 465 (1, M).

c) The latter is stirred for 4 h. in formic acid at 20° C., evaporated, evaporated with toluene and heated to 70° C. for 1.5 h. in toluene. There is thus obtained ethyl [4-[3-(4-cyano-benzoyl)-propionyl]-phenoxy]-acetate, m.p. 115–116° C.

d) This is converted in pyridine and triethylamine with hydrogen sulphide into ethyl 4-[3-(4-thiocarbamoyl-benzoyl)-propionyl]-phenoxy-acetate, m.p. 179–180° C.

Example 89

In analogy to Example 79, from ethyl [4-[4-[4-(amino-imino-methyl)-phenyl]-4-oxo-butyryl]-phenoxy]-acetate acetate there is obtained ethyl [4-[4-[4-(ethoxycarbonylamino-imino-methyl)-phenyl]-4-oxo-butyryl]-phenoxy]-acetate; m.p. 167–168° C.

Example 90

By reacting dimethyl [[4-(p-cyano-N-methylbenzamido)acetyl-o-phenylene]dioxy]diacetate (J. Med. Chem. 1992, 35, 4393–4407) with hydroxylamine hydrochloride in methanol in the presence of sodium methanolate there is obtained, after stirring overnight and working up, dimethyl [[[4-(p-amino-hydroxyimino-methyl)-N-methylbenzamido]acetyl-o-phenylene]dioxy]diacetate in the form of a colourless solid. M.p. 58–60° C. MS (ISP): 488 (M+H)$^+$.

Example 91

By reacting methyl (S)-[2-[1-[2-[4-cyano-benzoylamino]-propionyl]-piperidin-4-yloxy]-acetylamino]-acetate with hydroxylamine hydrochloride in methanol in the presence of sodium methanolate there is obtained, after stirring overnight, working up and chromatographic purification on silica gel (dichloromethane/methanol 6:1), methyl (Z)-(S)-[2-[1-[2-[4-(amino-hydroxyimino-methyl)-benzoylamino]-propionyl]-piperidin-4-yloxy]-acetylamino]-acetate. M.p. 168–172° C. MS (ISP): 464 (M+H)$^+$.

The starting material can be prepared as follows:
a) Treatment of tert-butyl 1-benzyloxycarbonyl-piperidin-4-yloxy-acetate (J. Med. Chem. 1992, 35, 4393–4407) with formic acid followed by reaction of the resulting product with glycine ethyl ester hydrochloride in the presence of O-benzotriazol-1-yl-N,N,N',N'-tetramethyluronium hexafluorophosphate (HBTU) and N-methylmorpholine gives ethyl [[1-benzyloxycarbonyl]-piperidin-4-yloxy-acetylamino]-acetate as a colourless oil. MS (ISP): 379 (M+H)$^+$.

b) By catalytically hydrogenating the product of the preceding step followed by coupling with Z-Ala-OH in the presence of HBTU and N-methylmorpholine there is obtained (S)-benzyl-[2-[4-[[[[ethoxycarbonyl]methylamino]carbonyl]methoxy]piperidinyl]-1-oxopropyl]carbamate in the form of a light yellow oil. MS (ISP): 450 (M+H)$^+$.

c) By catalytically hydrogenating the product of the preceding step followed by coupling with 4-cyanobenzoyl chloride in the presence of sodium hydrogen carbonate there is obtained ethyl (S)-[2-[1-[2-[4-cyano-benzoylamino]-propionyl]-piperidin-4-yloxy]-acetylamino]-acetate in the form of a colourless resin. MS (ISP): 445 (M+H)$^+$.

Example 92

By esterifying (Z)-(S)-1-[2-[4-(amino-hydroxyimino-methyl)-benzoylamino]-propionyl]-piperidin-4-yloxyacetic acid (Example 75) in 1-hexanol in the presence of conc. sulphuric acid there is obtained n-hexyl (Z)-(S)-1-[2-[4-(amino-hydroxyimino-methyl)-benzoylamino]-propionyl]-piperidin-4-yloxyacetate in the form of cotton wool-like crystals. M.p. 169–171° C. MS (ISP): 477 (M+H)$^+$.

Example 93

By reacting (Z)-(S)-1-[2-[4-(amino-hydroxyimino-methyl)-benzoyl-amino]-propionyl]-piperidin-4-yloxyacetic acid (Example 75) with isobutyl (E/Z)-2-bromomethyl-pent-2-enoate (J. Antibiotics 1992, 45, 1358–1364) in the presence of triethylamine there is obtained isobutyl (E/Z)-(S)-2-[[1-[2-[4-[(Z)-amino-hydroxyimino-methyl)-benzoylamino]-propionyl]- piperidin-4-yloxy]-acetoxymethyl]pent-2-enoate in the form of colourless crystals. M.p. 94–96° C. MS (ISP): 561 (M+H)+.

Example 94

By reacting (Z)-(S)-1-[2-[4-(amino-hydroxyimino-methyl)-benzoyl-amino]-propionyl]-piperidin-4-yloxyacetic acid (Example 75) with chloromethyl pivalate in the presence of triethylamine there is obtained tert-butylcarbonyloxy-methyl (Z)-(S)-[1-[2-[4-(amino-hydroxyimino-methyl)-benzoylamino]-propionyl]-piperidin-4-yloxy]acetate in the form of colourless crystals. M.p. 126° C. MS (ISP): 507 (M+H)+.

Example 95

By reacting (Z)-(S)-1-[2-[4-(amino-hydroxyimino-methyl)-benzoyl-amino]-propionyl]-piperidin-4-yloxyacetate (Example 75) with 1-iodoethyl isopropyl carbonate (J. Antibiotics 1987, 40, 370–384) in the presence of dicyclohexylamine in dimethylacetamide there is obtained (R/S)-1-isopropoxycarbonyloxy-ethyl (Z)-(S)-[1-[2-[4-(amino-hydroxyimino-methyl)-benzoylamino]-propionyl]-piperidin-4-yloxy]acetate as a colourless powder. M.p. 113° C. (dec.). MS (ISP): 523 (M+H)+.

Example 96

By reacting (Z)-(S)-1-[2-[4-(amino-hydroxyimino-methyl)-benzoyl-amino]-propionyl]-piperidin-4-yloxyacetic acid (Example 75) with methanol as described in Example 75 there is obtained methyl (Z)-(S)-[1-[2-[4-(amino-hydroxyimino-methyl)-benzoylamino]-propionyl]-piperidin-4-yloxy]acetate as a colourless powder. M.p. 177–178° C. (dec.). MS (ISP): 407 (M+H)+.

Example 97

Starting from tert-butyl (S)-1-[2-(5-cyano-pyridin-2-ylcarbonylamino)-propionyl]-piperidin4-yloxy-acetate (J. Med. Chem. 1992, 35, 4393–4407) there is obtained in the manner described in Example 75 ethyl (Z)-(S)-[1-[2-[5-(amino-hydroxyimino-methyl)-pyridin-2-ylcarbonylamino]-propionyl]-piperidin-4-yloxy]acetate in the form of colourless crystals. M.p. 148–150° C. MS (ISP): 422 (M+H)+.

Example 98

Starting from tert-butyl (S)-1-[3-(4-hydroxy-phenyl)-2-[4-cyano-benzoylamino]-propionyl]-piperidin-4-yloxy-acetate (Example 56 b) there is obtained in the manner described in Example 75 ethyl (Z)-(S)-[1-[2-[4-(amino-hydroxyimino-methyl)-benzoylamino]-3-(4-hydroxyphenyl)-propionyl]-piperidin-4-yloxy]acetate in the form of colourless crystals. M.p. 107–110° C. MS (ISP): 513 (M+H)+.

Example 99

By esterifying [[1-[N²-(p-amidinobenzoyl)-L-ornithyl]-piperidin-4-yl]oxy]acetic acid (J. Med. Chem. 1992, 35, 4393–4407) with ethanol in the presence of hydrochloric acid followed by reaction of the resulting product with ethyl chloroformate as described in Example 46 there is obtained ethyl (E/Z)-(S)-[1-[2-[4-(amino-ethoxycarbonylimino-methyl)-benzoyl-amino]-5-ethoxycarbonylamino-pentanoyl]-piperidin-4-yloxy]acetate as a colourless foam. MS (ISP): 592 (M+H)+.

Example 100

By reacting ethyl (S)-[1-[2-[4-cyano-benzoylamino]-5-benzoylamino-pentanoyl]-piperidin-4-yloxy]acetate with hydroxylamine hydrochloride as described in Example 75 there is obtained ethyl (Z)-(S)-[1-[2-[4-(amino-hydroxyimino-methyl)-benzoylamino]-5-benzoylamino-pentanoyl]-piperidin-4-yloxy]acetate as a colourless resin. MS (ISP): 568 (M+H)+.

The starting material can be prepared as follows:

a) By reacting tert-butyl [[1-[N⁵-(tert-butoxycarbonyl)-L-ornithyl]-piperidin-4-yl]oxy]acetate (J. Med. Chem. 1992, 35, 4393–4407) with 4-cyanobenzoyl chloride in a two-phase mixture of dichloromethane and saturated sodium hydrogen carbonate solution there is obtained after working up tert-butyl (S)-[1-[2-[4-cyanbenzoylamino]-5-tert-butoxy-carbonylamino-pentanoyl]-piperidin-4-yloxy]acetate. MS (ISP): 559 (M+H)+.

b) Reaction of the product of the preceding step with trifluoroacetic acid in dichloromethane gives (S)-[1-[2-[4-cyanbenzoylamino]-5-amino-pentanoyl]-piperidin-4-yloxy]acetic acid as a colourless resin. MS (ISP): 403 (M+H)+.

c) By esterifying the product of the preceding step with ethanol in the presence of conc. sulphuric acid followed by reaction with benzoyl chloride in a two-phase mixture of dichloromethane and saturated sodium hydrogen carbonate solution there is obtained ethyl (S)-[1-2-[4-cyano-benzoylamino]-5-benzoylamino-pentanoyl]-piperidin-4-yloxy]acetate. MS (EI): 348 (M-C₉H₁₆NO₃)+, 188 (C₉H₁₈NO₃).

Example 101

By reacting ethyl (S)-[1-[2-[4-cyano-benzoylamino]-5-ethoxy-carbonylamino-pentanoyl]-piperidin-4-yloxy]acetate with hydroxylamine hydrochloride in the presence of sodium ethanolate as described in Example 75 there is obtained ethyl (Z)-(S)-[1-[2-[4-(amino-hydroxyimino-methyl)-benzoylamino]-5-ethoxycarbonylamino-pentanoyl]-piperidin-4-yloxy]acetate as a colourless foam. MS (ISP): 536 (M+H)+.

The starting material can be prepared as follows:

By esterifying (S)-[1-[2-[4-cyanobenzoylamino]-5-amino-pentanoyl]-piperidin-4-yloxy]acetic acid (Example 100) with ethanol in the presence of conc. sulphuric acid followed by reaction with ethyl chloroformate in a two-phase mixture of dichloromethane and 1N sodium hydroxide solution there is obtained ethyl (S)-[1-[2-[4-cyano-benzoylamino]-5-ethoxy-carbonylamino-pentanoyl]-piperidin-4-yloxy]acetate. MS (ISP): 503 (M+H)+.

Example 102

By reacting ethyl (S)-[1-[2-[4-cyano-benzoylamino]-5-(3-butyl-ureido)-pentanoyl]-piperidin-4-yloxy]acetate with hydroxylamine hydrochloride in the presence of sodium ethanolate as described in Example 75 there is obtained ethyl (Z)-(S)-[1-[2-[4-(amino-hydroxyimino-methyl)-benzoylamino]-5-(3-butyl-ureido)-pentanoyl]-piperidin-4-yloxy]acetate as a colourless foam. MS (ISP): 563 (M+H)+.

The starting material can be prepared as follows:

By esterifying (S)-[1-[2-[4-cyanobenzoylamino]-5-amino-pentanoyl]-piperidin-4-yloxy]acetic acid (Example 100) with ethanol in the presence of conc. sulpuric acid followed by reaction with n-butyl isocyanate in a two-phase mixture of dichloromethane and saturated sodium hydrogen carbonate solution there is obtained ethyl (S)-[1-[2-[4-cyano-benzoyl-amino]-5-(3-butyl-ureido)-pentanoyl]-piperidin-4-yloxy]acetate. MS (ISP): 530 (M+H)⁺.

Reference Example 103

Starting from tert-butyl 4-piperidinyloxy-acetate and (S)-2-benzyl-oxycarbonyl-amino-butyric acid there is obtained in the manner described in J. Med. Chem. 1992, 35, 4393–4407 the formate of (S)-[1-[2-[4-(amino-imino-methyl)-benzoylamino]-butyryl]-piperidin-4-yloxy]acetic acid in the form of colourless crystals. M.p. 240° C. (dec.). MS (ISP): 391 (M+H)⁺.

Reference Example 104

By esterifying (S)-[1-[2-[4-(amino-imino-methyl)-benzoylamino]-butyryl]-piperidin-4-yloxy]acetic acid (Example 103) in ethanol in the presence of conc. sulpuric acid there is obtained the hemisulphate of ethyl (S)-[1-[2-[4-(amino-imino-methyl)-benzoylamino]-butyryl]-piperidin-4-yloxy]acetate in the form of colourless crystals. M.p. 256–260° C. (dec.). MS (ISP): 419 (M+H)⁺.

Example 105

By reacting ethyl (S)-[1-[2-[4-(amino-imino-methyl)-benzoylamino]-butyryl]-piperidin-4-yloxy]acetate(Example 104) with n-butyl chloroformate in a two-phase mixture of dichloromethane and saturated sodium hydrogen carbonate solution there is obtained ethyl (E/Z)-(S)-[1-[2-[4-(amino-n-butoxycarbonylimino-methyl)-benzoylamino]-butyryl]-piperidin-4-yloxy]acetate in the form of a colourless foam. MS (ISP): 519 (M+H)⁺.

Example 106

By esterifying (Z)-(S)-[1-[2-[4-(amino-hydroxyimino-methyl)-benzoylamino]-butyryl]-piperidin-4-yloxy]acetic acid in ethanol in the presence of conc. sulpuric acid there is obtained ethyl (Z)-(S)-[1-[2-[4-(amino-hydroxyimino-methyl)-benzoylamino]-butyryl]-piperidin-4-yloxy]acetate in the form of a colourless foam. MS (ISP): 435 (M+H)⁺.

The starting material can be prepared as follows:
a) Reaction of. t-butyl (S)-[1-[2-amino-butanoyl]-piperidin-4-yloxy]-acetate (prepared analogously as described in J. Med. Chem. 1992, 35, 4393–4407) with 4-cyanobenzoyl chloride gives tert-butyl (S)-[1-[2-[4-cyano-benzoylamino]-butyryl]-piperidin-4-yloxy]acetate. MS (EI): 429 (M⁺).
b) Reaction of the product of the preceding step with hydroxylamine hydrochloride gives tert-butyl (Z)-(S)-[1-[2-[4-(amino-hydroxyimino-methyl)-benzoylamino]-butyryl]-piperidin-4-yloxy]acetate. MS (ISP): 463 (M+H)⁺.
c) Treatment of the product of the preceding step with formic acid gives (Z)-(S)-[1-[2-[4-(amino-hydroxyimino-methyl)-benzoylamino]-butyryl]-piperidin-4-yloxy] acetic acid in the form of a colourless foam. MS (ISP): 407 (M+H)⁺.

Reference Example 107

Starting from tert-butyl 4-piperidinyloxy-acetate and Z-Me-Ala-OH there is obtained in the manner described in J. Med. Chem. 1992, 35, 4393-4407 (S)-[1-[2-[[4-(amino-imino-methyl)-benzoyl]-methyl-amino]-propionyl]-piperidin-4-yloxy]acetic acid as a colourless resin. MS (ISP): 391 (M+H)⁺.

Example 108

From 1-tert-butoxycarbonyl-piperidin-4-yloxy-acetic acid (Example 73) and tert-butyl 1-[[L-alanyl]-4-piperidinyloxy]acetate (Example 66) there is obtained in the manner described in Example 73 (S)-[1-[2-(piperidin-4-yloxy-acetamido)-propionyl]-piperidin-4-yloxy]acetic acid in the form of a colourless foam. MS (ISN): 370 (M−H)⁺.

Example 109

By reacting ethyl (S)-3-[1-[2-[4-cyano-benzoyl-amino]-propionyl]-piperidin-4-yl]propionate with hydroxylamine hydrochloride as described in Example 75 there is obtained ethyl (Z)-(S)-3-[1-[2-[4-(amino-hydroxy-imino-methyl)-benzoyl-amino]-propionyl]-piperidin-4-yl]propionate in the form of colourless crystals. M.p. 194–195° C. $[\alpha]_D^{20}$=+75.6° (c=1, acetic acid). MS (ISP): 419 (M+H)⁺.

The starting material can be prepared as follows:
a) Esterification of 3-[piperidin-4-yl]-propionic acid (1. Org. Chem. 1945, 10, 562) with ethanol in the presence of conc. sulphuric acid followed by coupling with Z-Ala-OH in the presence of 1-ethyloxycarbonyl-2-isobutyloxy-1,2-dihydroquinoline (EEDQ) in dichloromethane gives ethyl 3-[1-(2-benzyloxycarbonylamino-propionyl)-piperidin-4-yl]-propionate as a colourless oil. MS (ISP): 391 (M+H)⁺.
b) By catalytically hydrogenating the product of the preceding step in ethanol in the presence of 10% Pd/C followed by reaction with 4-cyanobenzoyl chloride there is obtained ethyl (S)-3-[1-[2-[4-cyano-benzoyl-amino]-propionyl]-piperidin-4-yl]propionate in the form of colourless crystals. M.p. 108–109° C. MS (EI): 385 (M)⁺.

Example 110

By catalytically hydrogenating (Z)-(S)-[[acetyl-1-[2-[4-(amino-hydroxyimino-methyl)-benzoyl-amino]-propionyl]-piperidin-4-yl]-amino]-acetic acid in water/acetic acid 9:1 in the presence of 10% Pd/C there is obtained (S)-[[acetyl-1-[2-[4-(amino-imino-methyl)-benzoyl-amino]-propionyl]-piperidin-4-yl]-amino]acetic acid as a colourless powder. M.p. above 230° C. (dec.). MS (ISP): 418 (M+H)⁺.

The starting material can be prepared as follows:
a) Reaction of N-benzyloxycarbonyl-4-piperidone with glycine ethyl ester hydrochloride in the presence of sodium borhydride followed by acylation of the product with acetic anhydride gives ethyl acetyl-[1-[benzyloxycarbonyl]-piperidin-4-yl]-amino-acetate as a colourless oil.
b) By catalytically hydrogenating the product of the preceding step in the presence of 10% Pd/C in ethanol followed by coupling with Z-Ala-OH in the presence of 1-ethoxycarbonyl-2-ethoxy-1,2-dihydroquinoline (EEDQ) there is obtained ethyl (S)-[[[acetyl-1-[2-benzyloxycarbonyl-amino]-propionyl]-piperidin-4-yl]-amino]acetate as a colourless oil. MS (ISP): 456 (M+Na)⁺.
c) By catalytically hydrogenating the product of the preceding step over 10% Pd/C in ethanol in the presence of acetic acid followed by reaction with 4-cyanobenzoyl chloride in a two-phase mixture of dichloromethane and saturated sodium hydrogen carbonate solution there is obtained ethyl (S)-[[acetyl-1-[2-[4-cyan-benzoyl-amino]-propionyl]-piperidin-4-yl]-amino]acetate as a colourless foam. MS (ISP): 428 (M+H)⁺.
d) By reacting the product of the preceding step with hydroxylamine hydrochloride followed by saponification with sodium hydroxide solution there is obtained (Z)-(S)-[[acetyl-1-[2-[4-(amino-hydroxyimino-methyl)-benzoyl-amino]-propionyl]-piperidin-4-yl]-amino]acetic acid in the form of colourless crystals. M.p. above 270° C. (dec.). MS (ISP): 434 (M+H)⁺.

Example 111

In an analogous manner to that described in Example 110, there is obtained using di-tert-butyl dicarbonate in place of acetic anhydride ethyl (Z) -(R/S)-[[tert-butoxycarbonyl-1-[2-[4-(amino-hydroxyimino-methyl)-benzoyl-amino]-propionyl]-piperidin-4-yl]-amino]acetate as a colourless foam. MS (ISP): 520 (M+H)$^+$.

Example 112

By esterifying (Z)-[1-[2-[4-[amino-hydroxyimino-methyl]-phenyl-carbamoyl]-acetyl]-piperidin-4-yloxy]-acetic acid with ethanol there is obtained ethyl (Z)-[1-[2-[4-[amino-hydroxyimino-methyl]-phenylcarbamoyl]-acetyl]-piperidin-4-yloxy]-acetate in the form of colourless crystals. M.p. 180° C. (dec.). MS (ISP): 407 (M+H)$^+$.

The starting material can be prepared as follows:
a) Reaction of 4-amino-benzonitrile with Meldrum's acid gives 2-[4-cyano-phenylcarbamoyl]-acetic acid.
b) By coupling the product of the preceding step with tert-butyl 4-piperidinyloxy-acetate (J. Med. Chem. 1992, 35, 4393–4407) in the presence of O-benzotriazol-1-yl-N,N,N',N'-tetramethyluronium hexafluorophosphate (HBTU) and N-methylmorpholine there is obtained tert-butyl [1-[2-[4-cyano-phenylcarbamoyl]-acetyl]-piperidin-4-yloxy]-acetate. MS (EI): 401 (M)$^+$.
c) Reaction of the product of the preceding step with hydroxyl-aminehydrochloride as described in Example 75 gives tert-butyl (Z)-[1-[2-[4-[amino-hydroxyimino-methyl]-phenylcarbamoyl]-acetyl]-piperidin-4-yloxy]-acetate. M.p. 161–163° C. MS (ISP): 435 (M+H)$^+$.
d) By treating the product of the preceding step with formic acid there is obtained (Z)-[1-[2-[4-[amino-hydroxyimino-methyl]-phenylcarbamoyl]-acetyl]-piperidin-4-yloxy]-acetic acid in the form of colourless crystals. M.p. 133–135° C. MS (ISN): 377 (M–H)$^+$.

Example 113

By catalyticallly hydrogenating ethyl (Z)-[1-[2-[4-[amino-hydroxyimino-methyl]-phenylcarbamoyl]-acetyl]-piperidin-4-yloxy]-acetate (Example 112) in the presence of 10% Pd/C in ethanol/acetic acid 15:1 there is obtained the acetate of ethyl [1-[2-[4-[amino-imino-methyl]-phenylcarbamoyl]-acetyl]-piperidin-4-yloxy]-acetate in the form of colourless crystals. M.p. 191–192° C. MS (ISP): 391 (M+H)$^+$.

Example 114

By reacting ethyl [1-[2-[4-[amino-imino-methyl]-phenylcarbamoyl]-acetyl]-piperidin-4-yloxy]-acetate (Example 113) with ethyl chloroformate in the presence of 0.2N sodium hydroxide solution there is obtained ethyl (E/Z)-[1-[2-[4-[amino-ethoxycarbonylimino-methyl]-phenylcarbamoyl]-acetyl]-piperidin-4-yloxy]-acetate as a colourless powder. M.p. 96–102° C. MS (ISP): 463 (M+H)$^+$.

Example 115

By esterifying (Z)-(S)-[1-[2-[4-[amino-hydroxyimino-methyl]-benzyloxy]-propionyl]-piperidin-4-yloxy]-acetic acid with ethanol there is obtained ethyl (Z)-(S)-[1-[2-[4-[amino-hydroxyimino-methyl]-benzyloxy]-propionyl]-piperidin-4-yloxy]-acetate in the form of colourless crystals. $[\alpha]_D^{20}$=–27.3° (c=1, ethanol). M.p. 137–138° C. MS (ISP): 408 (M+H)$^+$.

The starting material can be prepared as follows:
a) Reaction of ethyl L-(–)-lactate with 4-bromomethyl-benzonitrile in DMF in the presence of silver oxide followed by saponification of the product with 1N sodium hydroxide solution gives (S)-2-(4-cyano-benzyloxy)-propionic acid as a light yellow oil. MS (EI): 160 (M—COOH)$^+$.
b) By reacting the product of the preceding step in the same manner as described in Example 112b), c) and d) there is obtained (Z)-(S)-[1-[2-[4-[amino-hydroxyimino-methyl]-benzyloxy]-propionyl]-piperidin-4-yloxy]-acetic acid. MS (ISP): 380 (M+H)$^+$.

Example 116

170 mg of hydroxylamine hydrochloride, 10.8 ml of DMSO and 0.71 ml of triethylamine are stirred at 20° C. for 10min., treated with 578 mg of [1-[4-(4-cyano-phenyl)-4-oxo-butyryl]-piperidin-4-yloxy]-acetate and stirred at 20° C. for 20 hrs. The reaction mixture is diluted with ethyl acetate and the solution is washed with water and saturated sodium chloride solution, dried and evaporated in a vacuum. Chromatography of the residue on silica gel with methylene chloride-alcohol 96:4 gives 343 mg of ethyl (E)/(Z)-[1-[4-[4-(amino-hydroxyimino-methyl)-phenyl]-4-oxo-butyryl]-piperidin-4-yloxy]-acetate, m.p. 166–167° C.

The starting material can be obtained as follows:
a. Tert.-butyl [1-[4-(4-cyano-phenyl)-4-oxo-butyryl]-piperidin-4-yloxy]-acetate (Example 77a) is cleaved in formic acid at 50° C. to [1-[4-(4-cyano-phenyl)-4-oxo-butyryl]-piperidin-4-yloxy]-acetic acid, m.p. 160–165° C.
b. In 5N ethanolic hydrochloric acid there is obtained therefrom ethyl [1-[4-(4-cyano-phenyl)-4-oxo-butyryl]-piperidin-4-yloxy]-acetate, m.p. 79–83° C.

Example 117

In analogy to Example 79, from isopropyl (RS)-[1-[4-[4-(amino-imino-methyl)-phenyl]-2-methyl-4-oxo-butyryl]-piperidin-4-yloxy]-acetate hydrochloride and di-tert.-butyl dicarbonate there is obtained isopropyl (RS)-[1-[4-[4-(tert.-butoxycarbonylamino-imino-methyl)-phenyl]-2-methyl-4-oxo-butyryl]-piperidin-4-yloxy]-acetate as a resinous foam, MS: 518 (100, M+H).

Example 118

279 mg of ethyl (E)/(Z)-[1-[4-[4-(amino-hydroxyimino-methyl)-phenyl]-4-oxo-butyryl]-piperidin-4-yloxy]-acetate, 2.8 ml of DMSO, 140 mg of hydroxylamine hydrochloride and 0.28 ml of triethylamine are stirred at 20° C. for two days. The solution is diluted with ethyl acetate, washed with water and sodium chloride solution, dried and evaporated in a vacuum. Chromatography of the residue on silica gel with hexane-acetone 1:2 gives 207 mg of ethyl [1-[4-[4-(E)/(Z)-(amino-hydroxyimino-methyl)-phenyl]-4-(E)/(Z)-hydroxyimino-butyryl]-piperidin-4-yloxy]-acetate as a resinous foam, MS: 421 (100, M+H).

Example 119

190 mg of ethyl (E)/(Z)-[1-[4-[4-(amino-hydroxyimino-methyl)-phenyl]-4-oxo-butyryl]-piperidin-4-yloxy]-acetate, 3.8 ml of methylene chloride and 0.05 ml of acetic anhydride are stirred at 20° C. for four hours. After the addition of 0.25 ml of ethanol the solution is stirred for a further 20 min. and then evaporated. From ethanol there are obtained 170 mg of ethyl (E)/(Z)-[1-[4-[4-(acetoxyimino-amino-methyl)-phenyl]-4-oxo-butyryl]-piperidin-4-yloxy]-acetate of m.p. 134–135° C.

Example 120

180 mg of ethyl (E)/(Z)-[1-[4-[4-(amino-hydroxyimino-methyl)-phenyl]-4-oxo-butyryl]-piperidin-4-yloxy]-acetate, 3.52 ml of acetone and 0.88 ml of formic acid are stirred at 60° C. for 24 hrs. The reaction mixture is evaporated to dryness and the residue is chromatographed on silica gel with methylene chloride-ethanol 97:3. 152 mg of ethyl [1-[4-[4-(5,5-dimethyl-4,5-dihydro-1,2,4-oxadiazol-3-yl)-phenyl]-4-oxo-butyryl]-piperidin-4-yloxy]-acetate are obtained as a foam. MS: 445 (50, M+H).

Example 121

In analogy to Example 116, from ethyl (R)-[1-[4-(4-cyano-phenyl)-2-methyl-4-oxo-butyryl]-piperidin-4-yloxy]-acetate there is obtained ethyl (R)-(E)/(Z)-[1-[4-[4-(amino-hydroxyimino-methyl)-phenyl]-2-methyl-4-oxo-butyryl]-piperidin-4-yloxy]-acetate, m.p. 172–173° C., $[\alpha]_D^{20}=+83.2°$ (MeOH, c=0.5%).

The starting material can be obtained as follows:
a. By cleaving tert.-butyl 4-piperidinyloxy-acetate in formic acid there is obtained 4-piperidinyloxy-acetic acid, m.p. >270° C.
b. This is converted in 5N ethanolic HCl into the hydrochloride of ethyl 4-piperidinyloxy-acetate, m.p. 104–106° C.
c. From tert.-butyl 3-(4-cyano-phenyl)-3-oxo-propionate and isobutyl (R)-2-trifluoromethylsulphonyloxy-propionate in tetrahydrofuran in the presence of sodium bis-(trimethylsilyl)-amide there is obtained isobutyl 2-(R)-3(R,S)-3-tert.-butoxycarbonyl-4-(4-cyano-phenyl)-2-methyl-4-oxo-butyrate.
d. By heating to 45° C. in formic acid there is obtained therefrom isobutyl (R)-4-(4-cyano-phenyl)-2-methyl-4-oxo-butyrate, $[\alpha]_D^{20}=+21°$ (methanol, c=0.5%).
e. This is saponified in aqueous THF with lithium hydroxyde to (R)-4-(4-cyano-phenyl)-2-methyl-4-oxo-butyric acid. M.p. 125–126° C., $[\alpha]_D^{20}=+37.4°$ (methanol, c=0.5%).
f. By coupling (R)-4-(4-cyano-phenyl)-2-methyl-4-oxo-butyric acid with the hydrochloride of ethyl 4-piperidinyloxy-acetate there is obtained ethyl (R)-[1-[4-(4-cyano-phenyl)-2-methyl-4-oxo-butyryl]-piperidin-4-yloxy]-acetate, m.p. 97–98° C., $[\alpha]_D^{20}=+91.8°$ (methanol, c=0.5%).

Example 122

In analogy to Example 116, from tert.-butyl [1-[4-(4-cyano-phenyl)-4-oxo-butyryl]-piperidin-4-yloxy]-acetate there is obtained tert.-butyl (E)/(Z)-[1-[4-[4-(amino-hydroxyimino-methyl)-phenyl]-4-oxo-butyryl]-piperidin-4-yloxy]-acetate, m.p. 188° C.

Example 123

434 mg of tert.-butyl (R)-[1-[4-[4-(tert.-butoxycarbonylamino-imino-methyl)-phenyl]-2-methyl-4-oxo-butyryl]-piperidin-4-yloxy]-acetate are stiffed at 20° C. for one hour in 4.4 ml of methylene chloride and 4.4 ml of trifluoroacetic acid. The solvent is evaporated, the residue is dissolved in water and the solution is again evaporated. From acetonitrile there crystallize 332 mg of (R)-[1-[4-[4-(amino-imino-methyl)-phenyl]-2-methyl-4-oxo-butyryl]-piperidin-4-yloxy]-acetic acid trifluoroacetate (1:1), m.p. 212° C., $[\alpha]_D^{20}=+69.0°$, (methanol, c=0.5%).

The starting material can be prepared as follows:
a. By coupling (R)-4-(4-cyano-phenyl)-2-methyl-4-oxo-butyric acid with tert.-butyl piperidin-4-yloxy-acetate there is obtained tert.-butyl (R)-[1-[4-(4-cyano-phenyl)-2-methyl-4-oxo-butyryl]-piperidin-4-yloxy]-acetate, m.p. 142° C., $[\alpha]_D^{20}=+83.2°$ (methanol, c=0.5%).
b. With hydrogen sulphide in pyridine/triethylamine there is obtained therefrom tert.-butyl (R)-[1-[2-methyl-4-oxo-4-(4-thiocarbamoyl-phenyl)-butyryl]-piperidin-4-yloxy]-acetate as a yellow resin, MS: 449 (63, M+H), $[\alpha]_D^{20}=+76.4°$ (methanol, c=0.5%).
c. This is converted firstly with methyl iodide in acetone, then with ammonium acetate and acetic acid in methanol and finally with di-tert.-butyl dicarbonate in methylene chloride and aqueous sodium carbonate solution into the starting material; MS: 532 (100, M+H), $[\alpha]_D^{20}=+64.4°$ (methanol, c=0.5%).

Example 124

In analogy to Example 116, from ethyl (RS) [1-[4-(4-cyano-phenyl)-3-methyl-4-oxo-butyryl]-piperidin-4-yloxy]-acetate there is obtained ethyl (E)/(Z)-(RS)-[1-[4-[4-(amino-hydroxyimino-methyl)-phenyl]-3-methyl-4-oxo-butyryl]-piperidin-4-yloxy]-acetate as a foam, MS: 420 (100, M+H).

The starting material can be obtained as follows:
a. (RS)-4-(4-Amino-phenyl)-3-methyl-4-oxo-butyric acid is converted according to Sandmeyer into (RS)-4-(4-cyano-phenyl)-3-methyl-4-oxo-butyric acid, m.p 110–113° C.
b. This is coupled with the hydrochloride of ethyl 4-piperidinyloxy-acetate to give ethyl (RS) [1-[4-(4-cyano-phenyl)-3-methyl-4-oxo-butyryl]-piperidin-4-yloxy]-acetate; MS: 387 (100, M+H).

Example 125

In analogy to Example 116, from pyridin-3-ylmethyl (R)-[1-[4-(4-cyano-phenyl)-2-methyl-4-oxo-butyryl]-piperidin-4-yloxy]-acetate there is obtained pyridin-3-ylmethyl (R)-(E)/(Z)-[1-[4-[4-(amino-hydroxyimino-methyl)-phenyl]-2-methyl-4-oxo-butyryl]-piperidin-4-yloxy]-acetate as a resin, MS: 483 (100, M+H), $[\alpha]_D^{20}=+69.8°$ (methanol, c=0.5%).

The starting material can be obtained in the folllowing manner:
a. tert.-Butyl (R)-[1-[4-(4-cyano-phenyl)-2-methyl-4-oxo-butyryl]-piperidin-4-yloxy]-acetate is cleaved in formic acid to (R)-[1-[4-(4-cyano-phenyl)-2-methyl-4-oxo-butyryl]-piperidin-4-yloxy]-acetic acid, m.p. 185–186°, $[\alpha]_D^{20}=+91.6°$ (methanol, c=0.5%).
b. This is esterified in pyridine in the presence of DCC and pTSOH with 3-pyridylmethanol to pyridin-3-ylmethyl (R)-[1-[4-(4-cyano-phenyl)-2-methyl-4-oxo-butyryl]-piperidin-4-yloxy]-acetate, m.p. 123–124° C., $[\alpha]_D^{20}=+77.6°$ (methanol, c=0.5%).

Example 126

In analogy to Example 78, from ethyl (RS)-[1-[4-[4-(tert.-butoxy-carbonylamino-imino-methyl)-phenyl]-3-methyl-4-oxo-butyryl]-piperidin-4-yloxy]-acetate there is obtained ethyl (RS)-[1-[4-[4-(amino-imino-methyl)-phenyl]-3-methyl-4-oxo-butyryl]-piperidin-4-yloxy]-acetate as the trifluoroacetate (1:1.9), MS: 404 (100, M+H).

The starting material can be obtained as follows:
a. Ethyl (RS) [1-[4-(4-cyano-phenyl)-3-methyl-4-oxo-butyryl]-piperidin-4-yloxy]-acetate in pyridine/triethylamine is converted with hydrogen sulphide into ethyl (RS)-[1-[3-methyl-4-oxo-4-(4-thiocarbamoyl-phenyl)-butyryl]-piperidin-4-yloxy]-acetate. MS: 386 (0.5, M-H$_2$S).

b. This is converted firstly with methyl iodide in acetone, then with ammonium acetate/acetic acid in methanol and finally with di-tert.-butyl dicarbonate in methylene chloride/water/sodium carbonate into ethyl (RS)-[1-[4-[4-(tert.-butoxycarbonylamino-imino-methyl)-phenyl]-3-methyl-4-oxo-butyryl]-piperidin-4-yloxy]-acetate, MS: 504 (100, M+H).

Example 127

200 mg of ethyl (RS)-[1-[4-[4-(amino-imino-methyl)-phenyl]-3-methyl-4-oxo-butyryl]-piperidin-4-yloxy]-acetate trifluoroacetate are stirred in 20 ml of 25 percent hydrochloric acid for 4 hours. The reaction mixture is evaporated to dryness in a vacuum, the residue is taken up in water and again evaporated to dryness. There are obtained 144 mg of (RS)-[1-[4-[4-(amino-imino-methyl)-phenyl]-3-methyl-4-oxo-butyryl]-piperidin-4-yloxy]-acetic acid hydrate (2:3) hydrochloride (8:9), m.p. 173–175° C.

Example 128

In analogy to Example 79, from ethyl (RS)-[1-[4-[4-(amino-imino-methyl)-phenyl]-3-methyl-4-oxo-butyryl]-piperidin-4-yloxy]-acetate trifluoroacetate with isobutyl chloroformate there is obtained ethyl (RS)-[1-[4-[4-(imino-isobutoxycarbonylamino-methyl)-phenyl]-3-methyl-4-oxo-butyryl]-piperidin-4-yloxy]-acetate as a foam, MS: 504 (100, M+H).

Example 129

In analogy to Example 79, from ethyl (R)-[1-[4-[4-(amino-imino-methyl)-phenyl]-2-methyl-4-oxo-butyryl]-piperidin-4-yloxy]-acetate acetate/iodide and ethyl chloroformate there is obtained ethyl (R)-[1-[4 -[4-(ethoxycarbonylamino-imino-methyl)-phenyl]-2-methyl-4-oxo-butyryl]-piperidin-4-yloxy]-acetate as a resin; MS: 476 (36, M+H), $[\alpha]_D^{20}=+72.6°$ (methanol, c=0.5%).

The starting material can be obtained as follows:
a. Ethyl (R)-[1-[4-(4-cyano-phenyl)-2-methyl-4-oxo-butyryl]-piperidin-4-yloxy]-acetate is converted with hydrogen sulphide in pyridine and triethylamine into ethyl (R)-[1-[2-methyl-4-oxo-4-(4-thiocarbamoyl-phenyl)-butyryl]-piperidin-4-yloxy]-acetate, m.p. 171–172° C., $[\alpha]_D^{20}=+88.4°$ (methanol, c=0.5%).
b. By reaction with methyl iodide in acetone and subsequent reaction with ammonium acetate and acetic acid in methanol there is obtained therefrom ethyl (R)-[1-[4-[4-(amino-imino-methyl)-phenyl]-2-methyl-4-oxo-butyryl]-piperidin-4-yloxy]-acetate acetate/iodide.

Example 130

Likewise as in Example 129 there is prepared ethyl (R)-[1-[4-[4-(imino-isobutoxycarbonylamino-methyl)-phenyl]-2-methyl-4-oxo-butyryl]-piperidin-4-yloxy]-acetate. MS: 504 (100, M+H), $[\alpha]_D^{20}=+70.25°$ (methanol, c=0.4%).

Example 131

In analogy to Example 116, from pyridin-4-ylmethyl (R)-[1-[4-(4-cyano-phenyl)-2-methyl-4-oxo-butyryl]-piperidin-4-yloxy]-acetate there is obtained pyridin-4-ylmethyl (R)-(E)/(Z)-[1-[4-[4-(amino-hydroxyimino-methyl)-phenyl]-2-methyl-4-oxo-butyryl]-piperidin-4-yloxy]1-acetate as a resin, MS: 483 (100, M+H), $[\alpha]_D^{20}=+71.8°$ (methanol, c=0.5%).

The starting material is obtained from (R)-[1-[4-(4-cyano-phenyl)-2-methyl-4-oxo-butyryl]-piperidin-4-yloxy]-acetic acid and 4-pyridyl-methanol in pyridine in the presence of DCC and pTSOH. M.p. 99–104° C., $[\alpha]_D^{20}=+69.8°$ (methanol, c=0.5%).

Example 132

In analogy to Example 116, from tert-butyl (RS)-3-[1-[(R)-4-(4-cyano-phenyl)-2-methyl-4-oxo-butyryl]-piperidin-4-yloxy-acetoxymethyl]-piperidine-1-carboxylate there is obtained tert-butyl (E)- or (Z)-(RS)-3-[1-[(R)-4-[4-(amino-hydroxyimino-methyl)-phenyl]-2-methyl-4-oxo-butyryl]-piperidin-4-yloxyacetoxymethyl]-piperidine-1-carboxylate; MS: 589 (100, M+H), $[\alpha]_D^{20}=+60°$ (methanol, c=0.5%).

The starting material is obtained from (R)-[1-[4-(4-cyano-phenyl)-2-methyl-4-oxo-butyryl]-piperidin-4-yloxy]-acetic acid and tert-butyl (RS)-3-(hydroxymethyl)-piperidine-1-carboxylate in pyridine in the presence of DCC and pTSOH. MS: 556 (100, M+H), $[\alpha]_D^{20}=+56°$ (methanol, c=0.5%).

Example 133

Likewise as described in Example 129 there is prepared ethyl (R)-[1-4-[4-(imino-isopropoxycarbonylamino-methyl)-phenyl]-2-methyl-4-oxo-butyryl]-piperidin-4-yloxyl-acetate. MS: 490 (100, M+H), $[\alpha]_D^{20}=+72°$ (methanol, c=0.4%).

Example 134

In analogy to Example 78, from ethyl (R)-[1-[4-[4-(tert-butoxy-carbonylamino-imino-methyl)-phenyl]-2-methyl-4-oxo-butyryl]-piperidin-4-yloxy]-acetate there is obtained ethyl (R)-[1-[4-[4-(amino-imino-methyl)-phenyl]-2-methyl-4-oxo-butyryl]-piperidin-4-yloxy]-acetate trifluoroacetate, m.p. 186° C., $[\alpha]_D^{20}=+67.4°$ (methanol, c=0.5%).

The starting material is obtained from ethyl (R)-[1-[4-[4-(amino-imino-methyl)-phenyl]-2-methyl-4-oxo-butyryl]-piperidin-4-yloxy]-acetate acetate/iodide and di-tert-butyl dicarbonate in methylene chloride/water/$Na_2CO_3$; MS: 504 (91, M+H), $[\alpha]_D^{20}=+66°$ (methanol, c=0.5%).

Example 135

259 mg of ethyl (R)-[1-[4-[4-(amino-imino-methyl)-phenyl]-2-methyl-4-oxo-butyryl]-piperidin-4-yloxy]-acetate trifluoroacetate, 3.9 ml of DMF, 0.14 ml of triethylamine and 159 mg of 4-nitrophenoxycarbonyloxymethyl benzoate are stirred at room temperature for three hours. The reaction mixture is evaporated to dryness in a vacuum. Chromatography of the residue on silica gel with methylene chloride-isopropanol 19:1 gives 223 mg of ethyl (R)-[1-[4-[4-(benzoyloxymethoxycarbonylamino-imino-methyl)-phenyl]-2-methyl-4-oxo-butyryl]-piperidin-4-yloxy]-acetate, MS: 582 (100, M+H), $[\alpha]_D^{20}=+67.4°$ (methanol, c=0.5%).

The 4-nitrophenoxycarbonyloxymethyl benzoate can be obtained from iodomethyl 4-nitrophenyl carbonate and silver benzoate in boiling benzene.

Example 136

Likewise as described in Example 135, from ethyl (R)-[1-[4-[4-(amino-imino-methyl)-phenyl]-2-methyl-4-oxo-butyryl]-piperidin-4-yloxy]-acetate trifluoroacetate with 4-nitrophenoxycarbonyloxymethyl pivalate there is obtained ethyl (R)-[1-[4-[4-(imino-pivaloyloxymethoxy-carbonylamino-methyl)-phenyl]-2-methyl-4-oxo-butyryl]-piperidin-4-yloxy]-acetate as a foam, MS: 562 (100, M+H), $[\alpha]_D^{20}=+60.8°$ (methanol, c=0.5%).

The 4-nitrophenoxycarbonyloxymethyl pivalate can be obtained from iodomethyl 4-nitrophenyl carbonate and silver pivalate in boiling benzene.

Example 137

In analogy to Example 116, from 2-(pyridin-2-yl)-ethyl (R)-[1-[4-(4-cyano-phenyl)-2-methyl-4-oxo-butyryl]-piperidin-4-yloxy]-acetate there is obtained 2-(pyridin-2-yl)-ethyl (R)-(E)/(Z)-[1-[4-[4 -(amino-hydroxyimino-methyl)-phenyl]-2-methyl-4-oxo-butyryl]-piperidin-4-yloxy]-acetate, MS: 497 (100, M+H), $[\alpha]_D^{20}$=+67° (methanol, c=0.5%).

The starting material is obtained from (R)-[1-[4-(4-cyano-phenyl)-2-methyl-4-oxo-butyryl]-piperidin-4-yloxy]-acetic acid and 2-(pyridin-2-yl)-ethanol in pyridine in the presence of DCC and pTSOH. MS: 464 (100, M+H), $[\alpha]_D^{20}$=+72.8° (methanol, c=0.5%).

Example 138

In analogy to Example 116, from 2-(pyridin-3-yl)-ethyl (R)-[1-[4-(4-cyano-phenyl)-2-methyl-4-oxo-butyryl]-piperidin-4-yloxy]-acetate there is obtained 2-(pyridin-3-yl)-ethyl (R)-(E)/(Z)-[1-[4-[4-(amino-hydroxyimino-methyl)-phenyl]-2-methyl-4-oxo-butyryl]-piperidin-4-yloxy]-acetate, MS: 497 (100, M+H), $[\alpha]_D^{20}$=+65.8° (methanol, c=0.5%).

The starting material is obtained from (R)-[1-[4-(4-cyano-phenyl)-2-methyl-4-oxo-butyryl]-piperidin-4-yloxy]-acetic acid and 2-(pyridin-3-yl)-ethanol in pyridine in the presence of DCC and pTSOH. MS: 464 (100, M+H), $[\alpha]_D^{20}$=+70.8° (methanol, c=0.5%).

Example 139

In analogy to Example 78, from tert-butyl (E)- or (Z)-(RS)-3-[1-[(R)-4-[4-(amino-hydroxyimino-methyl)-phenyl]-2-methyl-4-oxo-butyryl]-piperidin-4-yloxyacetoxymethyl]-piperidine-1-carboxylate there is obtained (RS)-piperidin-3-yl-methyl (E) or (Z)-(R)-[1-[4-[4-(amino-hydroxyimino-methyl)-phenyl]-2-methyl-4-oxo-butyryl]-piperidin-4-yloxy-acetate as the trifluoroacetate (1:2), MS: 489 (100, M+H), $[\alpha]_D^{20}$=+45.75° (methanol, c=0.4%).

Example 140

In analogy to Example 116, from tert-butyl (R)-4-([1-[4-(4-cyano-phenyl)-2-methyl-4-oxo-butyryl]-piperidin-4-yloxy]-acetoxymethyl]-piperidine-1-carboxylate there is obtained tert-butyl (E)- or (Z)-(R)-4-[1-[4-[4-(amino-hydroxyimino-methyl)-phenyl]-2-methyl-4-oxo-butyryl]-piperidin-4-yloxyacetoxymethyl]-piperidine-1-carboxylate; MS: 589 (100, M+H), $[\alpha]_D^{20}$=+58.6° (methanol, c=0.5%).

The starting material is obtained from (R)-[1-[4-(4-cyano-phenyl)-2-methyl-4-oxo-butyryl]-piperidin-4-yloxy]-acetic acid and tert-butyl 4-(hydroxymethyl)-piperidine-1-carboxylate in pyridine in the presence of DCC and pTSOH. MS: 556 (100, M+H), $[\alpha]_D^{20}$=+63.3° (methanol, c=0.3%).

Example 141

In analogy to Example 78, from tert-butyl (E)- or (Z)-(R)-4-[1-[4-[4-(amino-hydroxyimino-methyl)-phenyl]-2-methyl-4-oxo-butyryl]-piperidin-4-yloxyacetoxymethyl]-piperidine-1-carboxylate there is obtained piperidin-4-yl-methyl (E) or (Z) -(R)-[1-[4-[4-(amino-hydroxyimino-methyl)-phenyl]-2-methyl-4-oxo-butyryl]-piperidin-4-yloxy]-acetate as the trifluoroacetate (1:3), MS: 489 (100, M+H), $[\alpha]_D^{20}$=+41.5° (methanol, c=0.4%).

Example 142

In analogy to Example 116, from 2-(pyridin-4-yl)-ethyl (R)-[1-[4-(4-cyano-phenyl)-2-methyl-4-oxo-butyryl]-piperidin-4-yloxy]-acetate there is obtained 2-(pyridin-4-yl)-ethyl (E)/(Z)-(R)-[1-[4-[4-(amino-hydroxyimino-methyl)-phenyl]-2-methyl-4-oxo-butyryl]-piperidin-4yloxy]-acetate, MS: 497 (100, M+H), $[\alpha]_D^{20}$=+67° (methanol, c=0.5%).

The starting material is obtained from (R)-[1-[4-(4-cyano-phenyl)-2-methyl-4-oxo-butyryl]-piperidin-4-yloxy]-acetic acid and 2-(pyridin-4-yl)-ethanol in pyridine in the presence of DCC and pTSOH.

Example 143

In analogy to Example 116, from (R)-1-phenyl-ethyl (R)-[1-[4-(4-cyano-phenyl)-2-methyl-4-oxo-butyryl]-piperidin-4-yloxy]-acetate there is obtained (R)-1-phenyl-ethyl (E)/(Z)-(R)-[1-[4-[4-(amino-hydroxyimino-methyl)-phenyl]-2-methyl-4-oxo-butyryl]-piperidin-4-yloxy]-acetate, m.p. 94° C., $[\alpha]_D^{20}$=+111.6° (methanol, c=0.5%).

The starting material is obtained from (R)-[1-[4-(4-cyano-phenyl)-2-methyl-4-oxo-butyryl]-piperidin-4-yloxy]-acetic acid and (R)-1-phenyl-ethanol in pyridine in the presence of DCC and pTSOH; $[\alpha]_D^{20}$=+96.6° (methanol, c=0.5%).

Example 144

In analogy to Example 116, from (S)-1-phenyl-ethyl (R)-[1-[4-(4-cyano-phenyl)-2-methyl-4-oxo-butyryl]-piperidin-4-yloxy]-acetate there is obtained (S)-1-phenyl-ethyl (E)/(Z)-(R)-[1-[4-[4-(amino-hydroxyimino-methyl)-phenyl]-2-methyl-4-oxo-butyryl]-piperidin-4-yloxy]-acetate, m.p. 127° C., $[\alpha]_D^{20}$=+32.8° (methanol, c=0.5%).

The starting material is obtained from (R)-[1-[4-(4-cyano-phenyl)-2-methyl-4-oxo-butyryl]-piperidin-4-yloxy]-acetic acid and (S)-1-phenyl-ethanol in pyridine in the presence of DCC and pTSOH; m.p. 98° C., $[\alpha]_D^{20}$=+33.8° (methanol, c=0.5%).

Example 145

In analogy to Example 116, from (S)-1-(pyridin-4-yl)-ethyl (R)-[1-[4-(4-cyano-phenyl)-2-methyl-4-oxo-butyryl]-piperidin-4-yloxy]-acetate there is obtained (S)-i-(pyridin-4-yl)-ethyl (E)/(Z)-(R)-[1-[4-[4-(amino-hydroxyimino-methyl)-phenyl]-2-methyl-4-oxo-butyryl]-piperidin-4-yloxy]-acetate, $[\alpha]_D^{20}$=+41° (methanol, c=0.5%).

The starting material is obtained from (R)-[1-[4-(4-cyano-phenyl)-2-methyl-4-oxo-butyryl]-piperidin-4-yloxy]-acetic acid and (S)-1-(4-pyridyl)-ethanol in pyridine in the presence of DCC and pTSOH; m.p. 115° C., $[\alpha]_D^{20}$=+45.8° (methanol, c=0.5%).

Example 146

In analogy to Example 116, from (R)-1-(pyridin-4-yl)-ethyl (R)-[1-[4-(4-cyano-phenyl)-2-methyl-4-oxo-butyryl]-piperidin-4-yloxy]-acetate there is obtained (R)-1-(pyridin-4-yl)-ethyl (E)/(Z)-(R)-[1-[4-[4 -(amino-hydroxyimino-methyl)-phenyl]-2-methyl-4-oxo-butyryl]-piperidin-4-yloxyl-acetate, MS: 497 (100, M+H), $[\alpha]_D^{20}$=+96.8° (methanol, c=0.5%).

The starting material is obtained from (R)-[1-[4-(4-cyano-phenyl)-2-methyl-4-oxo-butyryl]-piperidin-4-yloxy]-acetic acid and (R)-1-(4-pyridyl)-ethanol in pyridine in the presence of DCC and pTSOH; m.p. 115° C., $[\alpha]_D^{20}$=+112.4° (methanol, c=0.5%).

Example 147

In analogy to Example 116, from methyl (R)-[1-[4-(4-cyano-phenyl)-2-methyl-4-oxo-butyryl]-piperidin-4-yloxy]-acetate there is obtained methyl (E)/(Z)-(R)-[1-[4-[4-(amino-hydroxyimino-methyl)-phenyl]-2-methyl-4-oxo-butyryl]-piperidin-4-yloxy]-acetate, m.p. 147–149° C., $[\alpha]_D^{20}$=+86° (methanol, c=0.5%).

The starting material is obtained from (R)-[1-[4-(4-cyano-phenyl)-2-methyl-4-oxo-butyryl]-piperidin-4-yloxy]-acetic acid and methanol in pyridine in the presence of DCC and pTSOH as the (2:1) adduct with dicyclohexylurea, m.p. 101° C., $[\alpha]_D^{20}$=+76.2° (methanol, c=0.5%).

Example 148

In analogy to Example 79, from methyl (R)-[1-[4-[4-(amino-imino-methyl)-phenyl]-2-methyl-4-oxo-butyryl]-piperidin-4-yloxy]-acetate acetate/iodide and methyl chloroformate there is obtained methyl (R)-[1-[4-[4-(imino-methoxycarbonylamino-methyl)-phenyl]-2-methyl-4-oxo-butyryl]-piperidin-4-yloxy]-acetate, MS: 448 (100, M+H), $[\alpha]_D^{20}$=+75.4° (methanol, c=0.5%).

The starting material can be prepared as follows:
a. Methyl (R)-[1-[4-(4-cyano-phenyl)-2-methyl-4-oxo-butyryl]-piperidin-4-yloxy]-acetate is converted with hydrogen sulphide in pyridine and triethylamine into methyl (R)-[1-[2-methyl-4-oxo-4-(4-thiocarbamoyl-phenyl)-butyryl]-piperidin-4-yloxy]-acetate, m.p. 172–177° C.
b. By reaction with methyl iodide in acetone and subsequent reaction with ammonium acetate and acetic acid in methanol there is obtained therefrom methyl (R)-[1-[4-[4-(amino-imino-methyl)-phenyl]-2-methyl-4-oxo-butyryl]-piperidin-4-yloxy]-acetate acetate/iodide.

Example 149

In analogy to Example 79, from methyl (R)-[1-[4-[4-(amino-imino-methyl)-phenyl]-2-methyl-4-oxo-butyryl]-piperidin-4-yloxy]-acetate acetate/iodide and ethyl chloroformate there is obtained methyl (R)-[1-[4-[4-(ethoxycarbonylamino-imino-methyl)-phenyl]-2-methyl-4-oxo-butyryl]-piperidin-4-yloxy]-acetate, MS: 462 (100, M+H), $[\alpha]_D^{20}$=+66° (methanol, c=0.5%).

Example 150

214 mg of a mixture of pyridin-3-ylmethyl (R)-[1-[4-[4-[tert-butoxycarbonylimino-(isobutoxycarbonyl-tert-butoxycarbonyl-amino)-methyl]-phenyl]-2-methyl-4-oxo-butyryl]-piperidin-4-yloxy]-acetate and pyridin-3-ylmethyl (R)-[1-[4-[4-[(di-tert-butoxycarbonyl-amino)-isobutoxycarbonylimino-methyl]-phenyl]-2-methyl-4-oxo-butyryl]-piperidin-4-yloxy]-acetate are stirred at 20° C. for 2 hrs. in 1.2 ml of methylene chloride and 1.2 ml of trifluoroacetic acid. The solvent is evaporated in a vacuum, the residue is dissolved in ethyl acetate and washed in succession with dilute NaHCO$_3$ solution, water and saturated NaCl solution, dried and evaporated in a vacuum. There are obtained 151 mg of pyridin-3-ylmethyl (R)-[1-[4-[4-(imino-isobutoxycarbonylamino-methyl)-phenyl]-2-methyl-4-oxo-butyryl]-piperidin-4-yloxy]-acetate as a foam, MS: 567 (100, M+H), $[\alpha]_D^{20}$=+61° (methanol, c=0.2%).

The starting material can be obtained as follows:
a. Ethyl (R)-[1-[4-[4-(imino-isobutoxycarbonylamino-methyl)-phenyl]-2-methyl-4-oxo-butyryl]-piperidin-4-yloxy]-acetate is converted in acetonitrile in the presence of 4-dimethylamino-pyridine with di-tert-butyl dicarbonate into a mixture of ethyl (R)-[1-[4-[4-[tert-butoxycarbonylimino-(isobutoxycarbonyl-tert-butoxycarbonyl-amino)-methyl]-phenyl]-2-methyl-4-oxo-butyryl]-piperidin-4-yloxy]-acetate and ethyl (R)-[1-[4-[4-[(di-tert-butoxycarbonyl-amino)-isobutoxycarbonylimino-methyl]-phenyl]-2-methyl-4-oxo-butyryl]-piperidin-4-yloxy]-acetate.
b. By saponification with LiOH in aqueous THF there is obtained therefrom a mixture of (R)-[1-[4-[4-[tert-butoxycarbonylimino-(isobutoxycarbonyl-tert-butoxycarbonyl-amino)-methyl]-phenyl]-2-methyl-4-oxo-butyryl]-piperidin-4-yloxy]-acetic acid and (R)-[1-[4-[4-[(di-tert-butoxycarbonyl-amino)-isobutoxycarbonylimino-methyl]-phenyl]-2-methyl-4-oxo-butyryl]-piperidin-4-yloxy]-acetic acid.
c. This is converted in pyridine with 3-hydroxymethyl-pyridine, DCC and p-TsOH into a mixture of pyridin-3-ylmethyl (R)-[1-[4-[4-[tert-butoxycarbonylimino-(isobutoxycarbonyl-tert-butoxycarbonyl-amino)-methyl]-phenyl]-2-methyl-4-oxo-butyryl]-piperidin-4-yloxy]-acetate and pyridin-3-ylmethyl (R)-[1-[4-[4-[(di-tert-butoxycarbonyl-amino)-isobutoxycarbonylimino-methyl]-phenyl]-2-methyl-4-oxo-butyryl]-piperidin-4-yloxy]-acetate.

Example 151

In analogy to Example 79, from tert-butyl (RS)-3-[[1-[(R)-4-[4-(amino-imino-methyl)-phenyl]-2-methyl-4-oxo-butyryl]-piperidin-4-yloxy]-acetoxymethyl]-piperidine-1-carboxylate acetate/iodide and methyl chloroformate there is obtained tert-butyl (RS)-3-[[1-[(R)-4-[4-(Imino-methoxycarbonylamino-methyl)-phenyl]-2-methyl-4-oxo-butyryl]-piperidin-4-yloxy]-acetoxymethyl]-piperidine-1-carboxylate, MS: 631 (100, M+H), $[\alpha]_D^{20}$=+57.2° (methanol, c=0.5%).

The starting material can be obtained as follows:
a. tert-Butyl (RS)-3-[1-[(R)-4-(4-cyano-phenyl)-2-methyl-4-oxo-butyryl]-piperidin-4-yloxy-acetoxymethyl]-piperidine-1-carboxylate is converted with H$_2$S in pyridine and triethylamine into tert-butyl (RS)-3 -[[1-[(R)-2-methyl-4-oxo-4-(4-thiocarbamoyl-phenyl)-butyryl]-piperidin-4-yloxy]-acetoxymethyl]-piperidine-1-carboxylate; MS: 590 (100, M+H), $[\alpha]_D^{20}$=+58.8° (methanol, c=0.5%).
b. By reaction with methyl iodide in acetone and subsequent reaction with ammonium acetate and acetic acid in methanol there is obtained tert-butyl (RS)-3-[[1-[(R)-4-[4-(amino-imino-methyl)-phenyl]-2-methyl-4-oxo-butyryl]-piperidin-4-yloxy]acetoxymethyl]-piperidine-1-carboxylate acetate/iodide.

Example 152

In analogy to Example 79, from tert-butyl (RS)-3-[[1-[(R)-4-[4-(amino-imino-methyl)-phenyl]-2-methyl-4-oxo-butyryl]-piperidin-4-yloxy]acetoxymethyl]-piperidine-1-carboxylate acetate/iodide and ethyl chloroformate there is obtained tert-butyl (RS)-3-[[1-[(R)-4-[4-(ethoxycarbonylamino-imino-methyl)-phenyl]-2-methyl-4-oxo-butyryl]-piperidin-4-yloxy]-acetoxymethyl]-piperidine-1-carboxylate, MS: 645 (100, M+H), $[\alpha]_D^{20}$=+56.2° (methanol, c=0.5%).

Example 153

In analogy to Example 79, from ethyl (R)-[1-[4-[4-(amino-imino-methyl)-phenyl]-2-methyl-4-oxo-butyryl]-piperidin-4-yloxy]-acetate acetate/iodide and methyl chloroformate there is obtained ethyl (R)-[1-[4-[4-(imino-methoxycarbonylamino-methyl)-phenyl]-2-methyl-4-oxo-butyryl]-piperidin-4-yloxy]-acetate.

Example 154

In analogy to Example 116, from ethyl [4-[4-(4-cyano-phenyl)-4-oxo-butyryl]-phenoxy]-acetate there is obtained ethyl (E)/(Z)-[4-[4-[4-(amino-hydroxyimino-methyl)-phenyl]-4-oxo-butyryl]-phenoxy]-acetate, m.p. 174–175° C.

Example 155

In analogy to Example 116, from ethyl (RS)-[4-[4-(4-cyano-phenyl)-2-methyl-4-oxo-butyryl]-phenoxy]-acetate there is obtained ethyl (E)/(Z)-RS)-[4-[4-[4-(amino-hydroxyimino-methyl)-phenyl]-2-methyl-4-oxo-butyryl]-phenoxy]-acetate, m.p. 166–167° C.

The starting material can be prepared as follows:
a. From ethyl [4-(1-oxo-propyl)-phenoxy]-acetate and bromine in acetic acid there is obtained ethyl (RS)-[4-(2-bromo-1-oxo-propyl)-phenoxy]-acetate, m.p. 72–76° C.
b. This is converted in acetone in the presence of sodium bis-(trimethylsilyl)-amide with tert.-butyl 3-(4-cyano-phenyl)-3-oxo-propionate into ethyl [4-[3-tert.-butoxycarbonyl-3-(4-cyanobenzoyl)-2-methyl-propionyl]-phenoxy]-acetate (racemic diastereomer mixture); MS: 406 (1.7, M—COOC$_2$H$_5$).
c. In formic acid there is obtained therefrom ethyl (RS)-[4-[4-(4-cyano-phenyl)-2-methyl-4-oxo-butyryl]-phenoxy]-acetate, m.p. 117–123° C.

Example 156

365 mg of ethyl [4-[4-(4-cyano-phenyl)-4-oxo-butyryl]-phenoxy]-acetate are stirred at 20° C. for 4 days in 20 ml of 0.1 N ethanolic hydroxylamine solution. The reaction mixture is concentrated in a vacuum, diluted with ethyl acetate and washed with water and saturated sodium chloride solution. The ethyl acetate solution is dried over Na$_2$SO$_4$ and evaporated in a vacuum. Chromatography on silica gel with CH$_2$Cl$_2$-ethanol 98:2 gives 111 mg of ethyl [4-[(E)/(Z)-4-[(E)/(Z)-4-(amino-hydroxyimino-methyl)-phenyl]-1-hydroxyimino-4-oxo-butyl]-phenoxy]-acetate, m.p. 180–181° C.

Example 157

84 mg [4-[4-[4-(tert-butoxycarbonylamino-imino-methyl)-phenyl]-4-oxo-butyryl]-phenoxy]-acetic acid and 1.7 ml of formic acid are stirred at 20° C. for seven hours. The reaction mixture is evaporated, the residue is taken up in water and again evaporated. The solid residue is suspended in water, adjusted to pH 8 with ammonia, filtered off under suction, washed with water and dried. There are obtained 50 mg of [4-[4-(amino-imino-methyl)-phenyl]-4-oxo-butyryl]-phenoxy]-acetic acid, m.p. 284° C.

The starting material can be obtained as follows:
a. Ethyl [4-[4-[4-(amino-imino-methyl)-phenyl]-4-oxo-butyryl]-phenoxy]-acetate (1:1) in CH$_2$Cl$_2$ and water is converted with di-tert-butyl dicarbonate in the presence of Na$_2$CO$_3$ into ethyl [4-[4-[4-(tert-butoxycarbonylamino-imino-methyl)-phenyl]-4-oxo-butyryl]-phenoxy]-acetate, m.p. 164° C.
b. By saponification with NaOH in EtOH there is obtained therefrom [4-[4-[4-(tert-butoxycarbonylamino-imino-methyl)-phenyl]-4-oxo-butyryl]-phenoxy]-acetic acid, m.p. 284° C. (dec.).

Example 158

278 mg of hydroxylamine hydrochloride, 4 ml of DMSO and 0.56 ml of triethylamine are stirred at 20° C. for 10 min. After the addition of 146 mg of ethyl [4-[4-(4-cyano-phenyl)-4-oxo-butyryl]-phenoxy]-acetate the mixture is stirred at 20° C. for 3 days. The reaction mixture is diluted with ethyl acetate, washed with water and sodium chloride solution, dried and evaporated. Chromatography on silica gel with CH$_2$Cl$_2$—EtOH 9:1 gives 42 mg of ethyl [4-[4-[4-(amino-hydroxyimino-methyl)-phenyl]-1,4-bis-hydroxyimino-butyl]-phenoxy]-acetate (all oxime: E or Z), m.p. 210° C. (dec.).

Example 159

In analogy to Example 116, from ethyl (RS)-[4-[2-(2-acetoxy-ethyl)-4-(4-cyano-phenyl)-4-oxo-butyryl]-phenoxy]-acetate there is obtained ethyl (E/Z)-(RS)-[4-[2-(2-acetoxy-ethyl)-4-[4-(amino-hydroxyimino-methyl)-phenyl]-4-oxo-butyryl]-phenoxy]-acetate as a colourless resin, MS: 485 (100, M+H).

The starting material can be prepared as follows:
a. From 4-hydroxy-1-(4-hydroxy-phenyl)-butan-1-one and ethyl bromoacetate in acetone in the presence of K$_2$CO$_3$ there is obtained ethyl [4-(4-hydroxy-butyryl)-phenoxy]-acetate, m.p. 64–66° C.
b. With acetic anhydride in pyridine there is obtained therefrom ethyl [4-(4-acetoxy-butyryl)-phenoxy]-acetate, m.p. 94–96° C.
c. This is converted with bromine in acetic acid into ethyl [4-(4-acetoxy-2-bromo-butyryl)-phenoxy]-acetate.
d. The latter is converted in acetone in the presence of sodium bis-(trimethylsilyl)-amide with tert.-butyl 3-(4-cyano-phenyl)-3-oxo-propionate into tert.-butyl 5-acetoxy-2-(4-cyano-benzoyl)-3-(4-ethoxycarbonylmethoxy-benzoyl)-pentanoate (racemic diastereomer mixture), MS: 478 (0.2, M—CO$_2$Et).
e. By heating in formic acid to 40° C. and subsequent chromatography there is obtained therefrom ethyl (RS)-[4-[2-(2-acetoxy-ethyl)-4-(4-cyano-phenyl)-4-oxo-butyryl]-phenoxy]-acetate, m.p. 102–104° C.

Example 160

425 mg of ethyl (RS)-[4-[4-[4-(tert-butoxycarbonylamino-imino-methyl)-phenyl]-2-methyl-4-oxo-butyryl]-phenoxy]-acetate are heated to 40° C. in 40 ml of acetic acid for 2.5 hours. The reaction mixture is evaporated to dryness in a vacuum. From ethyl acetate-ether there are obtained 239 mg of ethyl (RS)-[4-[4-[4-(amino-imino-methyl)-phenyl]-2-methyl-4-oxo-butyryl]-phenoxy]-acetate as the acetate (1:1), m.p. 198° C.

The starting material can be obtained as follows:
a. Ethyl (RS)-[4-[4-(4-cyano-phenyl)-2-methyl-4-oxo-butyryl]-phenoxy]-acetate is converted with H$_2$S in pyridine and triethylamine into ethyl (RS)-[4-[2-methyl-4-oxo-4-(4-thiocarbamoyl-phenyl)-butyryl]-phenoxy]-acetate, m.p. 112–113° C.
b. This is converted firstly with methyl iodide in acetone, subsequently with ammonium acetate and acetic acid in methanol and finally with di-tert.-butyl dicarbonate in methylene chloride/water/Na$_2$CO$_3$ into ethyl (RS)-[4-[4-[4-(tert-butoxycarbonylamino-imino-methyl)-phenyl]-2-methyl-4-oxo-butyryl]-phenoxy]-acetate; MS: 497 (100, M+H).

Example 161

In analogy to Example 79, from ethyl (RS)-[4-[4-[4-(amino-imino-methyl)-phenyl]-2-methyl-4-oxo-butyryl]-phenoxy]-acetate and isobutyl chloroformate there is obtained ethyl (RS)-[4-[4-[4-(imino-isobutoxy-carbonylamino-methyl)-phenyl]-2-methyl-4-oxo-butyryl]-phenoxy]-acetate as a resin. MS: 497 (100, M+H).

Example 162

In analogy to Example 160, from ethyl (RS)-[4-[2-(2-acetoxy-ethyl)-4-[4-(tert.-butoxycarbonylamino-imino-methyl)-phenyl]-4-oxo-butyryl]-phenoxy]-acetate there is obtained ethyl (RS)-[4-[2-(2-acetoxy-ethyl)-4-[4-(amino-imino-methyl)-phenyl]-4-oxo-butyryl]-phenoxy]-acetate as the acetate (1:1), m.p. 183° C.

The starting material can be obtained as follows:
a. From ethyl (RS)-[4-[2-(2-acetoxy-ethyl)-4-(4-cyano-phenyl)-4-oxo-butyryl]-phenoxy]-acetate with $H_2S$ in pyridine and triethylamine there is obtained ethyl (RS)-[4-[2-(2-acetoxy-ethyl)-4-oxo-4-(4-thiocarbamoyl-phenyl)-butyryl]-phenoxy]-acetate, MS: 508 (100, M+Na).
b. This is converted firstly with methyl iodide in acetone, subsequently with ammonium acetate and acetic acid in methanol and finally with di-tert.-butyl dicarbonate in methylene chloride/water/$Na_2CO_3$ into ethyl (RS)-[4-[2-(2-acetoxy-ethyl)-4-[4-(tert.-butoxycarbonylamino-imino-methyl)-phenyl]-4-oxo-butyryl]-phenoxy]-acetate, MS: 569 (100, M+H).

Example 163

A solution of 413 mg of ethyl (Z)-(S)-[4-[2-[4-(amino-hydroxyimino-methyl)-benzoylaminol-propionyl]-phenoxy]-acetate and 120 mg of 4-ethylmorpholine in 10 ml of dichloromethane is treated with 98 mg of triphosgene in 10ml of dichloromethane at 0° C. stirred at room temperature for 2 h. The reaction solution is washed with water, dried and concentrated. The residue is suspended in ether and filtered off under suction. There are obtained 50 mg of ethyl (S)-[4-[2-[4-(5-Oxo-4,5-dihydro-1,2,4-oxadiazol-3-yl)-benzoylamino]-propionyl]-phenoxy]-acetate, MS (ISP): 440 (M+H)$^+$.

Example 164

A solution of 120 mg of S-ethyl-chlorothioformate in 2 ml of dichloromethane is added to a suspension of 650 mg of ethyl (S)-4-[2-[4-(amino-imino-methyl)-benzoylamino]-propionyl]-phenoxyacetate trifluoroacetate in 10 ml of dichloromethane and 10 ml of saturated $NaHCO_3$ solution and the mixture is subsequently stirred at room temperature for 47 h. The aqueous phase is extracted with dichloromethane, the dichloromethane phases are washed with water, dried and concentrated. After chromatography of the residue on silica gel (hexane/ethyl acetate 1:2) there are obtained 230 mg of ethyl (S)-[4-[2-[4-(amino-ethylsulphanylcarbonylimino-methyl)-benzoylamino]-propionyl]-phenoxy]-acetate, $[\alpha]_D^{20}$=+75.1° (c=0.7, chloroform).

Example 165

A solution of 190 mg of ethyl (S)-4-[2-[4-[(amino-(2-tert-butyl-dimethylsilanyloxy-ethoxycarbonylimino)-methyl]-benzoylamino]-propionyl]-phenoxy-acetate in 10 ml of tetrahydrofuran is treated at −20° C. with 0.3 ml of tetrabutylammonium fluoride (1M in tetrahydrofuran) and stirred at room temperature for 2 h. The reaction mixture is diluted with ethyl acetate, extracted with water, dried and concentrated. Chromatography of the residue on silica gel (ethyl acetate/5% ethanol) gives 56 mg of ethyl (S)-[4-[2-[4-[amino-(2-hydroxy-ethoxycarbonylimino)-methyl]-benzoylamino]-propionyl]-phenoxy]-acetate, MS (ISP): 486 (M+H)$^+$.

The starting material can be prepared as follows:

98 mg of triphosgene dissolved in 4 ml of dichloromethane are added at 0° C. to a solution of 230 mg of 2-(tert-butyl-dimethyl-silanyloxy)-ethanol and 101 mg of 4-methylmorpholine in 8 ml of dichloromethane and the mixture is stirred at room temperature for 2 h. The reaction solution is subsequently added to a suspension of 510 mg of ethyl (S)-4-[2-[4-(amino-imino-methyl)-benzoylamino]-propionyl]-phenoxyacetate trifluoroacetate in 10 ml of dichloromethane and 10 ml of saturated $Na_2CO_3$ solution. After stirring at room temperature for 10 min. the phases are separated, the organic phase is washed with water, dried and concentrated. Chromatography of the residue on silica gel (hexane/ethyl acetate 1:2) gives 200 mg of ethyl (S)-[4-[2-[4-[(amino-(2-tert-butyl-dimethylsilanyloxy-ethoxycarbonylimino)-methyl]-benzoyl-amino]-propionyl]-phenoxy]-acetate, Rf=0.73 (ethyl acetate).

Example 166

In analogy to Example 165 a), from 511 mg of ethyl (S)-4-[2-[4-(amino-imino-methyl)-benzoylamino]-propionyl]-phenoxyacetate trifluoroacetate and 104 mg of 2-acetoxyethanol there are obtained after chromatography on silica gel (hexane/ethyl acetate 1:4) 75 mg of ethyl (S)-[4-[2-[4-[(2-acetoxy-ethoxycarbonylimino)-amino-methyl]-benzoylamino]-propionyl]-phenoxy]-acetate, MS (ISP): 528 (M+H)$^+$.

Example 167

In analogy to Example 165 a), from 511 mg of ethyl (S)-4-[2-[4-amino-imino-methyl)-benzoylamino]-propionyl]-phenoxyacetate trifluoroacetate and 118 mg of 2-hydroxy-ethyl propionate there are obtained after chromatography on silica gel (hexane/ethyl acetate 1:4) 175 mg of (S)-2-[[4-[2-(4-ethoxycarbonylmethoxy-phenyl)-1-methyl-2-oxo-ethylcarbamoyl]-phenyl]-imino-methylcarbamoyloxy]-ethyl propionate, MS (ISP): 542 (M+H)$^+$.

Example 168

In analogy to Example 165 a), from 511 mg of ethyl (S)-4-[2-[4-(amino-imino-methyl)-benzoylamino]-propionyl]-phenoxyacetate trifluoroacetate and 132 mg of 2-hydroxy-ethyl isobutyrate there are obtained after chromatography on silica gel (hexane/ethyl acetate 1:2) 42 mg of (S)-2-[[4-[2-(4-ethoxycarbonylmethoxy-phenyl)-1-methyl-2-oxo-ethylcarbamoyl]-phenyl]-imino-methylcarbamoyloxy]-ethyl 2-methylpropionate, MS (ISP): 556 (M+H)$^+$.

Example 169

In analogy to Example 165 a), from 511 mg of ethyl (S)-4-[2-[4-(amino-imino-methyl)-benzoylamino]-propionyl]-phenoxyacetate trifluoroacetate and 130 mg of 2-hydroxy-ethyl methacrylate there are obtained after chromatography an silica gel (hexane/ethyl acetate 1:3) 160 mg of (S)-2-[[4-[2-(4-ethoxycarbonylmethoxy-phenyl)-1-methyl-2-oxo-ethylcarbamoyl]-phenyl]-imino-methylcarbamoyloxy]-ethyl 2-methyl-acrylate, MS (ISP): 554 (M+H)$^+$.

Example 170

In analogy to Example 165 a), from 511 mg of ethyl (S)-4-[2-[4-(amino-imino-methyl)-benzoylamino]-propionyl]-phenoxyacetate tri-fluoroacetate and 166 mg of 2-hydroxy-ethyl benzoate there are obtained after chromatography on silica gel (hexane/ethyl acetate 1:2) 130 mg of (S)-2-[[4-[2-(4-ethoxycarbonylmethoxy-phenyl)-1-methyl-2-oxo-ethyl-carbamoyl]-phenyl]-imino-methylcarbamoyloxy]-ethyl benzoate, MS (ISP): 590 (M+H)$^+$.

Example 171

In analogy to Example 165 a), from 511 mg of ethyl (S)-4-[2-[4-(amino-imino-methyl)-benzoylamino]-propionyl]-phenoxyacetate trifluoroacetate and 224 mg of 2-hydroxy-ethyl 2-acetoxybenzoate there are obtained after chromatography on silica gel (hexane/ethyl acetate 1:4) 210 mg of (S)-2-[[4-[2-(4-ethoxycarbonylmethoxy-phenyl)-1-methyl-2-oxo-ethylcarbamoyl]-phenyl]-imino-methylcarbamoyloxy]-ethyl 2-acetoxybenzoate, MS (ISP): 648 (M+H)$^+$.

Example 172

In analogy to Example 165 a), from 511 mg of ethyl (S)-4-[2-[4-(amino-imino-methyl)-benzoylamino]-propionyl]-phenoxyacetate trifluoroacetate and 103 mg of acetic acid 2-hydroxyethyl amide there are obtained after chromatography an silica gel (ethyl acetate) 54 mg of ethyl (S)-[4-[2-[4-[(2-acetylamino-ethoxycarbonylimino)-amino-methyl]-benzoylaminol-propionyl]-phenoxy]-acetate, MS (ISP): 527 (M+H)$^+$.

Example 173

A suspension of 263 mg of ethyl (S)-4-[2-[4-(amino-imino-methyl)-benzoylamino]-propionyl]-phenoxyacetate trifluoroacetate, 217 mg of 4-nitro-phenoxycarbonyloxymethyl acetate and 165 ml of 4-methylmorpholine in 5 ml of dichloromethane and 5 ml of tetrahydrofuran is stirred at room temperature for 16 h. Concentration of the reaction mixture and chromatography of the residue on silica gel (hexane/ethyl acetate 1:4) gives 193 mg of ethyl (S)-[4-[2-[4-(acetoxymethoxycarbonylimino-amino-methyl)-benzoylamino]-propionyl]-phenoxy]-acetate, $[\alpha]_D^{20} = +65.0°$ (c=0.6, Chloroform).

Example 174

In analogy to Example 165 a), from 250 mg of ethyl (S)-4-[2-[4-(amino-imino-methyl)-benzoylamino]-propionyl]-phenoxyacetate trifluoroacetate and 104 mg of ethyl (S)-lactate there are obtained after chromatography on silica gel (hexane/ethyl acetate 1:2) 160 mg of methyl (S)-2-[[4-[(S)-2-(4-ethoxycarbonylmethoxy-phenyl)-1-methyl-2-oxo-ethylcarbamoyl]-phenyl]-imino-methylcarbamoyloxy]-propionate, MS (ISP): 528 (M+H)$^+$.

Example 175

Analogously to Example 31, from 380 mg of methyl 1-(8-cyano-5-oxo-2,3,4,5-tetrahydro-1,4-benzoxazepin-4-ylacetyl)-piperidin-4-yloxy-acetate there are obtained after reaction with ammonium acetate, concentration of the reaction solution and precipitation of the product with ether 130 mg of methyl 1-[8-(amino-imino-methyl)-5-oxo-2,3,4,5-tetra-hydro-1,4-benzoxazepin-4-ylacetyl]-piperidin-4-ylQxyacetate acetate, MS (ISP): 419 (M+H)$^+$.

The starting material can be prepared as follows:

a) A solution of 1.63 g of 4-cyanosalicylic acid and 1.26 g of N-hydroxysuccinimide in 25 ml of dichloromethane and 25 ml of dimethylformamide is treated at 0° C. with 2.06 g of dicyclohexylcarbodiimide and stirred at 0° C. for 16 h. The precipitate is filtered off under suction. 1.4 ml of triethylamine and 1.38 g of N-(2-hydroxyethyl) glycine tert-butyl ester (EP 288256) are added to the mother liquor and the mixture is stirred at room temperature for 1 h. Concentration of the reaction solution and chromatography of the residue on silica gel (hexane/ethyl acetate 1:2) gives 475 mg of tert-butyl [(4-cyano-2-hydroxy-benzoyl)-(2-hydroxy-ethyl)-amino]-acetate, MS (ISP): 321 (M+H)$^+$.

b) 378 mg of diethyl azodicarboxylate in 5 ml of tetrahydrofuran are added dropwise at 0° C. to a solution of 464 mg of tert-butyl [(4-cyano-2-hydroxy-benzoyl)-(2-hydroxy-ethyl)-amino]-acetate and 570 mg of triphenylphosphine in 10 ml of tetrahydrofuran and the mixture is stirred at room temperature for 1 h. Concentration of the solution and chromatography of the residue on silica gel (hexane/ethyl acetate 2:1) gives 300 mg of tert-butyl 8-cyano-5-oxo-2,3,4,5-tetrahydro-1,4-benzoxazepin-4-yl-acetate, MS (EI): 246 (M-56).

c) Cleavage of the ester group in 300 mg of the preceding step product in 4 ml of dichloromethane and 2 ml of trifluoroacetic acid is effected at room temperature. The solution is concentrated, the residue is filtered off under suction with ether, dissolved in 50 ml of dimethylformamide and treated with 292 mg of 4-methylmorpholine, 597 mg of O-benzotriazol-1-yl-N,N,N',N'-tetramethyluronium hexafluorophosphate and 330 mg of methyl 4-piperidinoxyacetate hydrochloride. After stirring at room temperature for 16 h. the solution is concentrated, the residue is taken up in ethyl acetate, the organic phase is washed with 1M KHSO$_4$ solution and sat. NaCl solution, dried and concentrated. Chromatography of the residue on silica gel (ethyl acetate) gives 400 mg of methyl 1-(8-cyano-5-oxo-2,3,4,5-tetrahydro-1,4-benzoxazepin-4-ylacetyl)-piperidin-4-yloxyacetate, MS (ISP): 402 (M+H)$^+$.

Example 176

A) By treating 350 mg of ethyl (S)-[1-[2-(8-cyano-5-oxo-2,3,4,5-tetra-hydro-1,4-benzoxazepin-4-yl)-propionyl]-piperidin-4-yloxy]-acetate with hydrogen sulphide, methyl iodide and ammonium acetate there are obtained, after chromatography on silylated silica gel RP18, 163 mg of ethyl (S)-[1-[2-[8-(amino-imino-methyl)-5-oxo-2,3,4,5-tetrahydro-1,4-benzoxazepin-4-yl]-propionyl]-piperidin-4-yloxy]-acetate trifluoroacetate, MS (ISP): 447 (M+H)$^+$.

B) 29 mg of ethyl chloroformate are added to a suspension of 135 mg of ethyl (S)-[1-[2-[8-(amino-imino-methyl)-5-oxo-2,3, 4,5-tetrahydro-1,4-benzoxazepin-4-yl]-propionyl]-piperidin-4-yloxy]-acetate trifluoroacetate in 3 ml of dichloromethane and 3 ml of saturated NaHCO$_3$ solution and the mixture is subsequently stirred at room temperature for 5 min. The aqueous phase is extracted with dichloromethane, the dichloromethane phases are washed with water, dried and concentrated. After chromatography of the residue on silica gel (ethyl acetate) there are obtained 86 mg of ethyl (S)-[1-[2-[8-(amino-ethoxycarbonylimino-methyl)-5-oxo-2,3,4,5-tetrahydro-1,4-benzoxazepin-4-yl]-propionyl]-piperidin-4-yloxy]-acetate, MS (ISP): 519 (M+H)$^+$.

The starting material can be prepared as follows:

a) A solution of 1 g of tert-butyl D-lactate and 0.95 ml of triethylamine in 10 ml of dichloromethane is treated at 0° C. with 1.93 g of trifluoromethanesulphonic anhydride, stirred at 0° C. for 1 h., again treated with 0.95 ml of triethylamine and with 1.43 g of O-tert-butyl-dimethylsilyl-aminoethanol. After stirring at room temperature for 2 h. the reaction mixture is concentrated and the residue is chromatographed on silica gel (hexane/ethyl acetate 2:1). There are obtained 990 mg of tert-butyl (S)-2-[2-(tert-butyl-dimethyl-silanyloxy)-ethylamino]-propionate, MS (EI): 246 (M-57).

b) In analogy to Example 175 a), 5 g of 4-cyanosalicylic acid are reacted with 4.36 g of the preceding step product and the evaporation residue is chromatographed on silica gel (hexane/tert-butyl methyl ether 2:1). There are obtained 1.19 g of tert-butyl (S)-2-[2-(tert-butyl-dimethyl-silanyloxy)-ethyl]-(4-cyano-2-hydroxy-benzoyl)-amino]-propionate, MS (EI): 449 (M+H)⁺.

c) A solution of 1.19 g of the preceding step product in 25 ml of ether is treated with 2.7 ml of tetrabutylammonium fluoride (1M in tetrahydrofuran), stirred at room temperature for 16 h., washed with 1M H₃PO₄ solution and sat. NaCl solution, dried and concentrated. Chromatography of the residue on silica gel (ethyl acetate) gives 704 mg of tert-butyl (S)-2-[(4-cyano-2-hydroxy-benzoyl)-(2-hydroxy-ethyl)-amino]-propionate, MS (ISP): 335 (M+H)⁺.

d) Reaction of 669 mg of the preceding step product in analogy to Example 175 b) gives, after chromatography on silica gel (hexane/ethyl acetate 2:1), 345 mg of tert-butyl (S)-2-(8-cyano-5-oxo-2,3,4,5-tetrahydro-1,4-benzoxazepin-4-yl)-propionate, MS (EI): 260 (M-56).

e) In analogy to Example 175 c), 340 mg of the preceding step product are reacted with 243 mg of ethyl 4-piperidinoxyacetate. After chromatography of the residue on silica gel (hexane/ethyl acetate 1:3) there are obtained 365 mg of ethyl (S)-[1-[2-(8-cyano-5-oxo-2,3,4,5-tetrahydro-1,4-benzoxazepin-4-yl)-propionyl]-piperidin-4-yloxy]-acetate, $[\alpha]_D^{20}$=−18.8° (c=0.6, Chloroform).

Example 177

Reaction of 80 mg of ethyl (R,S)-4-[2-[4-(amino-imino-methyl)-2-methoxy-benzoylamino]-propionyl]-phenoxyacetate hydroiodide with 22 mg of ethyl chloroformate according to Example 176 B) gives, after chromatography on silica gel (hexane/ethyl acetate 1:3), 58 mg of ethyl (R,S)-[4-[2-[4-(amino-ethoxycarbonylimino-methyl)-2-methoxy-benzoyl-amino]-propionyl]-phenoxy]-acetate as a colourless oil, MS (ISP): 500 (M+H)⁺.

The starting material can be prepared as follows:

a) A solution of 1.92 g of 4-cyanosalicylic acid and 1.49g of N-hydroxysuccinimide in 30 ml of dichloromethane and 30 ml of dimethylformamide is treated at 0° C. with 2.43 g of dicyclohexylcarbodiimide and stirred at −14° C. to 15° C. for 16 h. The precipitate is filtered off under suction and the mother liquor containing the 4-cyanosalicylic acid hydroxysuccinimide ester is used directly in the next step.

b) Cleavage of the BOC group in 4.1 g of ethyl (S)-4-(2-tert-butoxycarbonylamino-propionyl)-phenoxy acetate (Example 23 a) is effected with 1.75 ml of trimethylsilyl iodide at 0° C. in 40 ml of dichloromethane. After the addition of 8 ml of 4N HCl in dioxan the reaction solution is concentrated, the residue is dissolved in 40 ml of tetrahydrofuran and added together with 2.6 ml of 4-methylmorpholine to the mother liquor which is obtained in the preceding step and which contains the 4-cyanosalicylic acid hydroxysuccinimide ester. After 16 hours at room temperature the mixture is concentrated and the residue is chromatographed on silica gel (hexane/ethyl acetate 3:1). There are obtained 2.98 g of ethyl (S)-[4-[2-(4-cyano-2-hydroxy-benzoyl-amino)-propionyl]-phenoxy]-acetate, MS (ISP): 397 (M+H)⁺.

c) Alkylation of 792 mg of the preceding step product with 0.19 ml of methyl iodide in the presence of 830 mg of potassium carbonate in 20 ml of dimethylformamide for 2 h. at room temperature gives, after concentration of the solution and chromatography of the residue on silica gel (hexane/ethyl acetate 3:1), 580 mg of ethyl (R,S)-[4-[2-(4-cyano-2-methoxy-benzoylamino)-propionyl]-phenoxy]-acetate, MS (ISP): 411 (M+H)⁺.

d) In analogy to Example 31, 290 mg of the preceding step product are reacted with hydrogen sulphide, methyl iodide and ammonium acetate, the reaction solution is concentrated to half and the product is precipitated by the addition of ether. There are obtained 183 mg of ethyl (R,S)-[4-[2-[4-(amino-imino-methyl)-2-methoxy-benzoylamino]-propionyl]-phenoxy]-acetate hydroiodide, MS (ISP): 428 (M+H)⁺.

Example 178

Reaction of 1.4 g of ethyl (R,S)-[4-[2-(4-cyano-phenyl)-1-methyl-2-oxo-ethylcarbamoyl]-phenoxy]-acetate with hydrogen sulphide, methyl iodide and ammonium acetate in analogy to Example 31 gives, after chromatography of the evaporation residue on silylated silica gel RP 18 (water/tetrahydrofuran gradient), 410 mg of ethyl (R,S)-[4-[2-[4-(amino-imino-methyl)-phenyl]-1-methyl-2-oxo-ethylcarbamoyl]-phenoxy]-acetate hydroiodide, MS (ISP): 398 (M+H)⁺.

The starting material can be prepared as follows:

a) A solution of 10.92 g of 4-bromobenzonitrile in 80 ml of tetrahydrofuran is added dropwise at −78° C. to 37.5 ml of 1.6 N n-butyllithium. The resulting suspension is stirred at −78° C. for 30 min., added at the same temperature to 4.65 g of (S)-2-tert-butoxycarbonylamino-N-methoxy-N-methyl-propionamide in 80 ml of tetrahydrofuran and stirred at −78° C. for 1 h. The red reaction solution is poured into 1M H₃PO₄. Extraction with ether, washing of the organic phases with sat. NaCl solution, drying and concentration of the solution gives a residue which, after chromatography on silica gel, leads to 3.68 g of tert-butyl (S)-2-(4-cyano-phenyl)-1-methyl-2-oxo-ethylcarbamate, $[\alpha]_D^{20}$=−57° (c=1, chloroform).

b) Cleavage of the BOC group in 1.92 g of the preceding step product is effected analogously to Example 177 b). The resulting amine hydrochloride is added at 0° C. to 1.89 g 4-tert-butyl-dimethyl-silanyloxy-benzoyl chloride in 20 ml of pyridine and the mixture is stirred at room temperature for 16 h. Concentration of the solution and chromatography of the residue on silica gel (hexane/ethyl acetate 2:1) gives 1.84 g of (S)-4-(tert-butyl-dimethyl-silanyloxy)-N-[2-(4-cyano-phenyl)-1-methyl-2-oxo-ethyl]-benzamide, $[\alpha]_D^{20}$=+45.9° (c=0.7, chloroform).

c) Deprotection of 1.81 g of the preceding step product gives 1.4 g of (R,S)-N-[2-(4-cyano-phenyl)-1-methyl-2-oxo-ethyl]-4-hydroxy-benzamide, MS (ISP): 293 (M−H)⁺.

d) Alkylation of 1.4 g of the preceding step product with 0.65 ml of ethyl bromoacetate in the presence of K₂CO₃ in dimethylformamide at room temperature for 2 h. gives, after removal of the solvent and chromatography on silica gel (hexane/ethyl acetate 1:1), 1.23 g of ethyl (R,S)-[4-[2-(4-cyano-phenyl)-1-methyl-2-oxo-ethylcarbamoyl]-phenoxy]-acetate, MS (ISP): 381 (M+H)⁺.

Example 179

A solution of 50 mg of ethyl (R,S)-[4-[2-[4-[amino-(tert-butyl-dimethyl-silanyloxyimino)-methyl]-phenyl]-1-methyl-2-oxo-ethylcarbamoyl]-phenoxy]-acetate in 1 ml of ether is stirred at 0° C. for 1 h. with 0.1 ml of tetrabutylammonium fluoride (1M in tetrahydrofuran), concentrated and the residue is chromatographed on silica gel (hexane/ethyl acetate 1:2). There are obtained 11 mg of ethyl (R,S)-[4-[2-[4-(amino-hydroxyimino-methyl)-phenyl]-1-methyl-2-oxo-ethylcarbamoyl]-phenoxy]-acetate, MS (ISP): 414 (M+H)$^+$.

The starting material can be prepared as follows:

In analogy to Example 31, 0.6 g of ethyl (R,S)-[4-[2-(4-cyano-phenyl)-1-methyl-2-oxo-ethylcarbamoyl]-phenoxy]-acetate is reacted with hydrogen sulphide and methyl iodide. 147 mg of O-tert-butyl-dimethyl-silyl-hydroxylamine are stirred at room temperature for 2 h. with the resulting methylthioimine in 6 ml of tetrahydrofuran. Chromatography of the residue on silica gel (hexane/ethyl acetate 3:2) leads to 50 mg of ethyl (R,S)-[4-[2-[4-[amino-(tert-butyl-dimethyl-silanyloxyimino)-methyl]-phenyl]-1-methyl-2-oxo-ethylcarbamoyl]-phenoxy]-acetate, MS (ISP): 414 (M-113).

Example 180

From 743 mg of ethyl (S)-4-(2-piperidin-4-yloxyacetylamino-propionyl)-phenoxy-acetate hydrochloride in 20 ml of ethanol and 20 ml of acrylonitrile there are obtained after 5 days at 80° C. and after chromatography of the evaporation residue on silica gel (dichloromethane/5% methanol) 250 mg of ethyl (S)-[4-[2-[1-(2-cyano-ethyl)-piperidin-4-yloxyacetylamino]-propionyl]-phenoxy]-acetate, MS (ISP): 446 (M+H)$^+$.

A solution of 250 mg of ethyl (S)-[4-[2-[1-(2-cyano-ethyl)-piperidin-4-yloxyacetylamino]-propionyl]-phenoxy]-acetate in 10 ml of dichloromethane is treated at 0° C. with 128 mg of meta-chloroperbenzoic acid and stirred at 0° C. for 1 h. The reaction solution is washed with sat. NaHCO$_3$ solution and sat. NaCl solution, dried and concentrated. Chromatography of the residue on silica gel gives 140 mg of ethyl (S)-[4-[2-(1-hydroxy-piperidin-4-yloxyacetylamino)-propionyl]-phenoxy]-acetate, MS (ISP): 409 (M+H)$^+$.

Example 181

A solution of 285 mg of ethyl (S)-4-(2-piperidin-4-yloxy-acetylamino-propionyl)-phenoxy acetate, 0.11 ml of 4-methylmorpholine and 217 mg of 4-nitro-phenoxycarbonyloxymethyl acetate is stirred at room temperature for 5 h., concentrated and the residue is chromatographed on silica gel (hexane/ethyl acetate 1:2). There are obtained 205 mg of acetoxymethyl (S)-4-[2-(4-ethoxycarbonylmethoxy-phenyl)-1-methyl-2-oxo-ethylcarbamoylmethoxy]-piperidine-1-carboxylate, $[\alpha]_D^{20}$=+23.7° (c=0.35, chloroform).

Example 182

Cleavage of the BOC protecting group in 3.45 g of tert-butyl (S)-4-[1-tert-butoxymethyl-2-(4-ethoxycarbonylmethoxy-phenyl)-2-oxo-ethylcarbamoylmethoxy]-piperidine-1-carboxylate in 60 ml of dichloromethane and 30 ml of trifluoroacetic acid gives, after concentration of the solvent and chromatography of the residue on silylated silica gel RP 18 (water/tetrahydrofuran gradient), 1.9 g of ethyl (S)-[4-[3-hydroxy-2-(2-piperidin-4-yloxy-acetylamino)-propionyl]-phenoxy]-acetate trifluoroacetate, MS (ISP): 409 (M+H)$^+$.

The starting material can be prepared as follows:

a) In analogy to Example 177 b) the BOC group is cleaved in 3.5 g of ethyl (S)-4-[3-tert-butoxy-2-tert-butoxycarbonylamino-propionyl]-phenoxy acetate (Example 7 d) and the resulting amine is stirred at room temperature for 16 h. with 2.57 g of 1-tert-butoxycarbonylpiperidin-4-yl-oxyacetic acid in the presence of 2.95 g of TPTU and 1.82 ml of 4-methylmorpholine in 60 ml of dichloromethane. After removal of the solvent and chromatography of the residue on silica gel (hexane/ethyl acetate 1:2) there are obtained 3.5 g of tert-butyl (S)-4-[1-tert-butoxy-methyl -2-(4-ethoxycarbonylmethoxy-phenyl)-2-oxo-ethyl-carbamoylmethoxy]-piperidine-1-carboxylate as a yellow oil, MS (ISP): 565 (M+H)$^+$.

Example 183

Analogously to Example 181, 480 mg of ethyl (S)-[4-[3-hydroxy-2-(2-piperidin-4-yloxy-acetylamino)-propionyl]-phenoxy]-acetate are reacted with 367 mg of 4-nitro-phenoxycarbonyloxymethyl acetate and the residue is chromatographed on silica gel (ethyl acetate). There are obtained 161 mg of ethyl (S)-[4-[2-[(1-Acetoxymethoxycarbonyl-piperidin- 4-yloxy)-acetylamino]-3-hydroxy-propionyl]-phenoxy] acetate as a colourless oil, MS (ISP): 525 (M+H)$^+$.

Example 184

A solution of 800 mg of tert-butyl (S)-4-[[2-(4-ethoxy-carbonylmethoxy-phenyl)-1-methyl-2-oxo-ethyl]-methyl-carbamoylmethoxyl-piperidine-1-carboxylate in 10 ml of dichloromethane and 5 ml of trifluoroacetic acid is stirred at room temperature for 1 h. and concentrated. Chromatography of the residue on silylated silica gel RP 18 (water/tetrahydrofuran gradient) gives 509 mg of ethyl (S)-4-[2-[methyl-(piperidin-4-yloxy-acetyl)-amino]-propionyl]-phenoxy]-acetate trifluoroacetate, MS (ISP): 407 (M+H)$^+$.

The starting material can be prepared as follows:

a) Coupling of 5 g of (S)-N-tert-butoxycarbonyl-N-methyl-2-amino-propionic acid with 2.88 g of N,O-dimethylhydroxylamine hydrochloride in 100 ml of dichloromethane in the presence of 8.77 g of TPTU and 5.96 ml of 4-methylmorpholine gives, after stirring at room temperature for 16 h., concentration of the reaction solution and chromatography of the residue on silica gel (hexane/ethyl acetate 2:1), 4.43 g of tert-butyl (S)-[1-(methoxy-methyl-carbamoyl)-ethyl]-methylcarbamate, $[\alpha]_D^{20}$=-62.3° (c=1, chloroform).

b) After reacting 4.1 g of the preceding step product with p-bromo-tert-butyl-dimethylsilylphenol analogously to Example 3 a) and chromatography of the residue on silica gel (hexane/ethyl acetate 95:5) there are obtained 2.82 g of tert-butyl (S)-[2-(4-tert-butyl-dimethyl-silanyloxy)-phenyl]-1-methyl-2-oxo-ethyl]-methylcarbamate as a colourless oil, $[\alpha]_D^{20}$=-127.0° (c=0.5, chloroform).

c) Deprotection of 2.2 g of the preceding step product analogously to Example 3 b) gives 1.41 g of tert-butyl (S)-[2-(4-hydroxy-phenyl)-1-methyl-2-oxo-ethyl]-methylcarbamate, $[\alpha]_D^{20}$=-179.4° (c=0.7, chloroform).

d) Alkylation of 615 mg of the preceding step product analogously to Example 3 c) and chromatogaphy of the evaporation residue on silica gel (hexane/ethyl acetate 3:1) gives 674 mg of ethyl (S)-[4-[2-(tert-butoxycarbonyl-methyl-amino)-propionyl]-phenoxy]-acetate, $[\alpha]_D^{20}$=-135.0° (c=0.5, chloroform).

e) Cleavage of the BOC protecting group in 810 mg of the preceding step product is effected analogously to Example 177 b) at −78° C. The resulting amine is stirred at room temperature for 20 h. with 498 mg of 1-tert-butoxycarbonylpiperidin-4-yl-oxyacetic acid in the presence of 570 mg of TPTU and 0.39 ml of 4-methylmorpholine in 30 ml of dichloromethane. After removal of the solvent and chromatography of the residue on silica gel there are obtained 890 mg of tert-butyl (S)-4-[[2-(4-ethoxycarbonylmethoxy-phenyl)-1-methyl-2-oxo-ethyl]-methyl-carbamoylmethoxy]-piperidin-1-carboxylate as a colourless oil, MS (ISP): 507 (M+H)⁺.

Example 185

A solution of 850 mg of tert-butyl (S)-4-[2-[2-(4-ethoxycarbonylmethoxy-phenyl)-1-methyl-2-oxo-ethylcarbamoyl]-ethyl]-piperidine-1-carboxylate in 5 ml of dichloromethane and 2.5 ml of trifluoroacetic acid is stirred at room temperature for 1 h. and concentrated. There are obtained 760 mg of ethyl (S)-[4-[2-(3-piperidin-4-yl-propionylamino)-propionyl]-phenoxy]-acetate trifluoroacetate as a colourless oil, MS (ISP): 391 (M+H)⁺.

The starting material can be prepared as follows:

Cleavage of the BOC protecting group in 740 mg of ethyl (S)-4-(2-tert-butoxycarbonylamino-propionyl)-phenoxyacetate is effected analogously to Example 177 b). The resulting amine is stirred at room temperature for 16 h. with 500 mg of 1-tert-butoxycarbonylpiperidin-4-yl-propionic acid in the presence of 570 mg of TPTU and 0.46 ml of 4-methylmorpholine in 10 ml of dichloromethane. After removal of the solvent and chromatography of the residue on silica gel (hexane/ethyl acetate 2:3) there are obtained 890 mg of tert-butyl (S)-4-[2-[2-(4-ethoxycarbonylmethoxy-phenyl)-1-methyl-2-oxo-ethylcarbamoyl]-ethyl]-piperidine-1-carboxylate as a yellow oil, MS (ISP): 491 (M+H)⁺.

Example 186

Starting from 300 mg of ethyl (S)-[4-[2-(3-piperidin-4-yl-propionylamino)-propionyl]-phenoxy]-acetate trifluoroacetate there are obtained, analogously to Example 181 and after chromatography on silica gel (hexane/ethyl acetate 1:2) 140 mg of ethyl (S)-4-[2-[3-(1-acetoxymethoxycarbonyl-piperidin-4-yl)-propionylamino]-propionyl]-phenoxy]-acetate, MS (ISP): 507 (M+H)⁺.

Example 187

A solution of 100 mg of tert-butyl (R)-3-[(S)-1-(4-ethoxy-carbonylmethoxy-benzoyl)-ethylcarbamoylmethoxy]-pyrrolidine-1-carboxylate in 2 ml of dichloromethane and 1 ml of trifluoroacetic acid is stirred at room temperature for 2 h., concentrated and the residue is chromatographed on silylated silica gel RP 18 (water/tetrahydrofuran gradient). There are obtained 70 mg of ethyl [4-[(S)-2-[(R)-2-pyrrolidin-3-yloxy-acetylamino]-propionyl]-phenoxy]-acetate trifluoroacetate, MS (ISP): 379 (M+H)⁺.

The starting material can be prepared as follows:

a) The phase transer reaction of 4.1 g of tert-butyl (R)-3-hydroxy-pyrrolidine-1-carboxylate with 3.85 ml of tert-butyl bromoacetate in 50 ml of toluene and 50 ml of 50% NaOH in the presence of 500 mg of tetrabutylammonium hydrogen sulphate has finished after 1 h. Washing of the organic phase with sat. NaCl solution, drying and concentration gives a residue which, after chromatogaphy on silica gel (hexane/ethyl acetate 3:1), leads to 4.98 g of tert-butyl (R)-3-tert-butoxycarbonylmethoxy-pyrrolidine-1-carboxylate, MS (ISP): 302 (M+H)⁺.

b) A solution of 4.95 g of the preceding step product in 50 ml of dichloromethane and 25 ml of trifluoroacetic acid is stirred at room temperature for 3 h. and concentrated. The residue is dissolved in 40 ml of dioxan and 40 ml of 1N NaOH, treated at room temperature with 4.3 g of di-tert-butyl dicarbonate in 40 ml of dioxan and stirred for 1.5 h. The reaction mixture is diluted with ether, the organic phase is washed with 1N NaOH and the aqueous phase is acidified with 3N HCl. Extraction of the aqueous phase with ether, washing, drying and concentration of the ether phase gives 0.72 g of tert-butyl (R)-3-carboxymethyl-pyrrolidine-1-carboxylate. 360 mg of this are reacted with ethyl (S)-4-(2-tert-butoxycarbonylamino-propionyl) phenoxyacetate, deprotected according to Example 177 b), in 15 ml of dichloromethane in the presence of 446 mg of TPTU and 0.33 ml of 4-methylmorpholine. Concentration of the reaction solution and chromatography of the residue gives 100 mg of tert-butyl (R)-3-[(S)-1-(4-ethoxycarbonylmethoxy-benzoyl)-ethyl-carbamoylmethoxy]-pyrrolidine-1-carboxylate, MS (ISP): 479 (M+H)⁺.

Example 188

A solution of 290 mg of tert-butyl (S)-6-[2-(4-ethoxy-carbonylmethoxy-phenyl)-1-methyl-2-oxo-ethylcarbamoyl]-1,2,3,4-tetrahydro-isoquinoline-2-carboxylate in 4 ml of dichloromethane and 2 ml of trifluoroacetic acid is stirred at room temperature for 1 h., concentrated and the residue is chromatographed on silylated silica gel RP 18 (water/tetrahydrofuran gradient). There are obtained 174 mg of ethyl (S)-[4-[2-(1,2,3,4-tetrahydro-isoquinoline-6-ylcarbonylamino)-propionyl]-phenoxy]-acetate trifluoroacetate, $[\alpha]_D$=+51.7° (c=0.6, DMSO).

The starting material can be prepared as follows:

a) 1.38 g of di-tert-butyl dicarbonate in 10 ml of dioxan and 10 ml of 1N NaOH are added simultaneously at 0° C. to a solution of 1.46 g of 6-hydroxy-1,2,3,4-tetrahydro-isoquinoline hydrobromide in 10 ml of dioxan and 2 ml of 1N NaOH. After stirring at room temperature for 3 h. the reaction mixture is adjusted to pH5 with 1N HCl, extracted with ether, the ether phases are washed with sat. NaCl solution, dried and concentrated. Chromatography of the residue on silica gel gives 1.07 g of tert-butyl 6-hydroxy-1,2,3,4-tetrahydro-isoquinoline-2-carboxylate, MS (EI): 192 (M-57).

b) At −15° C. a solution of 918 mg of the preceding step product in 10 ml dichloromethane is treated with 1.2 ml of triethylamine and subsequently with 0.7 ml of trifluoromethanesulphonic anhydride and stirred at room temperature for 2 h. The precipitate is filtered off under suction, the filtrate is concentrated and the residue is chromatographed on silica gel (hexane/ethyl acetate 7:1). There are obtained 1.02 g of tert-butyl 6-trifluoromethylsulphonyloxy-1,2,3,4-tetrahydro-isoquinoline-2-carboxylate, MS (EI): 324 (M-57).

c) 950 mg of the preceding step product are reacted at 80° C. for 2 h. with CO in the presence of 17 mg of palladium acetate, 32 mg of 1,3-bis-(diphenylphosphino)-propane and 0.4 ml of triethylamine in 4 ml of DMSO and 2.6 ml of methanol. The reaction solution is diluted with sat. NaCl solution, extracted with ether, the ether phases are washed with sat. NaCl solution, dried and concentrated. Chromatography of the residue on silica gel gives 443 mg of 2-tert-butyl 6-methyl 1,2,3,4-tetrahydro-isoquinoline-2,6-dicarboxylate, MS (ISP): 292 (M+H)⁺.

d) Saponification of 387 mg of the preceding step product with 213 mg of NaOH in 9 ml of methanol and 1 ml of water is effected at room temperature for 6 h. The reaction solution is concentrated and diluted with water. The aqueous phase is extracted with ether, adjusted to pH 5 with 1N HCl and the precipitate is filtered off under suction. After washing the crystals with water and drying there are obtained 274 mg of 1,2,3,4-tetrahydro-isoquinoline-2,6-dicarboxylic acid 2-tert-butyl ester, MS (EI): 220 (M-57).

e) Cleavage of the BOC protecting group in 313 mg of ethyl (S)-4-(2-tert-butoxycarbonylamino-propionyl)-phenoxy acetate analogously to Example 177 b) gives the amine. This is stirred at room temperature for 48 h. with 247 mg of the preceding step product, 264 mg of TPTU and 0.20 ml of 4-methylmorpholine in 10 ml of dichloromethane. After chromatography of the evaporation residue on silica gel (hexane/ethyl acetate 1:1) there are obtained 444 mg of tert-butyl (S)-6-[2-(4-ethoxycarbonylmethoxy-phenyl)-1-methyl-2-oxo-ethylcarbamoyl]-1,2,3,4-tetrahydro-isoquinoline-2-carboxylate, $[\alpha]_D^{20}$=+51.3° (c=0.4, chloroform).

Example 189

A solution of 106 mg of methyl 1-[8-(amino-imino-methyl)-5-oxo-2,3,4,5-tetrahydro-1,4-benzoxazepin-4-ylacetyl]-piperidin-4-yloxyacetate acetate (Example 175) and 18 mg of lithium hydroxide in 5 ml of methanol and 0.5 ml of water is stirred at room temperature for 16 h., adjusted to pH3 with 1N HCl and concentrated. Chromatography of the residue on silylated silica gel RP 18 (water/tetrahydrofuran gradient) gives 60 mg of 1-[8-(amino-imino-methyl)-5-oxo-2,3,4,5-tetrahydro-1,4-benzoxazepin-4-ylacetyl]-piperidin-4-yloxyacetic acid as white crystals, MS (ISP): 405 (M+H)+.

Example 190

A solution of 200 mg of tert-butyl (R)-3-[(S)-1-(4-tert-butoxycarbonylmethoxy-benzoyl)-ethylcarbamoylmethoxy]-pyrrolidine-1-carboxylate in 2 ml of dichloromethane and 1 ml of trifluoroacetic acid is stirred at room temperature for 4 h., concentrated and the residue is chromatographed on silylated silica gel RP 18 (water/tetrahydrofuran gradient). There are obained 113 mg of [4-[(S)-2-[(R)-2-pyrrolidin-3-yloxy-acetylamino]-propionyl]-phenoxy]-acetic acid trifluoroacetate, MS (ISP): 351 (M+H)+.

The starting material can be prepared as follows:

Coupling of 360 mg of tert-butyl (R)-3-carboxymethoxy-pyrrolidine-1-carboxylate ( Example 187 b) with 569 mg of tert-butyl (S)-4-(2-tert-butoxycarbonylamino-propionyl)-phenoxyacetate, deprotected according to Example 177 b), in 15 ml of dichloromethane in the presence of 446 mg of TPTU and 0.33 ml of 4-methylmorpholine gives, after concentration of the reaction solution and chromatogaphy of the residue on silica gel (hexane/ethyl acetate 1:3), 200 mg of tert-butyl (R)-3-[(S)-1-(4-tert-butoxycarbonylmethoxy-benzoyl)-ethylcarbamoyl-methoxy]-pyrrolidine-1-carboxylate, MS (ISP): 507 (M+H)+.

Example 191

In analogy to Example 185, 231 mg of tert-butyl (S)-4-[[2-(4-tert-butoxycarbonylmethoxy-phenyl)-1-methyl-2-oxo-ethyl]-methyl-carbamoylmethoxy]-piperidine-1-carboxylate are deprotected and chromatographed on silylated silica gel RP 18 (water/tetrahydrofuran gradient). There are obtained 113 mg of (S)-4-[2-[methyl-(piperidin-4-yloxy-acetyl)-amino]-propionyl]-phenoxy]-acetic acid trifluoroacetate, MS (ISP): 379 (M+H)+.

The starting material can be prepared as follows:

a) Alkylation of 723 mg of tert-butyl (S)-[2-(4-hydroxy-phenyl)-1-methyl-2-oxo-ethyl]-methylcarbamate analogously to Example 3 c) and chromatography of the evaporation residue on silica gel (hexane/ethyl acetate 5:1) gives 990 mg of tert-butyl (S)-[4-[2-(tert-butoxycarbonyl-methyl-amino)-propionyl]-phenoxy]-acetate, $[\alpha]_D^{20}$=−124.5° (c=0.4, chloroform).

b) Cleavage of the BOC protecting group in 394 mg of the preceding step product is effected analogously to Example 177 b) at −78° C. The resulting amine is stirred at room temperature for 20 h. with 311 mg of 1-tert-butoxycarbonylpiperidine-4-yl-oxyacetic acid in the presence of 356 mg of TPTU and 222 mg of 4-methylmorpholine in 45 ml of dichloromethane. After removal of the solvent and chromatography of the residue on silica gel (tert-butyl methyl ether/hexane 4:1) there are obtained 179 mg of tert-butyl (S)-4-[[2-(4-tert-butoxycarbonylmethoxy-phenyl)-1-methyl-2-oxo-ethyl]-methyl-carbamoylmethoxy]-piperidine-1-carboxylate as a pale yellow oil, $[\alpha]_D^{20}$=−1207° (c=0.3, chloroform).

Example A

A compound of formula I can be used in a manner known per se as the active substance for the manufacture of tablets of the following composition:

|  | Per tablet |
| --- | --- |
| Active substance | 200 mg |
| microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active substance for the manufacture of capsules of the folowing compositon:

|  | Per capsule |
| --- | --- |
| Active substance | 100.0 mg |
| Corn starch | 20.0 mg |
| Lactose | 95.0 mg |
| Talc | 4.5 mg |
| Magnesium stearate | 0.5 mg |
|  | 220.0 mg |

We claim:

1. The compound ethyl (S)-4-[2-[4-[imino-2-(methoxy-ethoxycarbonylamino)-methyl]-benzoylamino]-propionyl]-phenoxyacetate.

2. The compound ethyl (Z)-(R,S)-4-[2-[4-[amino-hydroxyimino-methyl]-benzoylamino]-propionyl]-phenoxyacetate.

3. The compound tetrahydropyran-4-yl (S)-4-[2-[4-(ethoxycarbonylamino-imino-methyl)-benzoylamino]-propionyl]-phenoxyacetate.

4. The compound ethyl (Z)-(R,S)-4-[2-[4-[amino-ethoxycarbonyloximino-methyl]-benzoylamino]-propionyl]-phenoxyacetate.

5. The compound ethyl (S)-4-[2-[4-(imino-phenoxycarbonylamino-methyl)-benzoylamino]-propionyl]-phenoxyacetate.

6. The compound 2-methoxy-ethyl (S)-4-[2-[4-[imino-(2-methoxy-ethoxycarbonylamino)-methyl]-benzoylamino]-propionyl]-phenoxyacetate.

7. The compound ethyl (Z)-(S)-4-[2-[4-(amino-hydroxyimino-methyl)-benzoylamino]-propionyl]-phenoxyacetate.

8. The compound ethyl (S)-[4-[2-[4-[(2-acetoxy-ethoxycarbonylimino)-amino-methyl]-benzoylamino]-propionyl]-phenoxy]-acetate.

* * * * *